US011832974B2

(12) United States Patent
Montgomery et al.

(10) Patent No.: US 11,832,974 B2
(45) Date of Patent: Dec. 5, 2023

(54) RETROSPECTIVE SMOOTHING

(71) Applicant: Senseonics, Incorporated, Germantown, MD (US)

(72) Inventors: Barbara Montgomery, Gaithersburg, MD (US); Kamuran Turksoy, Germantown, MD (US); Alex Markovic, Germantown, MD (US); Shang Zhao, Germantown, MD (US); Andrew Dehennis, Germantown, MD (US); Samanwoy Ghosh Dastidar, Germantown, MD (US)

(73) Assignee: Senseonics, Incorporated, Germantown, MD (US)

( * ) Notice: Subject to any disclaimer, the term of this patent is extended or adjusted under 35 U.S.C. 154(b) by 102 days.

(21) Appl. No.: 16/717,622

(22) Filed: Dec. 17, 2019

(65) Prior Publication Data

US 2021/0177360 A1 Jun. 17, 2021

(51) Int. Cl.
*A61B 5/00* (2006.01)
*A61B 5/145* (2006.01)

(52) U.S. Cl.
CPC .......... *A61B 5/742* (2013.01); *A61B 5/14532* (2013.01); *A61B 5/725* (2013.01); *A61B 5/7225* (2013.01); *A61B 5/746* (2013.01)

(58) Field of Classification Search
CPC ..... A61B 5/746; A61B 5/7275; A61B 5/7264; A61B 5/725; A61B 5/7246; A61B 5/7242; A61B 5/7239; A61B 5/7235; A61B 5/7221; A61B 5/7225; A61B 5/14546; A61B 5/145; A61B 5/14532; A61B 5/7435; A61B 5/743; A61B 5/742
See application file for complete search history.

(56) References Cited

U.S. PATENT DOCUMENTS

| 2007/0032706 | A1* | 2/2007 | Kamath | A61B 5/14539 |
| | | | | 600/300 |
| 2010/0168538 | A1 | 7/2010 | Keenan et al. | |
| 2010/0298685 | A1 | 11/2010 | Hayter et al. | |
| 2013/0109944 | A1 | 5/2013 | Sparacino et al. | |
| 2019/0357852 | A1 | 11/2019 | Kamath et al. | |

* cited by examiner

*Primary Examiner* — Christian Jang
(74) *Attorney, Agent, or Firm* — Rothwell, Figg, Ernst & Manbeck, P.C.

(57) ABSTRACT

A display device configured to receive raw values, calculate smoothed values, and display the smoothed values only if the smoothed values satisfy a consistency check. In some embodiments, the consistency check may be satisfied if none of the smoothed values (i) corresponds to a raw value that triggered a first or second alarm and (ii) would not also trigger the first or second alarm. In some embodiments, if the smoothed values do not satisfy the consistency check, the display device may re-calculate the smoothed values such that the consistency check is satisfied. The display device may display the smoothed values in place of corresponding raw values in a historical trend graph.

21 Claims, 42 Drawing Sheets

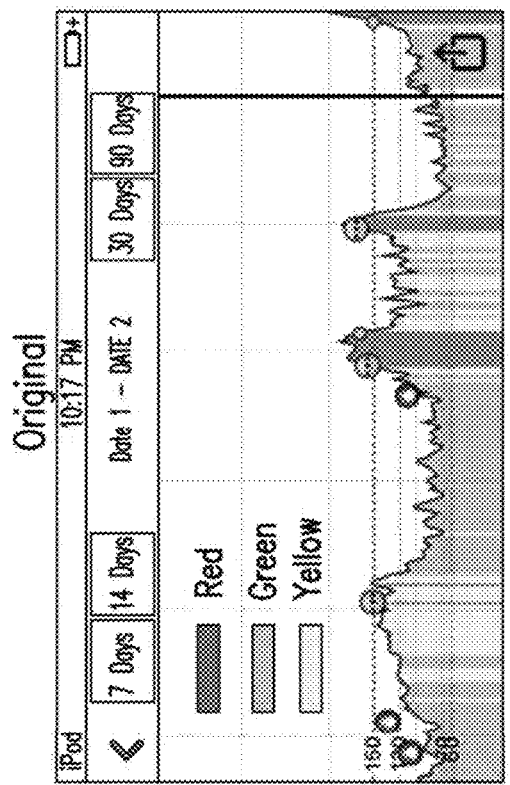
FIG. 11A
FIG. 11B
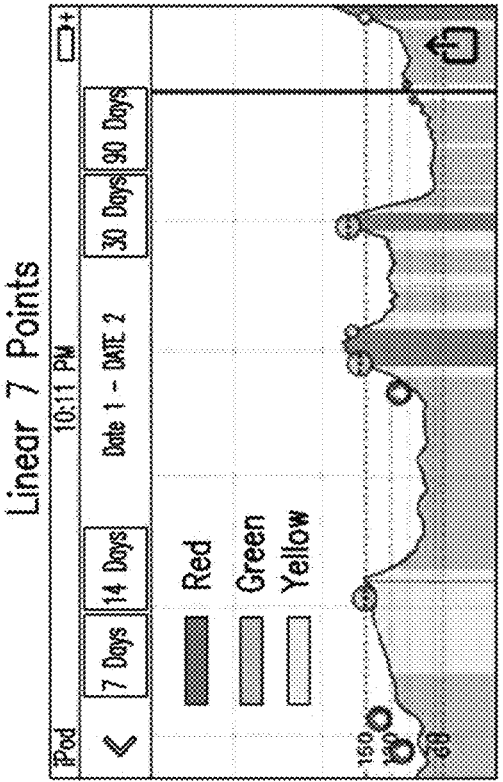
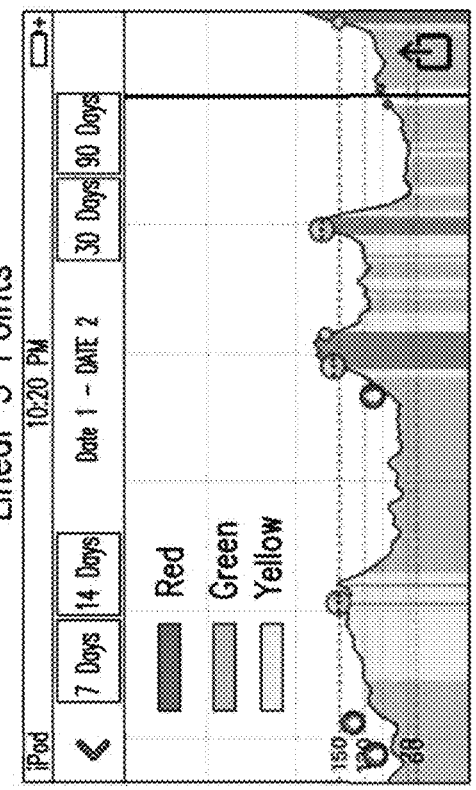
FIG. 11C
FIG. 11D

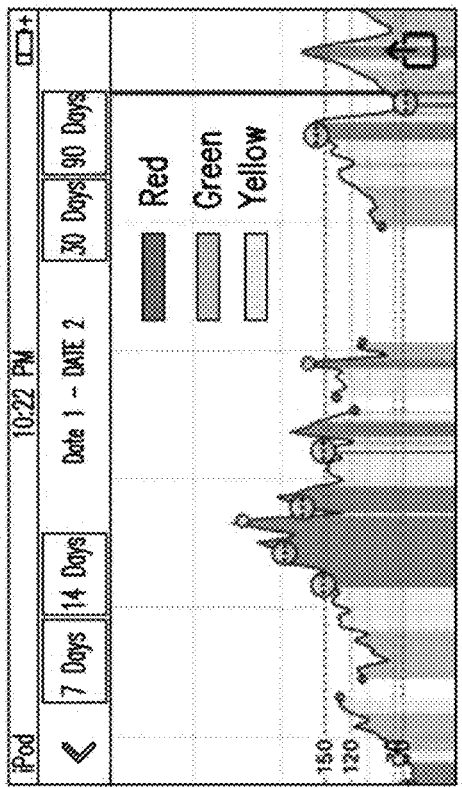
FIG. 13E
FIG. 13F
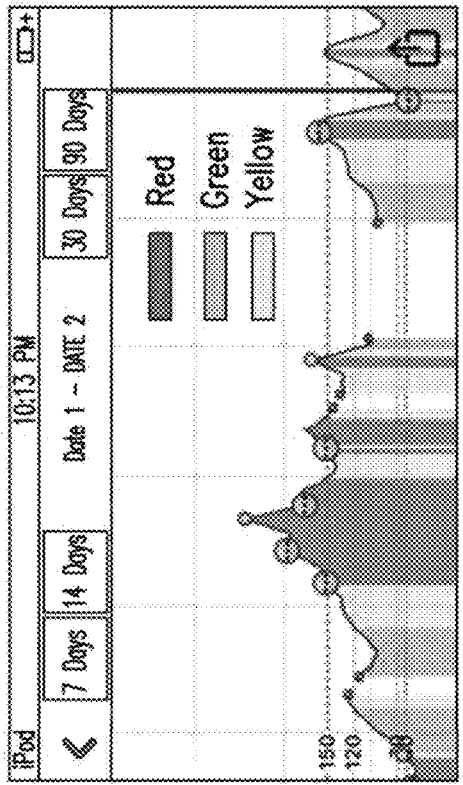
FIG. 13G
FIG. 13H

RETROSPECTIVE SMOOTHING

BACKGROUND

Field of Invention

Aspects of the present invention relate to systems and methods for retrospective smoothing of raw values and display of the smoothed values. Some aspects of the present invention may relate to retrospective smoothing of raw analyte vales in an analyte monitoring system.

Discussion of the Background

The prevalence of diabetes mellitus continues to increase in industrialized countries, and projections suggest that this figure will rise to 4.4% of the global population (366 million individuals) by the year 2030. Glycemic control is a key determinant of long-term outcomes in patients with diabetes, and poor glycemic control is associated with retinopathy, nephropathy and an increased risk of myocardial infarction, cerebrovascular accident, and peripheral vascular disease requiring limb amputation. Despite the development of new insulins and other classes of antidiabetic therapy, roughly half of all patients with diabetes do not achieve recommended target hemoglobin A1c (HbA1c) levels <7.0%.

Frequent self-monitoring of blood glucose (SMBG) is necessary to achieve tight glycemic control in patients with diabetes mellitus, particularly for those requiring insulin therapy. However, current blood (finger-stick) glucose tests are burdensome, and, even in structured clinical studies, patient adherence to the recommended frequency of SMBG decreases substantially over time. Moreover, finger-stick measurements only provide information about a single point in time and do not yield information regarding intraday fluctuations in blood glucose levels that may more closely correlate with some clinical outcomes.

Continuous glucose monitors (CGMs) have been developed in an effort to overcome the limitations of finger-stick SMBG and thereby help improve patient outcomes. These systems enable increased frequency of glucose measurements and a better characterization of dynamic glucose fluctuations, including episodes of unrealized hypoglycemia. Furthermore, integration of CGMs with automated insulin pumps allows for establishment of a closed-loop "artificial pancreas" system to more closely approximate physiologic insulin delivery and to improve adherence.

Monitoring real-time analyte measurements from a living body via wireless analyte monitoring sensor(s) may provide numerous health and research benefits. There is a need to enhance such analyte monitoring systems via innovations comprising, but not limited to, a user interface that enables a user to interact efficiently with an analyte monitoring system.

SUMMARY

One aspect of the invention may provide a display device including a transceiver interface device, a user interface, and a computer. The transceiver interface device may be configured to receive a first raw value corresponding to a first time. The computer may include a non-transitory memory and a processor. The computer may be configured to use at least the first raw value to calculate a first smoothed value corresponding to the first time. The computer may be configured to determine whether the first raw value triggered a first alarm for being above a first threshold value. The computer may be configured to determine whether the first raw value triggered a second alarm for being below a second threshold value. The computer may be configured to, if the first raw value was determined to have triggered the first alarm, determine whether the first smoothed value is not above the first threshold value. The computer may be configured to, if the first raw value was determined to have triggered the second alarm, determine whether the first smoothed value is not below the second threshold value. The computer may be configured to, if the first raw value was determined to have triggered the first alarm and the first smoothed value was determined to be not above the first threshold value, recalculate the first smoothed value to be above the first threshold value. The computer may be configured to, if the first raw value was determined to have triggered the second alarm and the first smoothed value was determined to be not below the second threshold value, recalculate the first smoothed value to be below the second threshold value. The computer may be configured to use the user interface to display a graph including at least the first smoothed value at the first time. The graph may not include the first raw value at the first time.

In some embodiments, a first smoothing algorithm may be used to calculate the first smoothed value, a second smoothing algorithm may be used to recalculate the first smoothed value, and the second smoothing algorithm may be different than the first smoothing algorithm. In some embodiments, a degree of a polynomial used in the second smoothing algorithm may be greater than a degree of a polynomial used in the first smoothing algorithm. In some embodiments, the first smoothing algorithm may fit raw values to a first degree polynomial, and the second smoothing algorithm may fit raw values to a second degree polynomial. In some embodiments, the first smoothing algorithm may fit raw values to a second degree polynomial, and the second smoothing algorithm may fit raw values to a third degree polynomial.

In some embodiments, recalculating the first smoothed value may include recalculating the first smoothed value with smoothing algorithms of increasing polynomial degree until the first smoothed value is above the first threshold value or below the second threshold value. In some embodiments, the transceiver interface device may be further configured to receive a second raw value corresponding to a second time, the second time may be later than the first time, at least the first and second raw values may be used to calculate the first smoothed value corresponding to the first time, and the graph may include the first smoothed value at the first time and the second raw at the second time but does not include the first raw value at the first time.

In some embodiments, the transceiver interface device may be further configured to receive a third raw value corresponding to a third time, which may be later than the second time. The computer may be further configured to use at least the first, second, and third raw values to calculate at least a second smoothed value corresponding to the first time and a third smoothed value corresponding to the second time. The computer may be further configured to, if the first raw value was determined to have triggered the first alarm, determine whether the second smoothed value is not above the first threshold value. The computer may be further configured to, if the first raw value was determined to have triggered the second alarm, determine whether the second smoothed value is not below the second threshold value. The computer may be further configured to determine whether the second raw value triggered the first alarm. The computer may be further configured to determine whether the second raw value triggered the second alarm. The computer may be further configured to, if the second raw value was determined to have triggered the first alarm, determine whether the third smoothed value is not above the first threshold value. The computer may be further configured to, if the second raw value was determined to have triggered the second alarm, determine whether the third smoothed value is not below the second threshold value. The computer may be further configured to, if at least one of the second and third smoothed values (a)(i) corresponds in time to a raw value determined to have triggered the first alarm and (ii) was determined to not be above the first threshold value or (b)(i) corresponds in time to a raw value determined to have triggered the second alarm and (ii) was determined to not be below the second threshold value, recalculate the second and third smoothed values such that (1) none of the second and third smoothed values (i) corresponds in time to a raw value determined to have triggered the first alarm and (ii) is not above the first threshold value and (2) none of the second and third smoothed values (i) corresponds in time to a raw value determined to have triggered the second alarm and (ii) is not below the second threshold value. The computer may be further configured to update the graph by replacing the first smoothed value with the second smoothed value at the first time, by replacing the second raw value with the third smoothed value at the second time, and to include additionally the third raw value at the third time.

In some embodiments, at least the first raw value and one or more previous raw values corresponding to one or more times prior to the first time may be used to calculate the first smoothed value corresponding to the first time and one or more smoothed previous values corresponding to the one or more times prior to the first time. The computer may be further configured to determine whether at least one of the smoothed previous values corresponds in time to a previous raw value that triggered the first alarm. The computer may be further configured to determine whether at least one of the smoothed previous values corresponds in time to a previous raw value that triggered the second alarm. The computer may be further configured to, if at least one of the smoothed previous values was determined to correspond in time to a previous raw value that triggered the first alarm, determine whether the at least one of the smoothed previous values that corresponds in time to a previous raw value that triggered the first alarm is not above the first threshold value. The computer may be further configured to, if at least one of the smoothed previous values was determined to correspond in time to a previous raw value that triggered the second alarm, determine whether the at least one of the smoothed previous values that corresponds in time to a previous raw value that triggered the second alarm is not below the second threshold value. The computer may be further configured to, if at least one of the one or more smoothed previous values (a)(i) corresponds in time to a previous raw value determined to have triggered the first alarm and (ii) was determined to not be above the first threshold value or (b)(i) corresponds in time to a raw value determined to have triggered the second alarm and (ii) was determined to not be below the second threshold value, recalculate the first smoothed value and the one or more smoothed previous values such that (1) none of the first smoothed value and the one or more smoothed previous values (i) corresponds in time to a raw value determined to have triggered the first alarm and (ii) is not above the first threshold value and (2) none of the first smoothed value and the one or more smoothed previous values (i) corresponds in time to a raw value determined to have triggered the second alarm and (ii) is not below the second threshold value; and use the user interface to display in the graph at least the first smoothed value at the first time and the one or more smoothed previous values at the one or more times prior to the first time. The graph may not include the first raw value at the first time.

In some embodiments, the first raw value may trigger the first alarm if (1) the first raw value is above the first threshold value and (2) a previous raw value corresponding to a time that most immediately precedes the first time was not above the first threshold value, and the first raw value may trigger the second alarm if (1) the first raw value is below the second threshold value and (2) the previous raw value corresponding to the time that most immediately precedes the first time was not below the second threshold value.

Another aspect of the invention may provide a method performed by a display device. The method may include receiving a first raw value corresponding to a first time. The method may include using at least the first raw value to calculate a first smoothed value corresponding to the first time. The method may include determining that (a) the first raw value triggered a first alarm for being above a first threshold value and the first smoothed value is not above the first threshold value or (b) the first raw value triggered a second alarm for being below a second threshold value and the first smoothed value is not below the second threshold value. The method may include, in response to determining that (a) the first raw value triggered the first alarm and the first smoothed value is not above the first threshold value or (b) the first raw value triggered the second alarm and the first smoothed value is not below the second threshold value, recalculating the first smoothed value to be (a) above the first threshold value if the first raw value triggered the first alarm or (b) below the second threshold value if the first raw value triggered the second alarm. The method may include using a user interface of the display device to display a graph including at least the first smoothed value at the first time, wherein the graph does not include the first raw value at the first time.

In some embodiments, a first smoothing algorithm may be used to calculate the first smoothed value, a second smoothing algorithm may be used to recalculate the first smoothed value, and the second smoothing algorithm may be different than the first smoothing algorithm. In some embodiments, a degree of a polynomial used in the second smoothing algorithm may be greater than a degree of a polynomial used in the first smoothing algorithm. In some embodiments, the first smoothing algorithm may fit raw values to a first degree polynomial, and the second smoothing algorithm may fit raw values to a second degree polynomial. In some embodiments, the first smoothing algorithm may fit raw values to a second degree polynomial, and the second smoothing algorithm may fit raw values to a third degree polynomial. In some embodiments, recalculating the first smoothed value may include recalculating at least the first smoothed value with smoothing algorithms of increasing polynomial degree until the first smoothed value is above the first threshold value.

In some embodiments, the method may further include receiving a second raw value corresponding to a second time, the second time may be later than the first time; at least the first and second raw values may be used to calculate and re-calculate the first smoothed value corresponding to the first time, and the graph may include the first smoothed value at the first time and the second raw at the second time but may not include the first raw value at the first time. In some embodiments, the method may further include receiving a third raw value corresponding to a third time, which is later than the second time. The method may further include using at least the first, second, and third raw values to calculate at least a second smoothed value corresponding to the first time and a third smoothed value corresponding to the second time. The method may further include determining that at least one of the second and third smoothed values (a)(i) corresponds in time to a raw value that triggered the first alarm and (ii) is not above the first threshold value or (b)(i) corresponds in time to a raw value that triggered the second alarm and (ii) is not below the second threshold value. The method may further include, in response to determining that at least one of the second and third smoothed values (a)(i) corresponds in time to a raw value that triggered the first alarm and (ii) is not above the first threshold value or (b)(i) corresponds in time to a raw value that triggered the second alarm and (ii) is not below the second threshold value, recalculating the second and third smoothed values such that (1) none of the second and third smoothed values (i) corresponds in time to a raw value that triggered the first alarm and (ii) is not above the first threshold value and (2) none of the second and third smoothed values (i) corresponds in time to a raw value that triggered the second alarm and (ii) is not below the second threshold value. The method may further include updating the graph by replacing the first smoothed value with the second smoothed value at the first time, by replacing the second raw value with the third smoothed value at the second time, and to include additionally the third raw value at the third time.

In some embodiments, at least the first raw value and one or more previous raw values corresponding to one or more times prior to the first time may be used to calculate the first smoothed value corresponding to the first time and one or more smoothed previous values corresponding to the one or more times prior to the first time. The method may further include determining that at least one of the one or more smoothed previous values (a)(i) corresponds in time to a previous raw value that triggered the first alarm and (ii) is not above the first threshold value or (b)(i) corresponds in time to a raw value that triggered the second alarm and (ii) is not below the second threshold value. The method may further include, in response to determining that at least one of the one or more smoothed previous values (a)(i) corresponds in time to a previous raw value that triggered the first alarm and (ii) is not above the first threshold value or (b)(i) corresponds in time to a raw value that triggered the second alarm and (ii) is not below the second threshold value, recalculating the first smoothed value and the one or more smoothed previous values such that (1) none of the first smoothed value and the one or more smoothed previous values (i) corresponds in time to a raw value that triggered the first alarm and (ii) is not above the first threshold value and (2) none of the first smoothed value and the one or more smoothed previous values (i) corresponds in time to a raw value that triggered the second alarm and (ii) is not below the second threshold value. The method may further include using the user interface to display in the graph at least the first smoothed value at the first time and the one or more smoothed previous values at the one or more times prior to the first time, and the graph may not include the first raw value at the first time.

In some embodiments, the first raw value may trigger the first alarm if (1) the first raw value is above the first threshold value and (2) a previous raw value corresponding to a time that most immediately precedes the first time was not above the first threshold value, and the first raw value may trigger the second alarm if (1) the first raw value is below the second threshold value and (2) the previous raw value corresponding to the time that most immediately precedes the first time was not below the second threshold value.

Yet another aspect of the invention may provide a display device including a transceiver interface device, a user interface, and a computer. The transceiver interface device may be configured to receive a first raw value corresponding to a first time. The transceiver interface device may be configured to receive a second raw value corresponding to a second time, which is later than the first time. The transceiver interface device may be configured to receive a third raw value corresponding to a third time, which is later than the second time. The transceiver interface device may be configured to receive a fourth raw value corresponding to a fourth time, which is later than the third time. The transceiver interface device may be configured to receive a fifth raw value corresponding to a fifth time, which is later than the fourth time. The computer may include a non-transitory memory and a processor. The computer may be configured to use at least the first, second, third, fourth, and fifth raw values to calculate at least a first smoothed value corresponding to the third time and a second smoothed value corresponding to the fourth time. The computer may be configured to cause the user interface to display a graph including at least the first smoothed value at the third time, the second smoothed value at the fourth time, and the fifth raw value at the fifth time. The graph may include none of the third and fourth raw values at the third and fourth times, respectively.

Still another aspect of the invention may provide a display device including a transceiver interface device, a user interface, and a computer. The transceiver interface device may be configured to receive a first raw value corresponding to a first time; a second raw value corresponding to a second time, which is later than the first time; a third raw value corresponding to a third time, which is later than the second time; a fourth raw value corresponding to a fourth time, which is later than the third time; and a fifth raw value corresponding to a fifth time, which is later than the fourth time. The computer may include a non-transitory memory and a processor. The computer may be configured to use at least the first, second, third, fourth, and fifth raw values to calculate at least a first smoothed value corresponding to the third time and a second smoothed value corresponding to the fourth time. The computer may be configured to cause the user interface to display a graph including at least the first smoothed value at the third time, the second smoothed value at the fourth time, and the fifth raw value at the fifth time, and the graph may include none of the third and fourth raw values at the third and fourth times, respectively.

In some embodiments, the transceiver interface device may be further configured to receive a sixth raw value corresponding to a sixth time, which is later than the fifth time. The computer may be further configured to use at least the second, third, fourth, fifth, and sixth raw values to calculate at least a third smoothed value corresponding to the fourth time and a fourth smoothed value corresponding to the fifth time. The computer may be further configured to update the graph by replacing the second smoothed value at the fourth time with the third smoothed value, by replacing the fifth raw value at the fifth time with the fourth smoothed value, and to include additionally the sixth raw value at the sixth time. In some embodiments, the transceiver interface device may be further configured to receive a seventh raw value corresponding to a seventh time, which is later than the sixth time. The computer may be further configured to use at least the third, fourth, fifth, sixth, and seventh raw values to calculate a fifth smoothed value corresponding to the fifth time and a sixth smoothed value corresponding to the sixth time. The computer may be further configured to update the graph by replacing the fourth smoothed value at the fifth time with the fifth smoothed value, by replacing the sixth raw value at the sixth time with the sixth smoothed value, and to include additionally the seventh raw value at the seventh time.

In some embodiments, using at least the first, second, third, fourth, and fifth raw values to calculate at least the first and second smoothed values may include using a smoothing algorithm to calculate the first and second smoothed values. In some embodiments, the smoothing algorithm may fit raw values to a first degree polynomial. In some embodiments, the smoothing algorithm may fit raw values to a second degree polynomial.

In some embodiments, using at least the first, second, third, fourth, and fifth raw values to calculate the first and second smoothed values may include determining whether at least one of the first and second smoothed values (a)(i) corresponds in time to a raw value that triggered a first alarm for being above a first threshold value and (ii) is not above the first threshold value or (b)(i) corresponds in time to a raw value that triggered a second alarm for being below a second threshold value and (ii) is not below the second threshold value. Using at least the first, second, third, fourth, and fifth raw values to calculate the first and second smoothed values may also include, in response to determining that at least one of the first and second smoothed values (a)(i) corresponds in time to a raw value that triggered the first alarm and (ii) is not above the first threshold value or (b)(i) corresponds in time to a raw value that triggered the second alarm and (ii) is not below the second threshold value, recalculating the first and second smoothed values such that such that (1) none of the first and second smoothed values (i) corresponds in time to a raw value that triggered the first alarm and (ii) is not above the first threshold value and (2) none of the first and second smoothed values (i) corresponds in time to a raw value that triggered the second alarm and (ii) is not below the second threshold value. In some embodiments, a raw value may trigger the first alarm if (1) the raw value is above the first threshold value and (2) a previous raw value corresponding to a time that most immediately precedes the time of the raw value was not above the first threshold value, and the raw value may trigger the second alarm if (1) the raw value is below the second threshold value and (2) the previous raw value was not below the second threshold value.

In some embodiments, the graph may include none of the third and fourth raw values at the third and fourth times, respectively. In some embodiments, the first through fifth raw values may be blood glucose levels.

Another aspect of the invention may provide a method performed by a display device. The method may include receiving a first raw value corresponding to a first time. The method may include receiving a second raw value corresponding to a second time, which is later than the first time. The method may include receiving a third raw value corresponding to a third time, which is later than the second time. The method may include receiving a fourth raw value corresponding to a fourth time, which is later than the third time. The method may include receiving a fifth raw value corresponding to a fifth time, which is later than the fourth time. The method may include using at least the first, second, third, fourth, and fifth raw values to calculate at least a first smoothed value corresponding to the third time and a second smoothed value corresponding to the fourth time. The method may include displaying on a user interface of the display device a graph including at least the first smoothed value at the third time, the second smoothed value at the fourth time, and the fifth raw value at the fifth time.

In some embodiments, the method may further include receiving a sixth raw value corresponding to a sixth time, which is later than the fifth time. The method may further include using at least the second, third, fourth, fifth, and sixth raw values to calculate at least a third smoothed value corresponding to the fourth time and a fourth smoothed value corresponding to the fifth time. The method may further include updating the graph by replacing the second smoothed value at the third time with the third smoothed value, by replacing the fifth raw value at the fifth time with the fourth smoothed value, and to include additionally the sixth raw value at the sixth time. In some embodiments, the method may further include receiving a seventh raw value corresponding to a seventh time, which is later than the sixth time. The method may further include using at least the third, fourth, fifth, sixth, and seventh raw values to calculate at least a fifth smoothed value corresponding to the fifth time and a sixth smoothed value corresponding to the sixth time. The method may further include updating the graph by replacing the fourth smoothed value at the fifth time with the fifth smoothed value, by replacing the sixth raw value at the sixth time with the sixth smoothed value, and to include additionally the seventh raw value at the seventh time.

In some embodiments, using at least the first, second, third, fourth, and fifth raw values to calculate at least the first and second smoothed values may include using a smoothing algorithm to calculate at least the first and second smoothed values. In some embodiments, the smoothing algorithm may fit raw values to a first degree polynomial. In some embodiments, the smoothing algorithm may fit raw values to a second degree polynomial. In some embodiments, using at least the first, second, third, fourth, and fifth raw values to calculate at least the first and second smoothed values may include determining that at least one of the first and second smoothed values (a)(i) corresponds in time to a raw value that triggered a first alarm for being above a first threshold value and (ii) is not above the first threshold value or (b)(i) corresponds in time to a raw value that triggered a second alarm for being below a second threshold value and (ii) is not below the second threshold value. Using at least the first, second, third, fourth, and fifth raw values to calculate at least the first and second smoothed values may also include, in response to determining that at least one of the first and second smoothed values (a)(i) corresponds in time to a raw value that triggered the first alarm and (ii) is not above the first threshold value or (b)(i) corresponds in time to a raw value that triggered the second alarm and (ii) is not below the second threshold value, recalculating at least the first and second smoothed values such that such that (1) none of the first and second smoothed values (i) corresponds in time to a raw value that triggered the first alarm and (ii) is not above the first threshold value and (2) none of the first and second smoothed values (i) corresponds in time to a raw value that triggered the second alarm and (ii) is not below the second threshold value. In some embodiments, a raw value may trigger the first alarm if (1) the raw value is above the first threshold value and (2) a previous raw value corresponding to a time that most immediately precedes the time of the raw value was not above the first threshold value, and the raw value may trigger the second alarm if (1) the raw value is below the second threshold value and (2) the previous raw value was not below the second threshold value.

In some embodiments, the graph may include none of the third and fourth raw values at the third and fourth times, respectively. In some embodiments, the first through fifth raw values may be blood glucose levels.

Further variations encompassed within the systems and methods are described in the detailed description of the invention below.

BRIEF DESCRIPTION OF THE DRAWINGS

The accompanying drawings, which are incorporated herein and form part of the specification, illustrate various, non-limiting embodiments of the present invention. In the drawings, like reference numbers indicate identical or functionally similar elements.

DETAILED DESCRIPTION OF PREFERRED EMBODIMENTS

Figure 1:
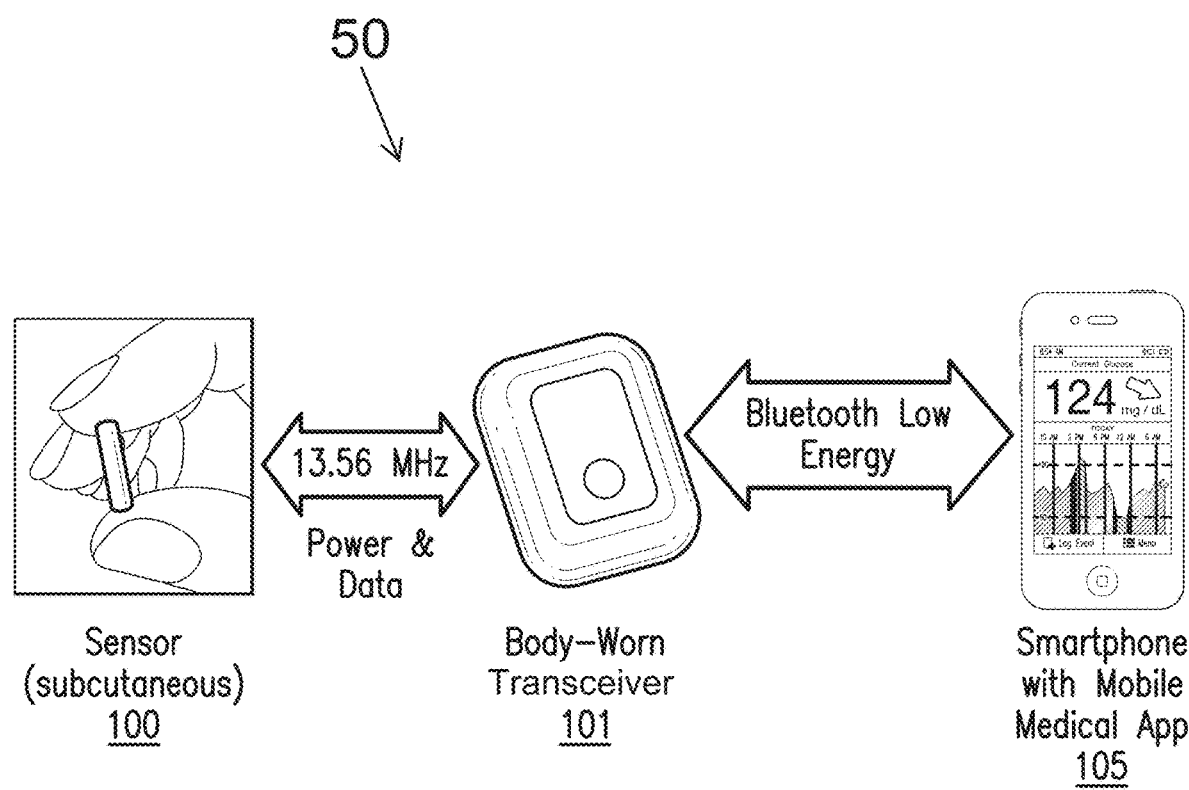
FIG. 1 is a schematic view illustrating an analyte monitoring system embodying aspects of the present invention.

FIG. 1 is a schematic view of an exemplary analyte monitoring system 50 embodying aspects of the present invention. The analyte monitoring system 50 may be a continuous analyte monitoring system (e.g., a continuous glucose monitoring system). In some embodiments, the analyte monitoring system 50 may include one or more of an analyte sensor 100, a transceiver 101, and a display device 105. In some embodiments, the sensor 100 may be small, fully subcutaneously implantable sensor. However, this is not required, and, in some alternative embodiments, the sensor 100 may be a partially implantable (e.g., transcutaneous) sensor or a fully external sensor.

In some embodiments, the transceiver 101 may be an externally worn transceiver (e.g., attached via an armband, wristband, waistband, or adhesive patch). In some embodiments, the transceiver 101 may communicate with the sensor to initiate and receive one or more sensor measurements via a wireless connection (e.g., via near field communication (NFC)) or a wired connection. In some embodiments, the sensor measurements may include one or more light measurements and/or one or more temperature measurements. In some embodiments, the one or more sensor measurements may be indicative of an amount or concentration of an analyte in a medium (e.g., interstitial fluid) of a living animal (e.g., a living human). In some embodiments, the transceiver 101 may calculate one or more analyte concentrations using at least the received sensor measurements.

In some embodiments, the transceiver 101 may communicate information (e.g., one or more analyte concentrations) wirelessly (e.g., via a Bluetooth™ communication standard such as, for example and without limitation Bluetooth Low Energy) to a mobile medical application (MMA) running on a display device 105 (e.g., a smartphone or tablet). In some embodiments, the MMA may additionally or alternatively receive the information receive the information from the transceiver 101 through a wired connection (e.g., using a Universal Serial Bus (USB)) port. In some embodiments, the analyte monitoring system 50 may include a web interface for plotting and sharing of the received information.

Figure 2:
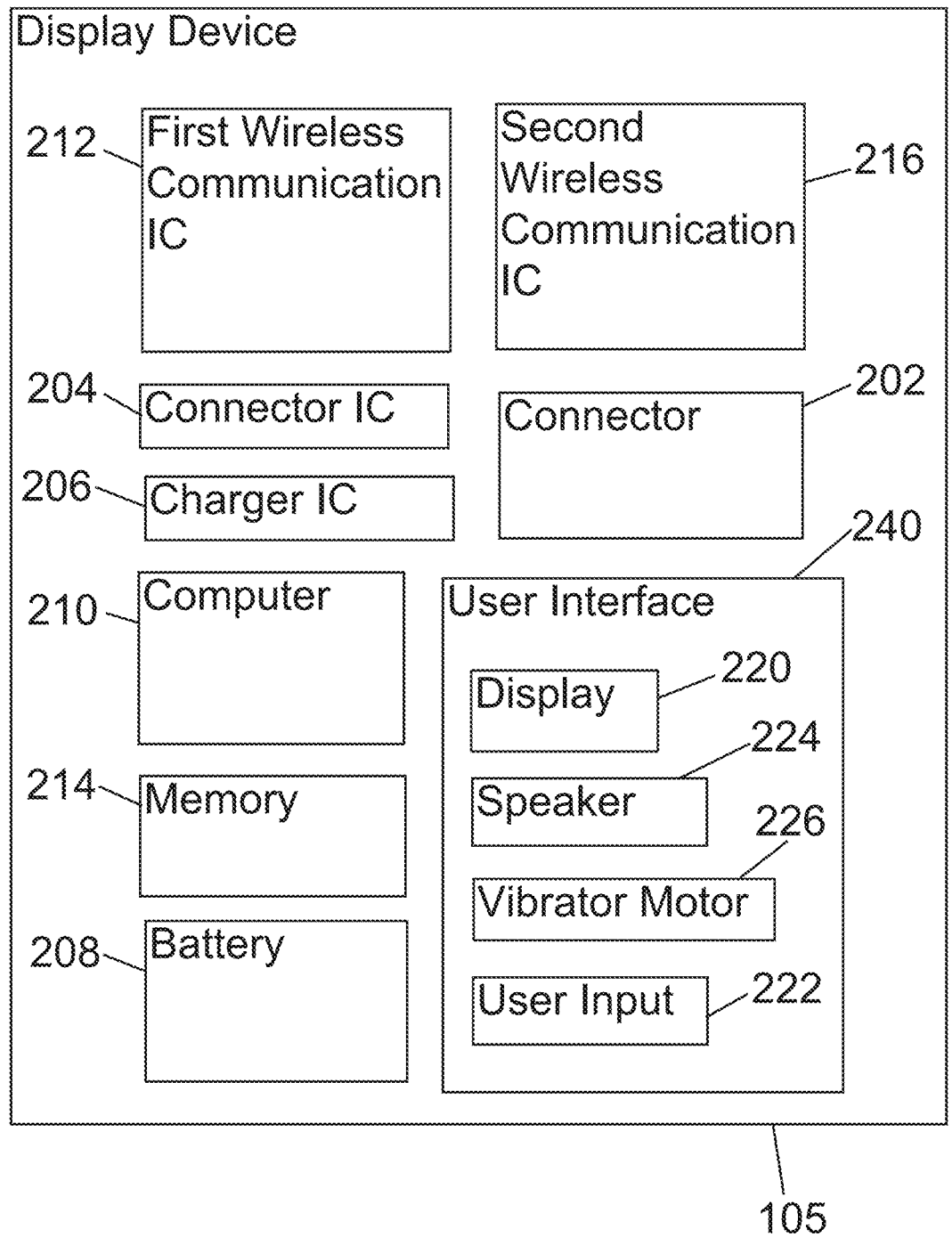
FIG. 2 illustrates a block diagram of a display device of the analyte monitoring system according to some embodiments.

FIG. 2 is a block diagram of a non-limiting embodiment of the display device 105 of the analyte monitoring system 50. As shown in FIG. 2, in some embodiments, the display device 105 may include one or more of a connector 202, a connector integrated circuit (IC) 204, a charger IC 206, a battery 208, a computer 210, a first wireless communication IC 212, a memory 214, a second wireless communication IC 216, and a user interface 240.

In some embodiments in which the display device 105 includes the connector 202, the connector 202 may be, for example and without limitation, a Micro-Universal Serial Bus (USB) connector. The connector 202 may enable a wired connection to an external device, such as a personal computer or transceiver 101. The display device 105 may exchange data to and from the external device through the connector 202 and/or may receive power through the connector 202. In some embodiments, the connector IC 204 may be, for example and without limitation, a USB-IC, which may control transmission and receipt of data through the connector 202.

In some embodiments in which the display device 105 includes the charger IC 206, the charger IC 206 may receive power via the connector 202 and charge the battery 208. In some embodiments, the battery 208 may be, for example and without limitation, a lithium-polymer battery. In some embodiments, the battery 208 may be rechargeable, may have a short recharge duration, and/or may have a small size.

In some embodiments, the display device 105 may include one or more connectors and/or one or more connector ICs in addition to (or as an alternative to) connector 202 and connector IC 204. For example, in some alternative embodiments, the display device 105 may include a spring-based connector (e.g., Pogo pin connector) in addition to (or as an alternative to) connector 202, and the display device 105 may use a connection established via the spring-based connector for wired communication to a personal computer or the transceiver 101 and/or to receive power, which may be used, for example, to charge the battery 208.

In some embodiments in which the display device 105 includes the first wireless communication IC 212, the first wireless communication IC 212 may enable wireless communication with one or more external devices, such as, for example, one or more personal computers, one or more transceivers 101, and/or one or more other display devices 105. In some embodiments, the first wireless communication IC 212 may employ one or more wireless communication standards to wirelessly transmit data. The wireless communication standard employed may be any suitable wireless communication standard, such as an ANT standard, a Bluetooth standard, or a Bluetooth Low Energy (BLE) standard (e.g., BLE 4.0). In some embodiments, the first wireless communication IC 212 may be configured to wirelessly transmit data at a frequency greater than 1 gigahertz (e.g., 2.4 or 5 GHz). In some embodiments, the first wireless communication IC 212 may include an antenna (e.g., a Bluetooth antenna). In some embodiments, the antenna of the first wireless communication IC 212 may be entirely contained within a housing of the display device 105. However, this is not required, and, in alternative embodiments, all or a portion of the antenna of the first wireless communication IC 212 may be external to the display device housing.

In some embodiments, the display device 105 may include a transceiver interface device, which may enable communication by the display device 105 with one or more transceivers 101. In some embodiments, the transceiver interface device may include the antenna of the first wireless communication IC 212 and/or the connector 202. In some embodiments, the transceiver interface device may additionally or alternatively include the first wireless communication IC 212 and/or the connector IC 204.

In some embodiments in which the display device 105 includes the second wireless communication IC 216, the second wireless communication IC 216 may enable the display device 105 to communicate with one or more remote devices (e.g., smartphones, servers, and/or personal computers) via wireless local area networks (e.g., Wi-Fi), cellular networks, and/or the Internet. In some embodiments, the second wireless communication IC 216 may employ one or more wireless communication standards to wirelessly transmit data. In some embodiments, the second wireless communication IC 216 may include one or more antennas (e.g., a Wi-Fi antenna and/or one or more cellular antennas). In some embodiments, the one or more antennas of the second wireless communication IC 216 may be entirely contained within a housing of the display device 105. However, this is not required, and, in alternative embodiments, all or a portion of the one or more antennas of the second wireless communication IC 216 may be external to the display device housing.

In some embodiments in which the display device 105 includes the memory 214, the memory 214 may be non-volatile and/or capable of being electronically erased and/or rewritten. In some embodiments, the memory 214 may be, for example and without limitations a Flash memory.

In some embodiments in which the display device 105 includes the computer 210, the computer 210 may control the overall operation of the display device 105. For example, the computer 210 may control the connector IC 204, the first wireless communication IC 212, and/or the second wireless communication IC 216 to transmit data via wired or wireless communication. The computer 210 may additionally or alternatively control processing of received data (e.g., analyte monitoring data received from the transceiver 101).

In some embodiments in which the display device 105 includes the user interface 240, the user interface 240 may include one or more of a display 220 and a user input 222. In some embodiments, the display 220 may be a liquid crystal display (LCD) and/or light emitting diode (LED) display. In some embodiments, the user input 222 may include one or more buttons, a keyboard, a keypad, and/or a touchscreen. In some embodiments, the computer 210 may control the display 220 to display data (e.g., analyte concentration values, analyte trend information, alerts, alarms, and/or notifications). In some embodiments, the user interface 240 may include one or more of a speaker 224 (e.g., a beeper) and a vibration motor 226, which may be activated, for example, in the event that a condition (e.g., a hypoglycemic or hyperglycemic condition) is met.

In some embodiments, the computer 210 may execute a mobile medical application (MMA). In some embodiments, the display device 105 may receive analyte monitoring data from the transceiver 101. The received analyte monitoring data may include one or more analyte concentrations, one or more analyte concentrations trends, and/or one or more sensor measurements. The received analyte monitoring data may additionally or alternatively include alarms, alerts, and/or notifications. The MMA may display some or all of the received analyte monitoring data on the display 220 of the display device 105.

In some embodiments, the analyte monitoring system 50 may calibrate the conversion of raw sensor measurements to analyte concentrations. In some embodiments, the calibration may be performed approximately periodically (e.g., every 12 or 24 hours). In some embodiments, the calibration may be performed using one or more reference measurements (e.g., one or more self-monitoring blood glucose (SHBG) measurements). In some embodiments, the reference measurements may be entered into the analyte monitoring system 50 using the user interface 240 of the display device 105. In some embodiments, the display device 105 may convey one or more references measurements to the transceiver 101, and the transceiver 101 may use the one or more received reference measurements to perform the calibration.

Figure 3:
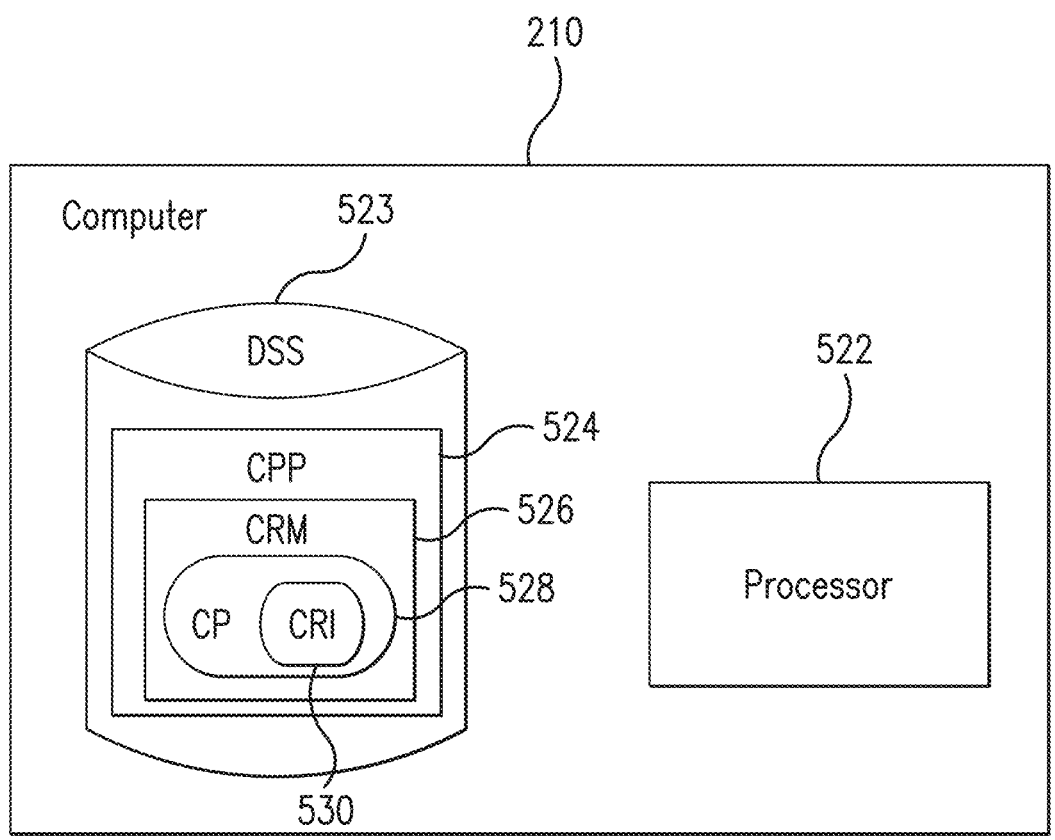
FIG. 3 illustrates a block diagram of a computer of the display device of the analyte monitoring system according to some embodiments.

FIG. 3 is a block diagram of a non-limiting embodiment of the computer 210 of the analyte monitoring system 50. As shown in FIG. 3, in some embodiments, the computer 210 may include one or more processors 522 (e.g., a general purpose microprocessor) and/or one or more circuits, such as an application specific integrated circuit (ASIC), field-programmable gate arrays (FPGAs), a logic circuit, and the like. In some embodiments, the computer 210 may include a data storage system (DSS) 523. The DSS 523 may include one or more non-volatile storage devices and/or one or more volatile storage devices (e.g., random access memory (RAM)). In embodiments where the computer 210 includes a processor 522, the DSS 523 may include a computer program product (CPP) 524. CPP 524 may include or be a computer readable medium (CRM) 526. The CRM 526 may store a computer program (CP) 528 comprising computer readable instructions (CRI) 530. In some embodiments, the CRM 526 may store, among other programs, the MMA, and the CRI 530 may include one or more instructions of the MMA. The CRM 526 may be a non-transitory computer readable medium, such as, but not limited, to magnetic media (e.g., a hard disk), optical media (e.g., a DVD), solid state devices (e.g., random access memory (RAM) or flash memory), and the like. In some embodiments, the CRI 530 of computer program 528 may be configured such that when executed by processor 522, the CRI 530 causes the computer 210 to perform steps described below (e.g., steps described below with reference to the MMA). In other embodiments, the computer 210 may be configured to perform steps described herein without the need for a computer program. That is, for example, the computer 210 may consist merely of one or more ASICs. Hence, the features of the embodiments described herein may be implemented in hardware and/or software.

In some embodiments in which the user interface 240 of the display device 105 includes the display 218, the MMA may cause the display device 105 to provide a series of graphical control elements or widgets in the user interface 240, such as a graphical user interface (GUI), shown on the display 218. The MMA may, for example without limitation, cause the display device 105 to display analyte related information in a GUI such as, but not limited to: one or more of analyte information, current analyte concentrations, past analyte concentrations, predicted analyte concentrations, user notifications, analyte status alerts and alarms, trend graphs, arrows, and user-entered events. In some embodiments, the MMA may provide one or more graphical control elements that may allow a user to manipulate aspects of the one or more display screens. Although aspects of the MMA are illustrated and described in the context of glucose monitoring system embodiments, this is not required, and, in some alternative embodiments, the MMA may be employed in other types of analyte monitoring systems.

In some embodiments where the display device 105 communicates with a transceiver 101, which in turn obtains sensor measurement data from the analyte sensor 100, the MMA may cause the display device 105 to receive and display one or more of glucose data, trends, graphs, alarms, and alerts from the transceiver 101. In some embodiments, device 105 to access the Android App Store to download a MMA compatible with the Android OS.

Figure 4:
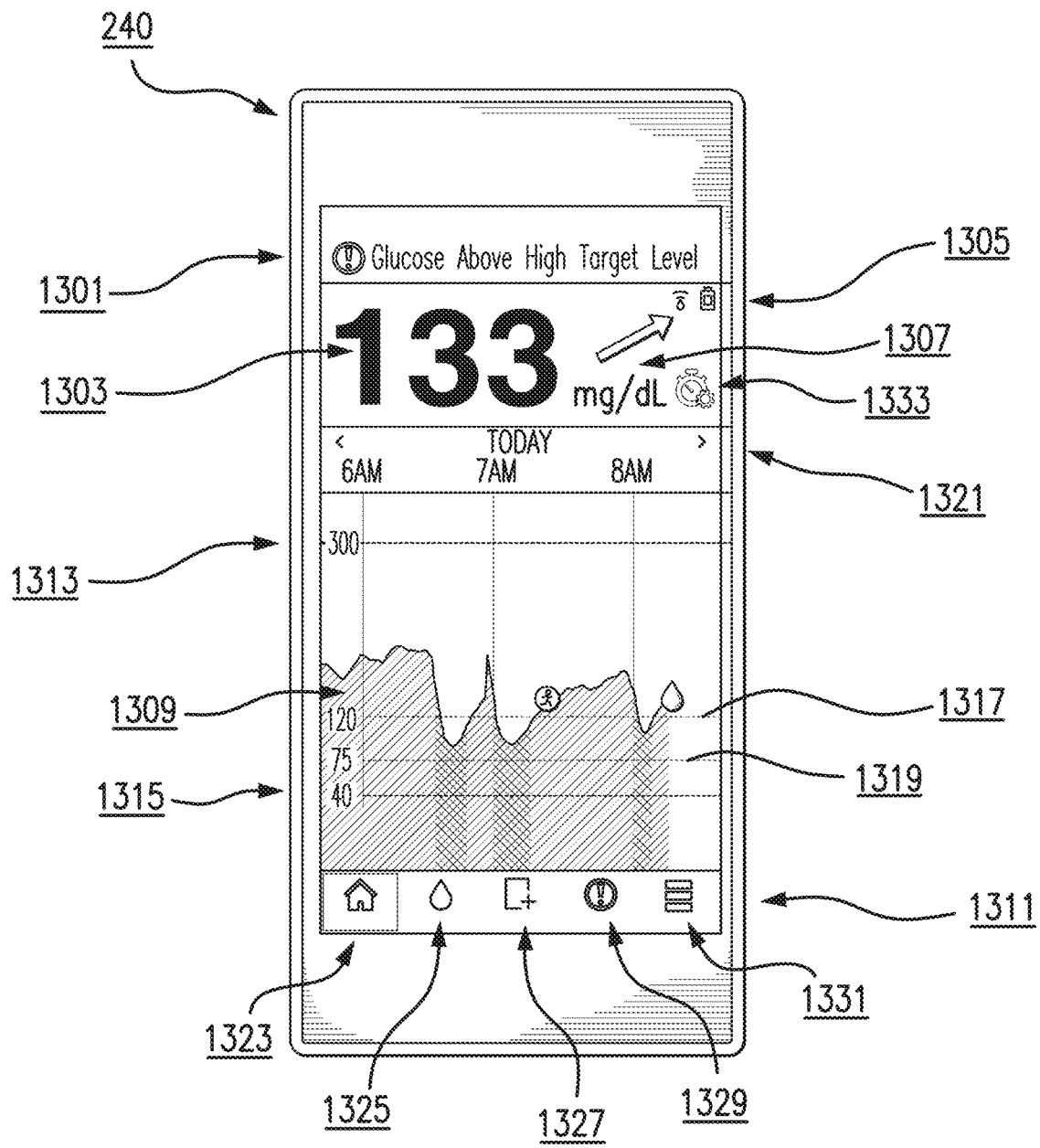
FIG. 4 illustrates a non-limiting example of a home screen illustrative display of a medical mobile application according to some embodiments.
Figure 5B:
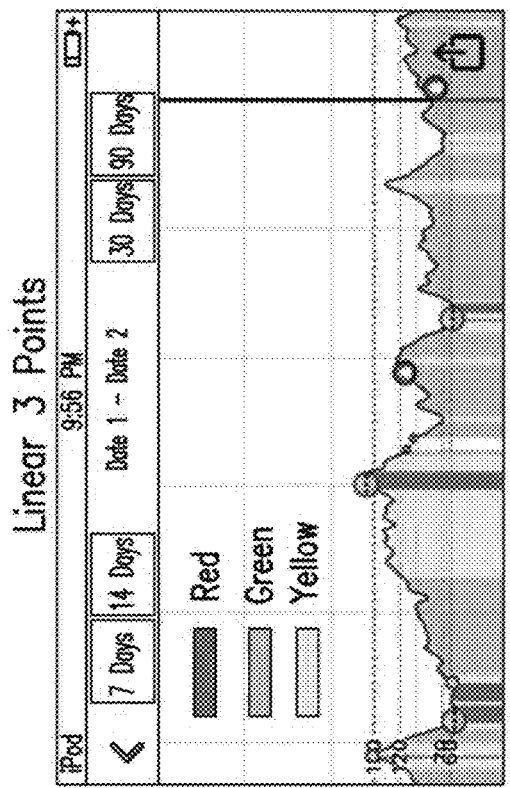
FIGS. 5A-18H illustrate non-limiting examples of raw values and corresponding smoothed values according to some embodiments.
Figure 5D:
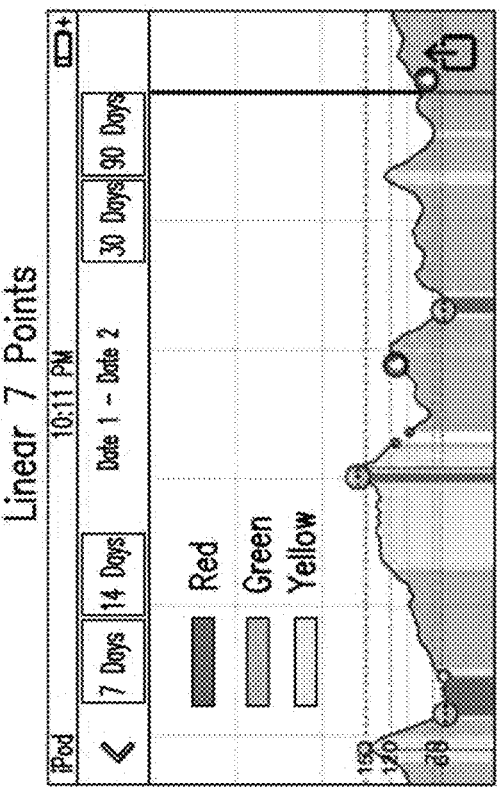
Figure 5A:
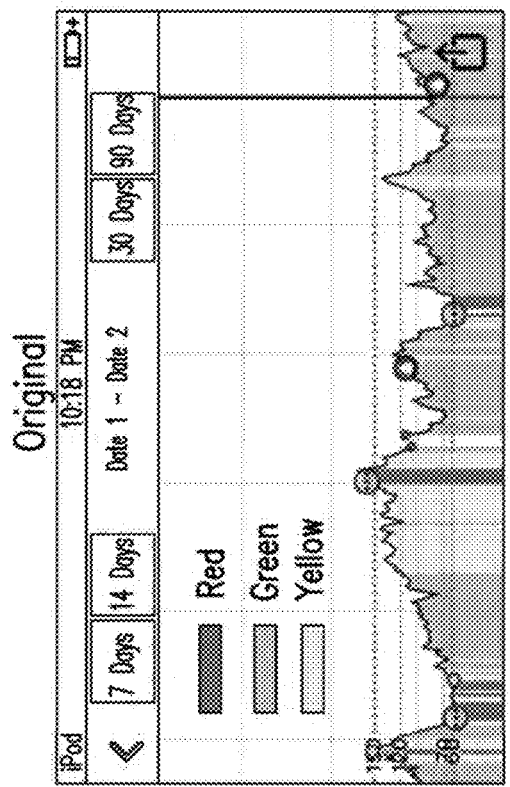
Figure 5C:
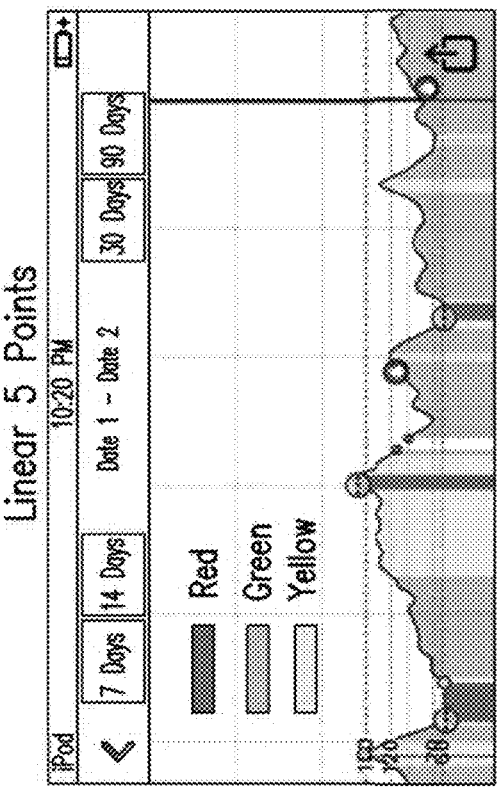
Figure 5E:
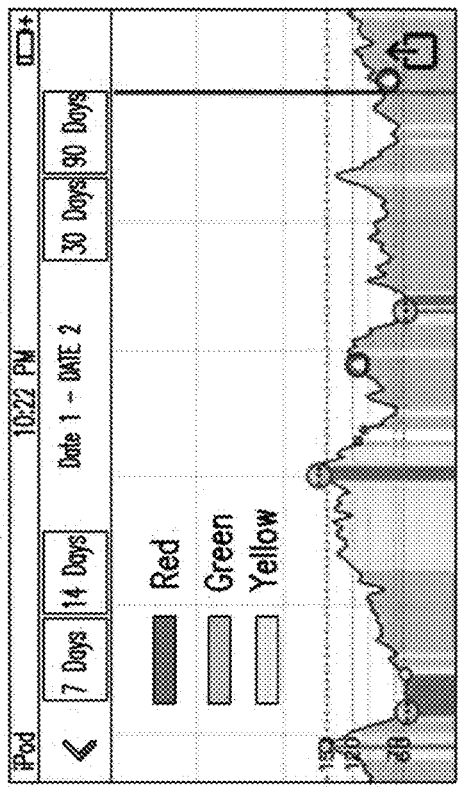
Figure 5F:
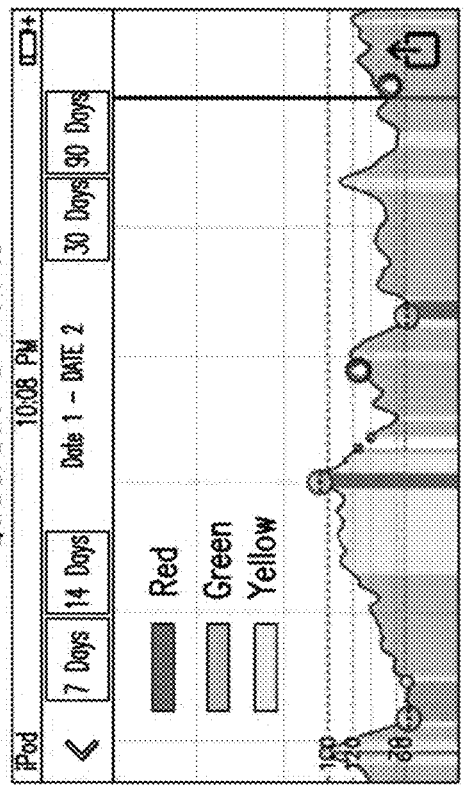
Figure 5G:
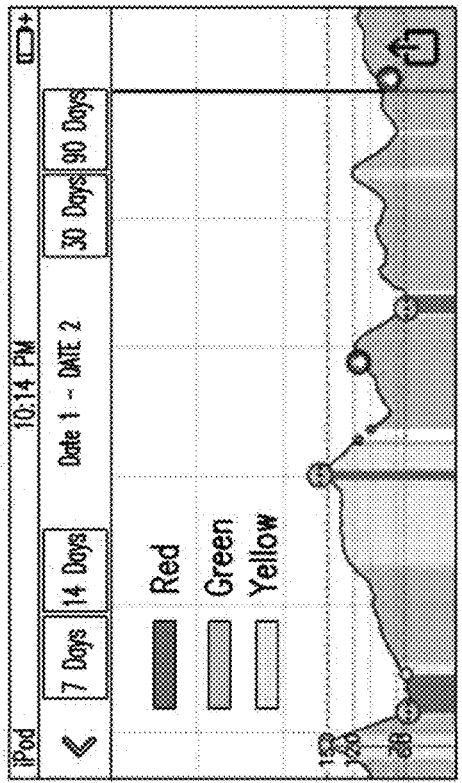
Figure 5H:
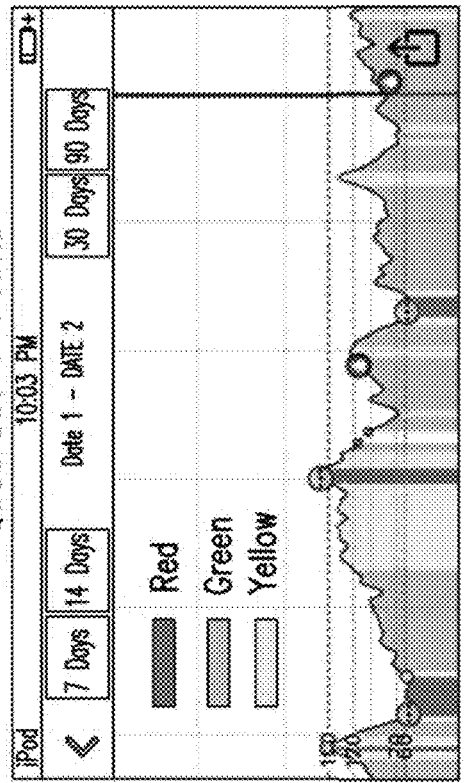
Figure 6A:
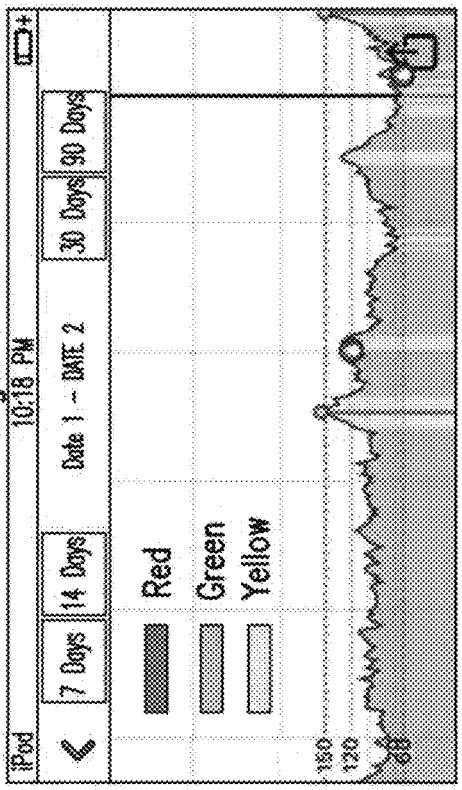
Figure 6B:
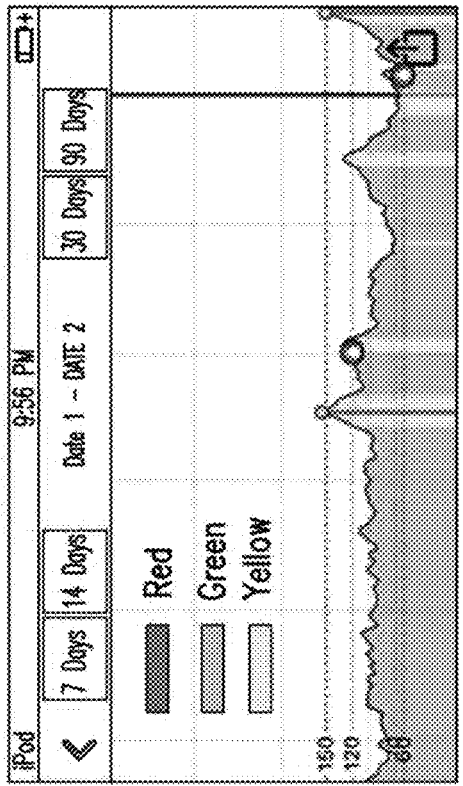
Figure 6C:
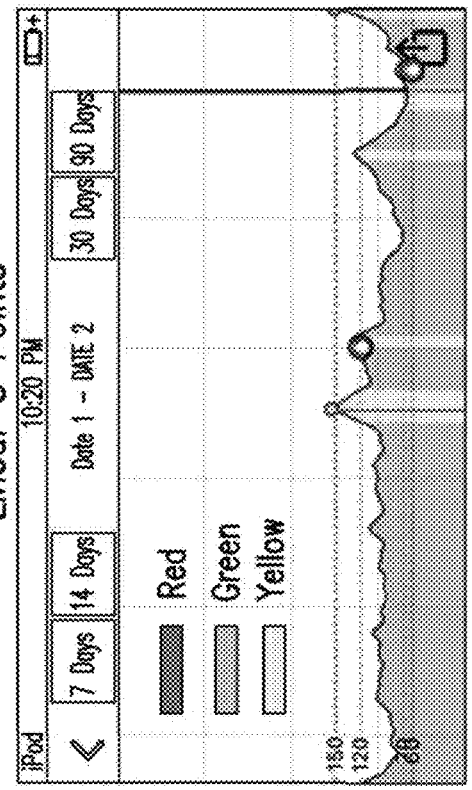
Figure 6D:
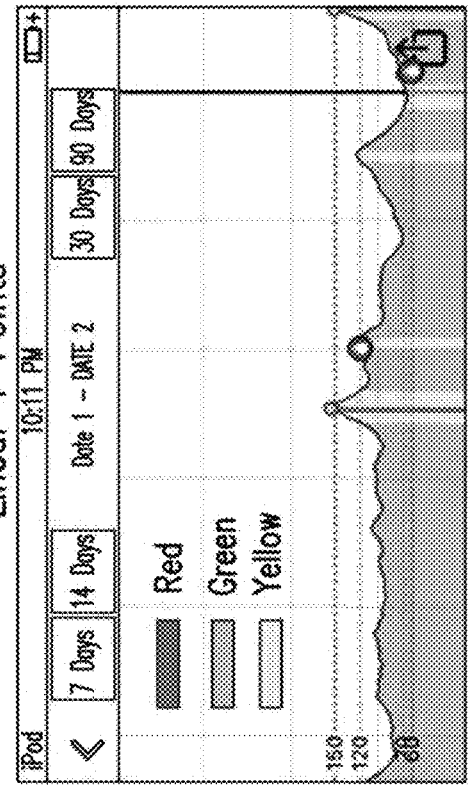
Figure 6E:
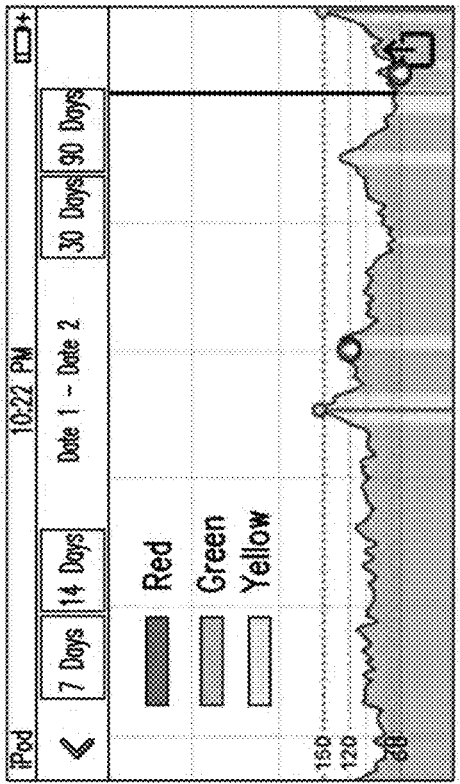
Figure 6F:
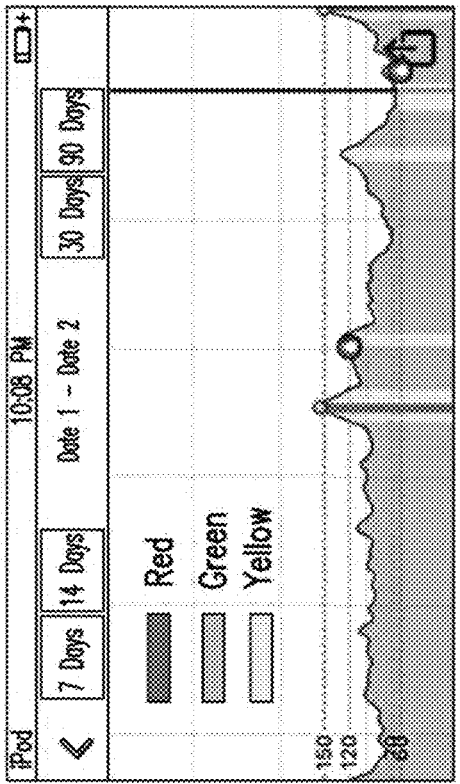
Figure 6G:
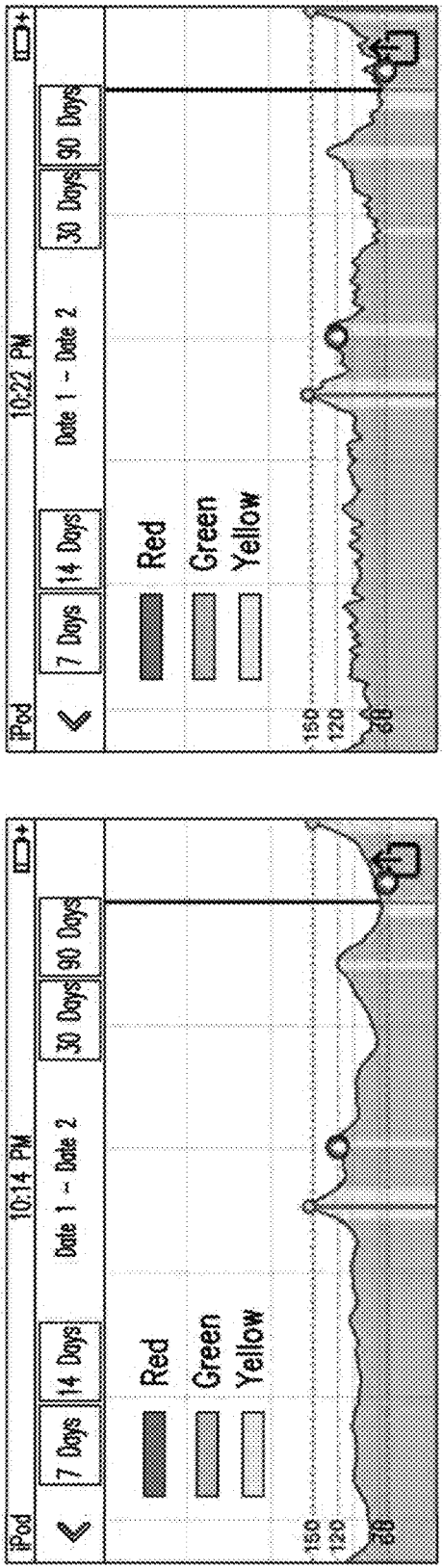
Figure 6H:
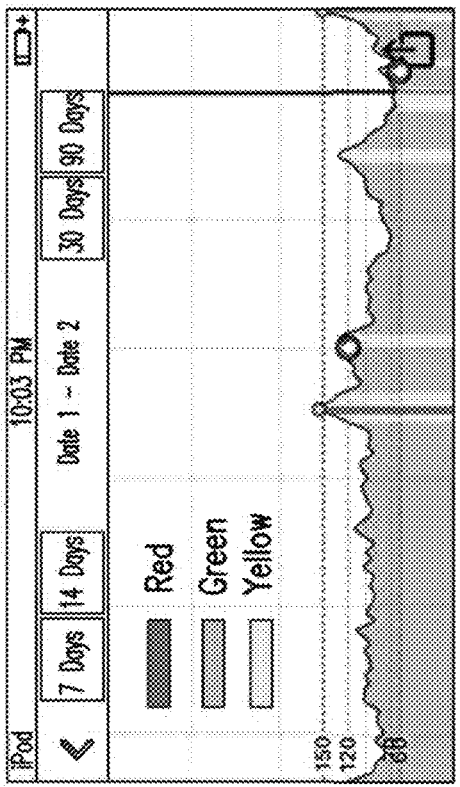
Figure 7A:
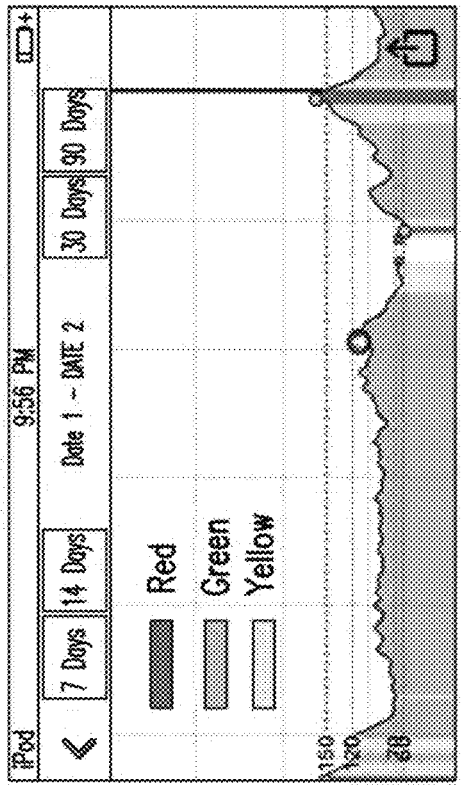
Figure 7B:
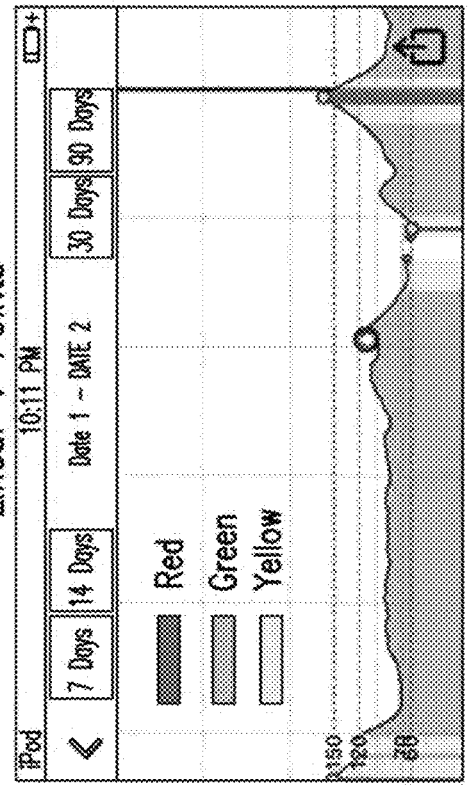
Figure 7C:
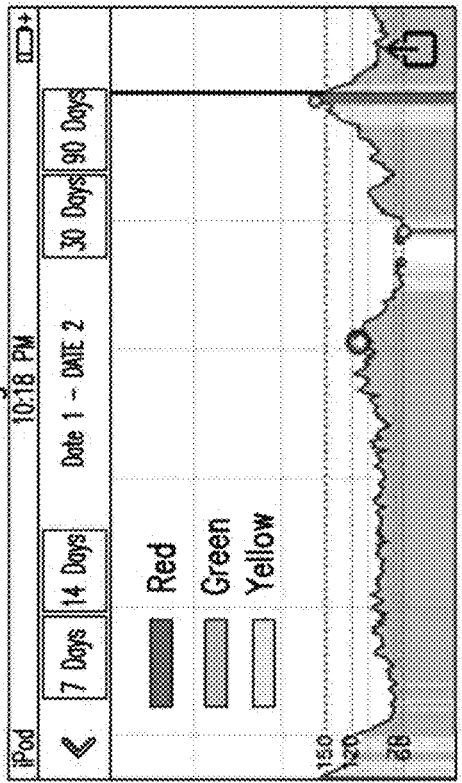
Figure 7D:
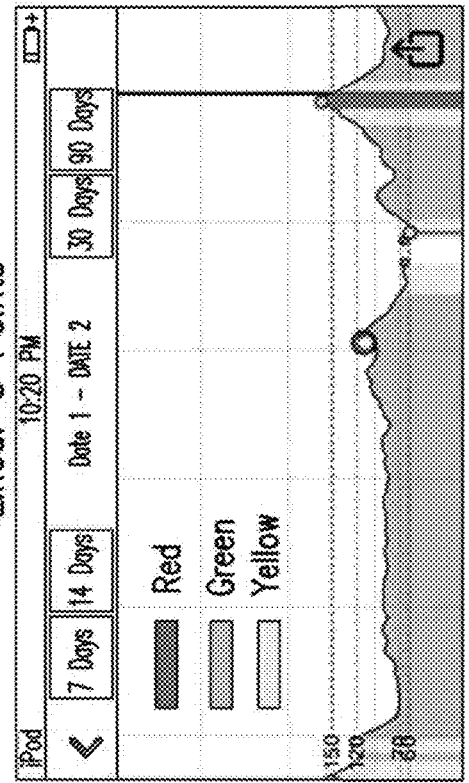
Figure 7E:
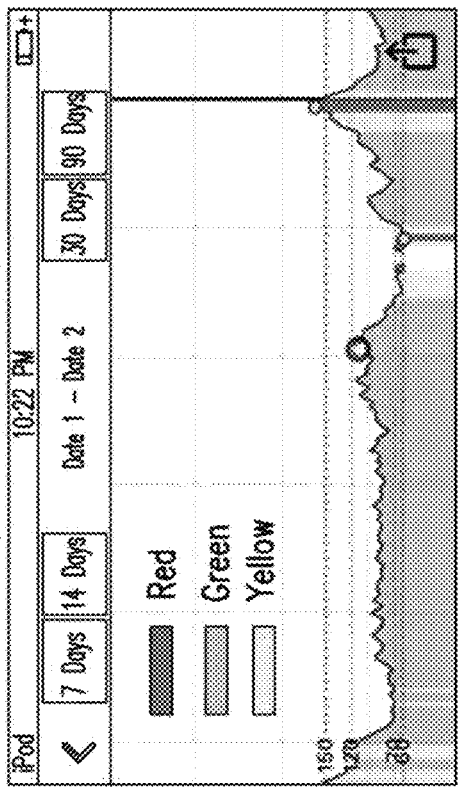
Figure 7F:
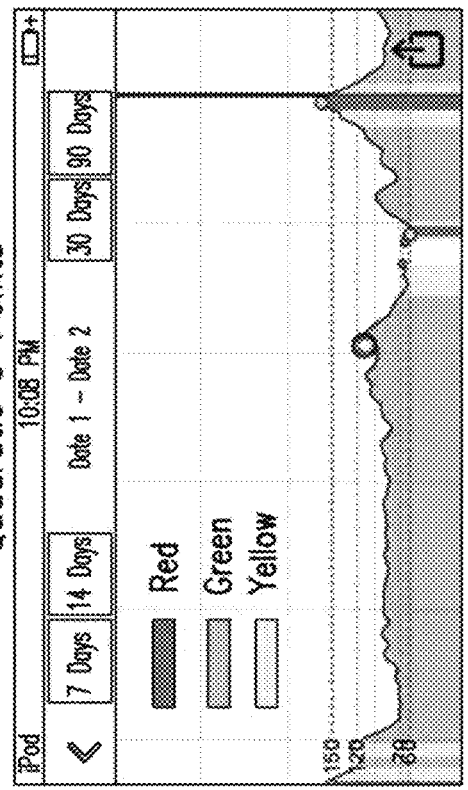
Figure 7G:
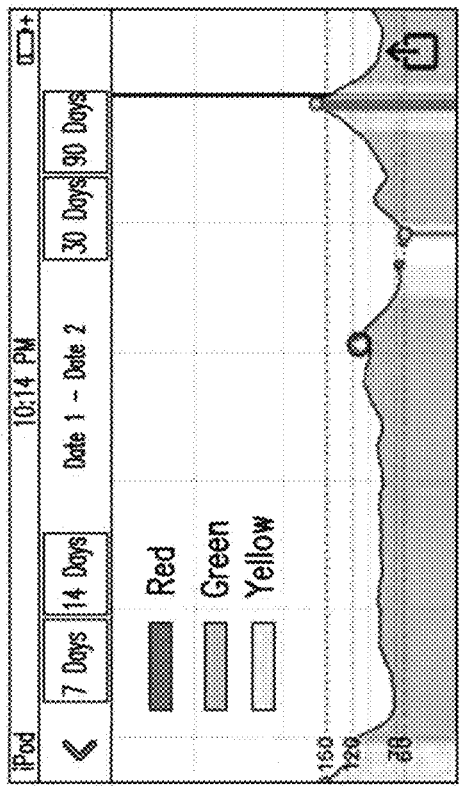
Figure 7H:
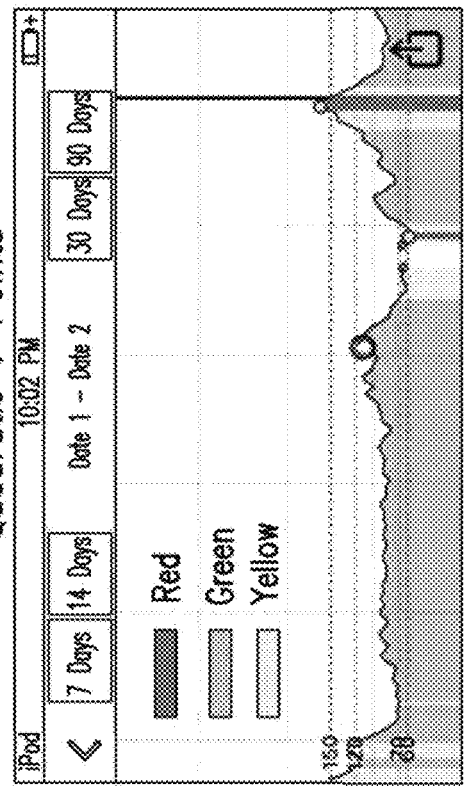
Figure 8A:
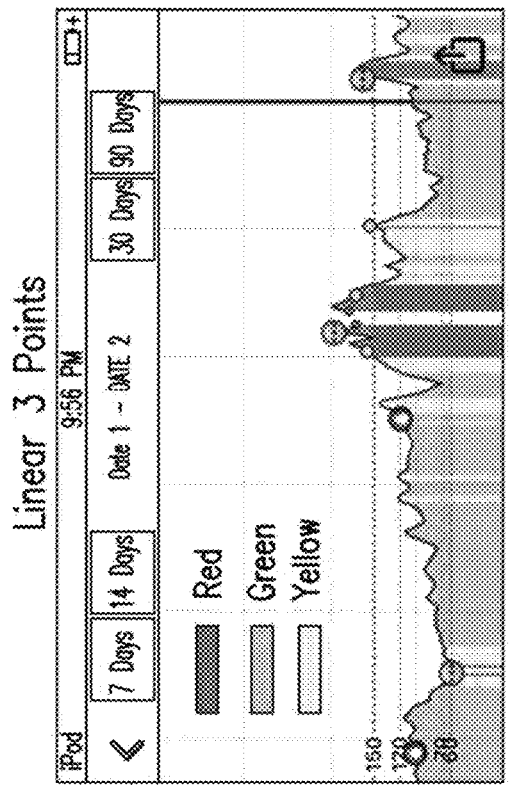
Figure 8B:
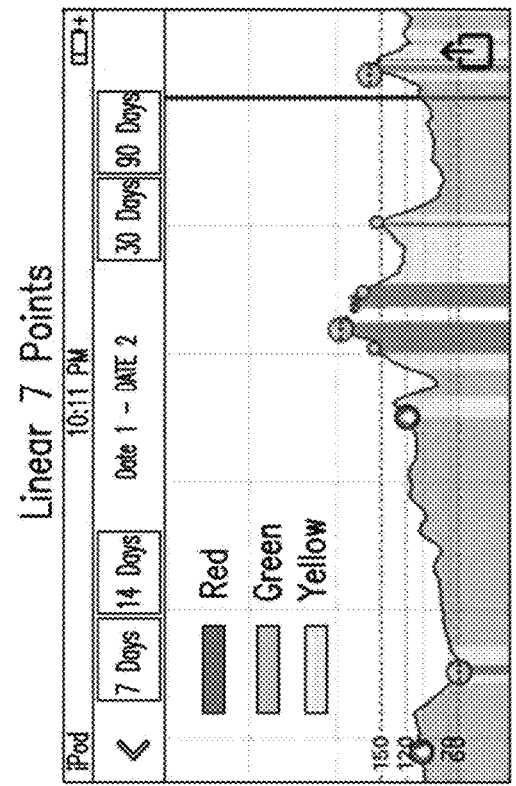
Figure 8C:
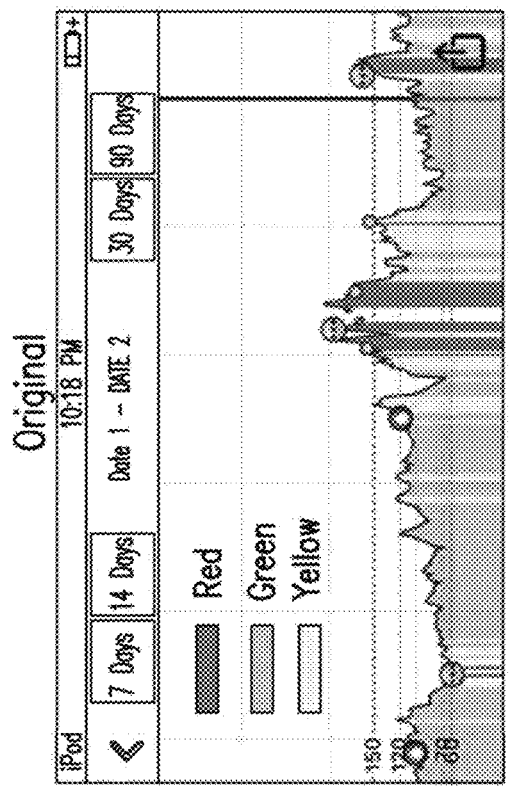
Figure 8D:
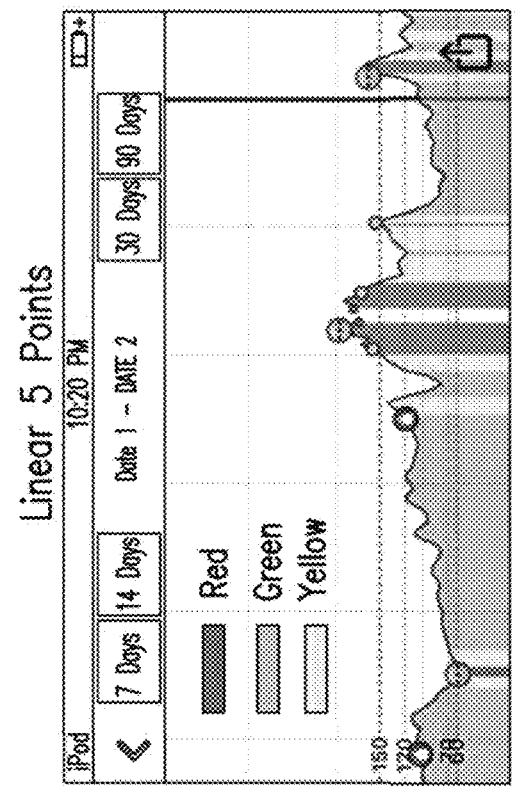
Figure 8E:
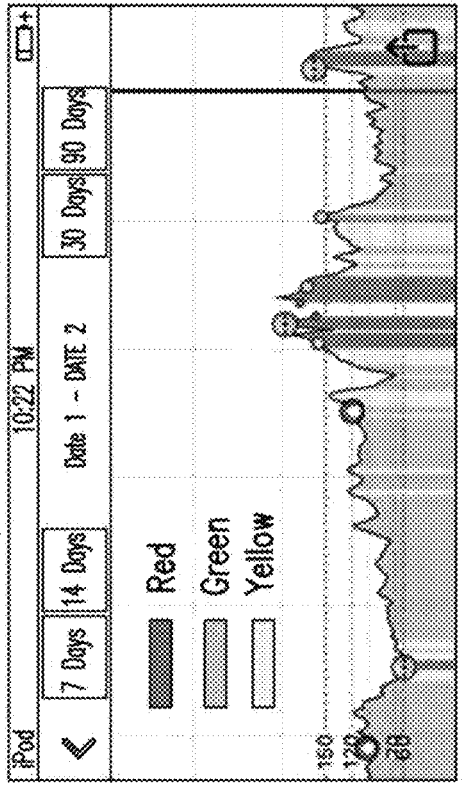
Figure 8F:
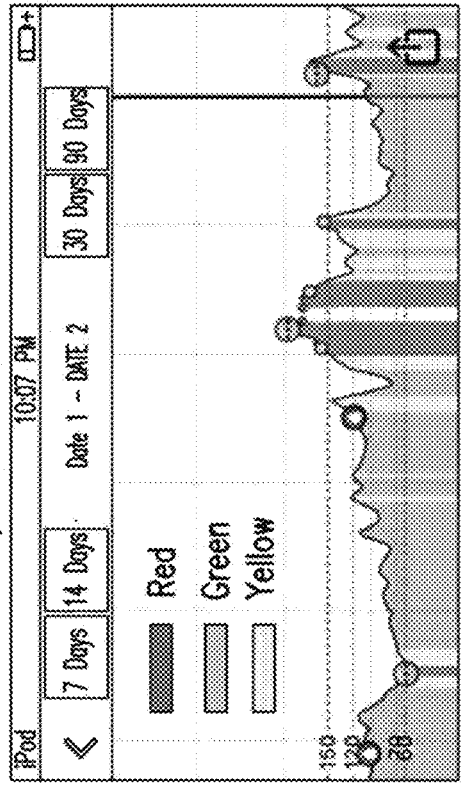
Figure 8G:
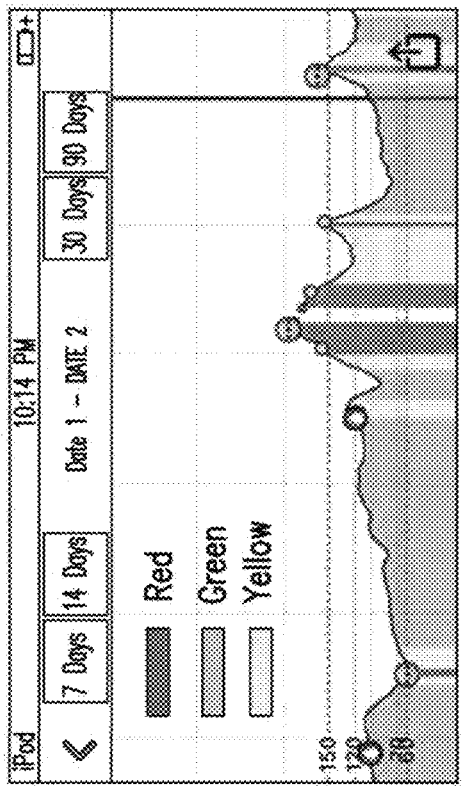
Figure 8H:
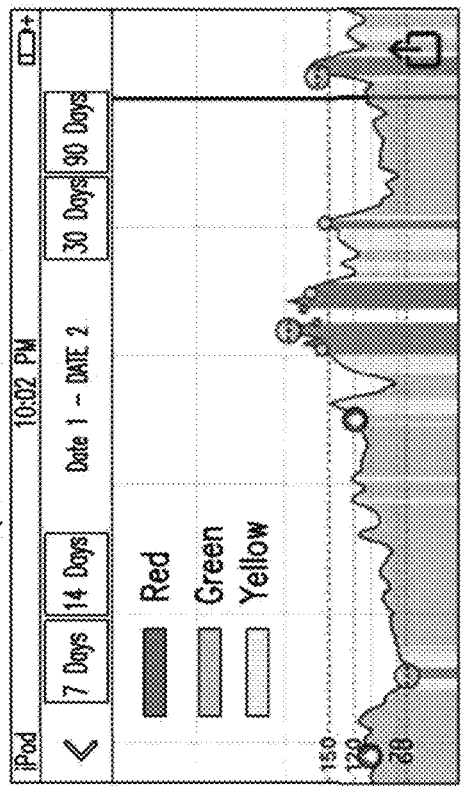
Figure 9A:
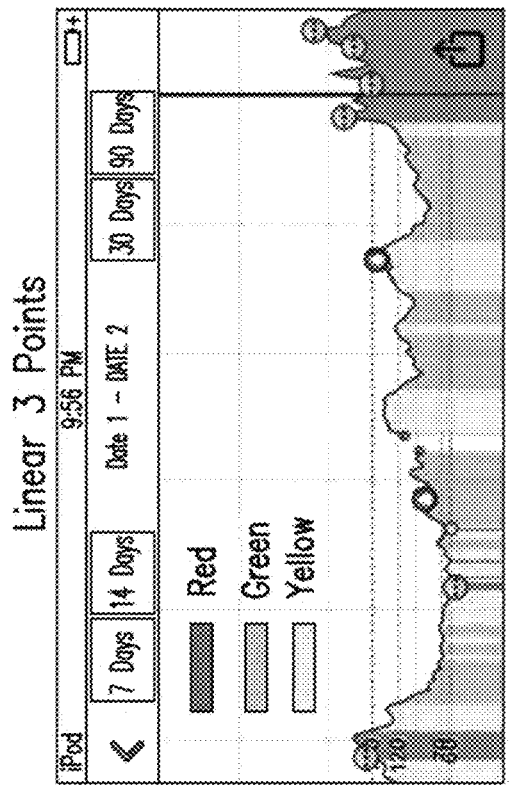
Figure 9B:
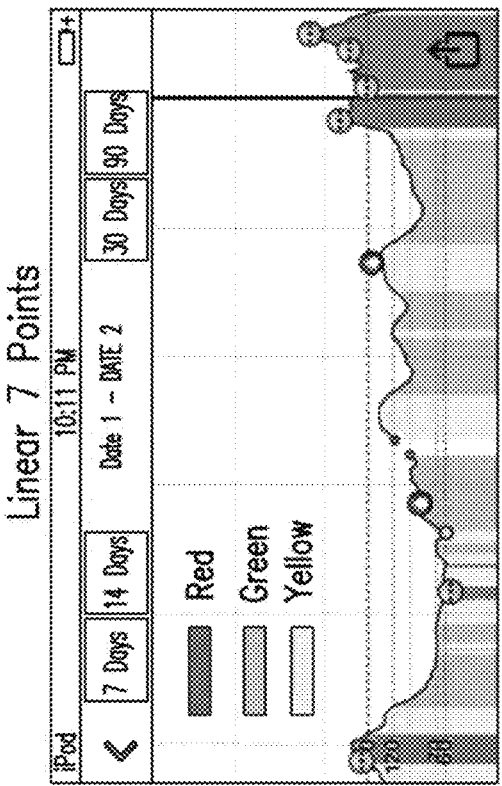
Figure 9C:
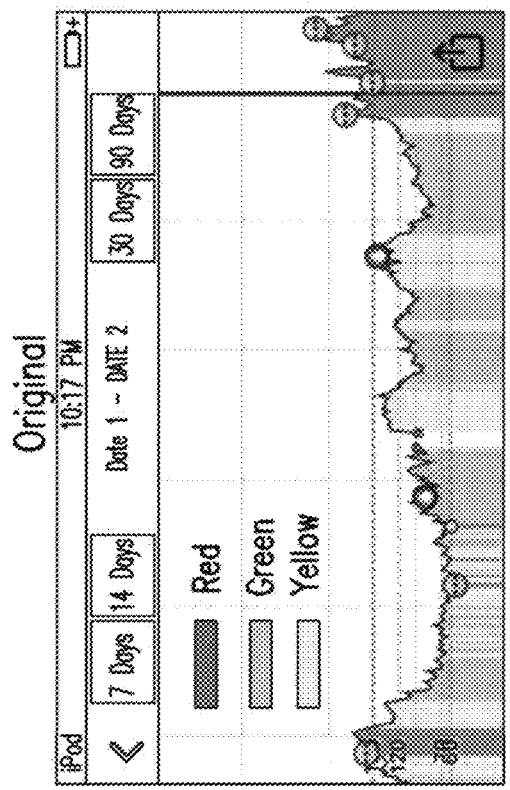
Figure 9D:
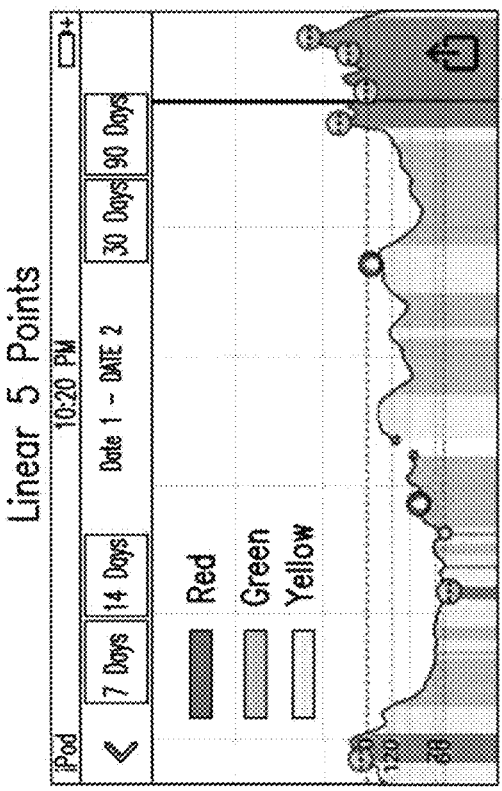
Figure 9E:
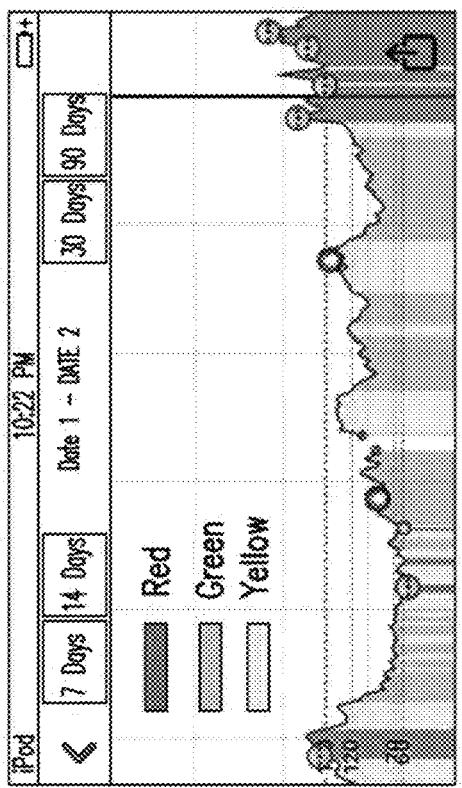
Figure 9F:
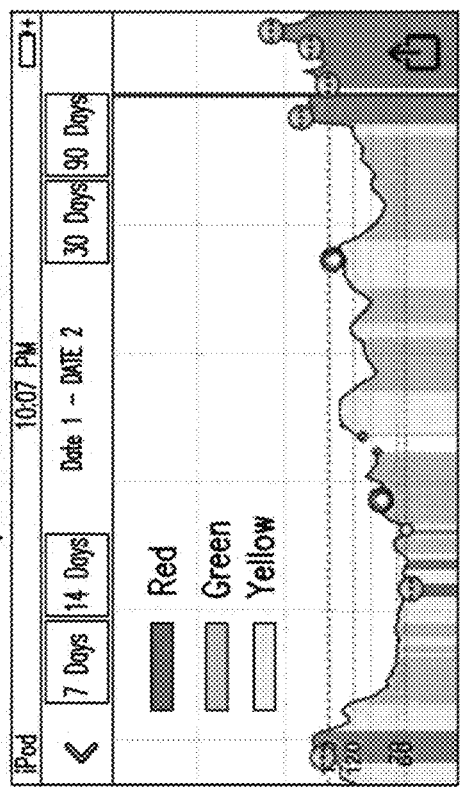
Figure 9G:
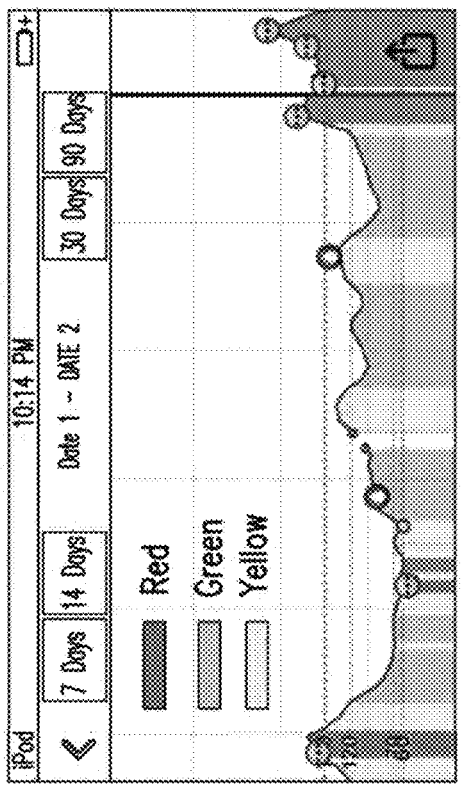
Figure 9H:
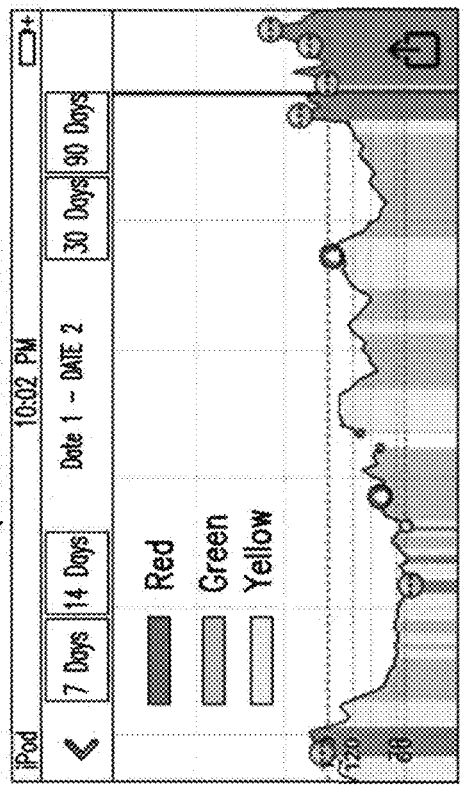
Figure 10A:
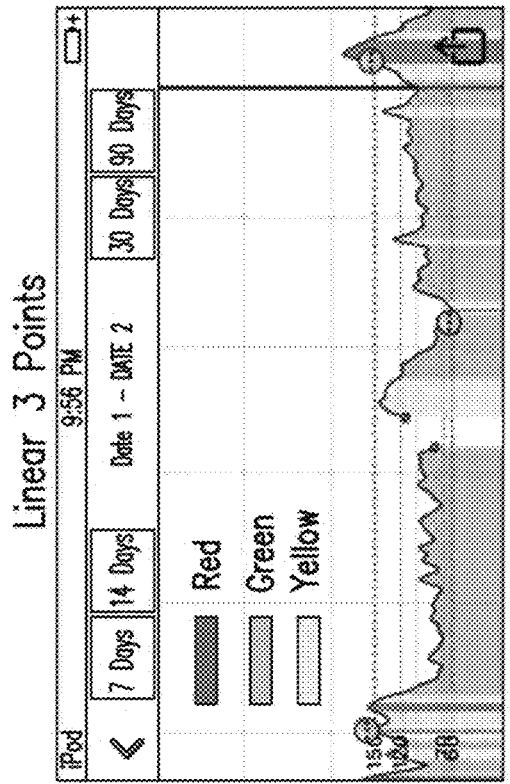
Figure 10B:
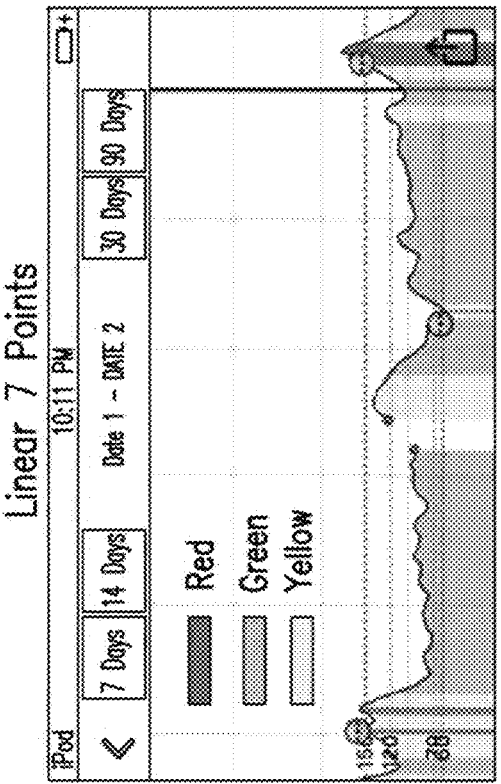
Figure 10C:
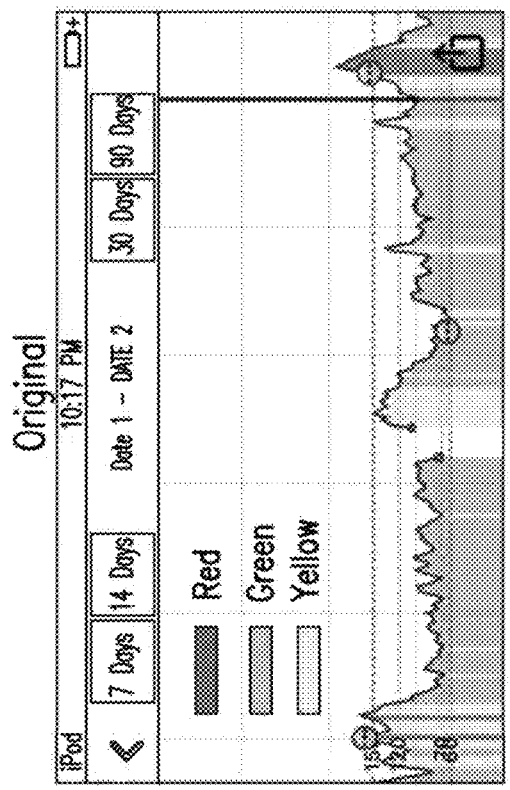
Figure 10D:
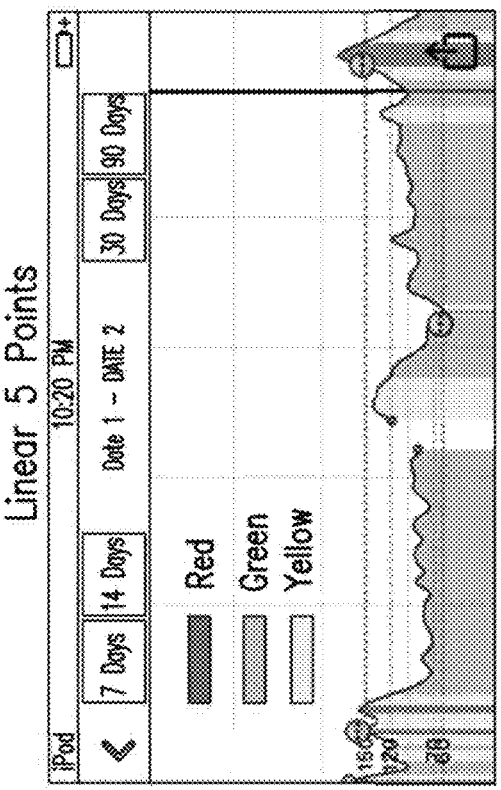
Figure 10E:
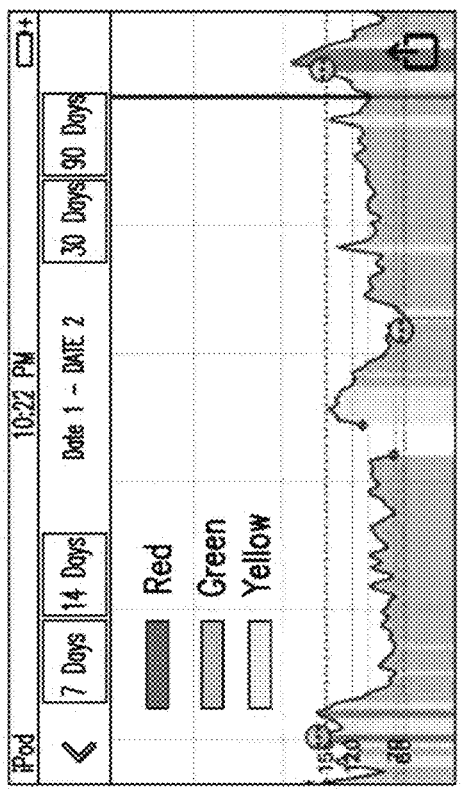
Figure 10F:
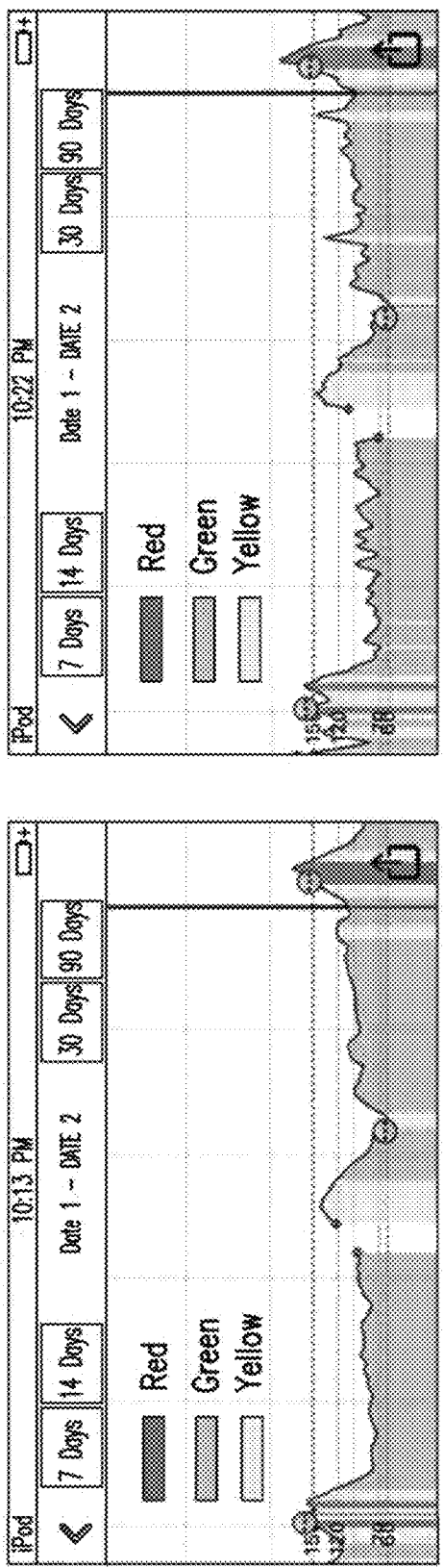
Figure 10G:
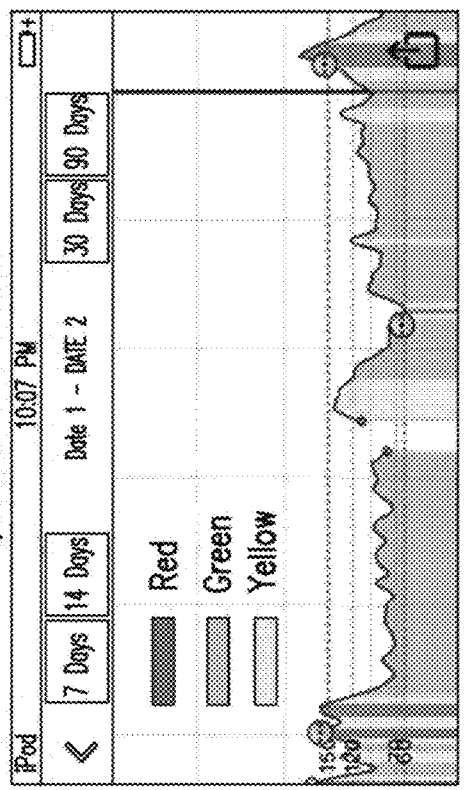
Figure 10H:
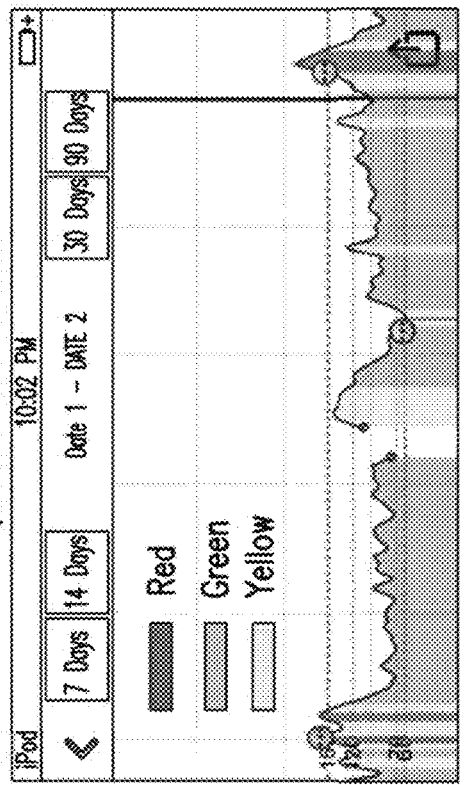
Figure 11E:
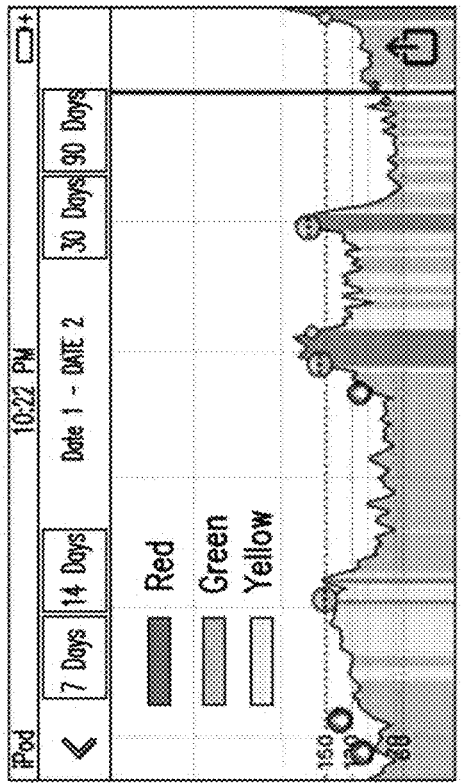
Figure 11F:
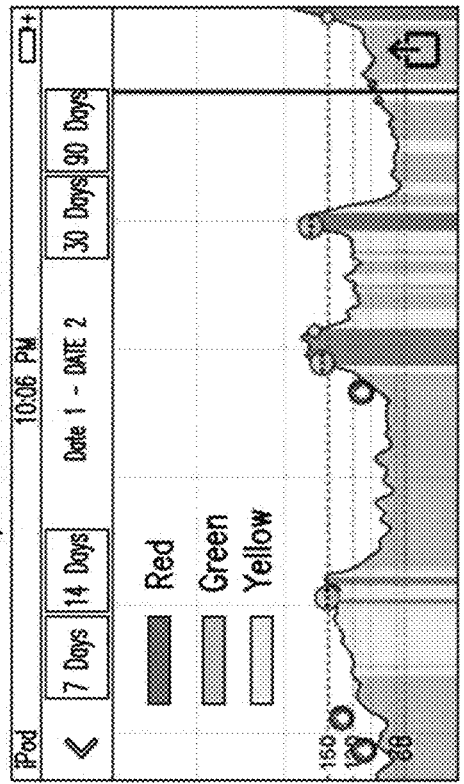
Figure 11G:
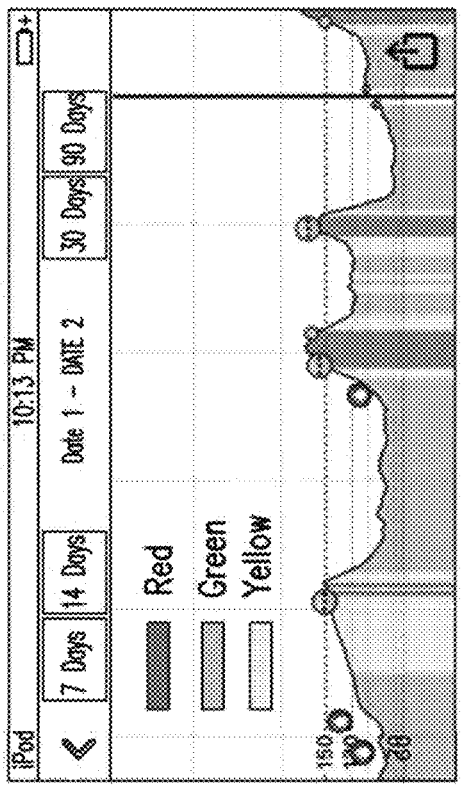
Figure 11H:
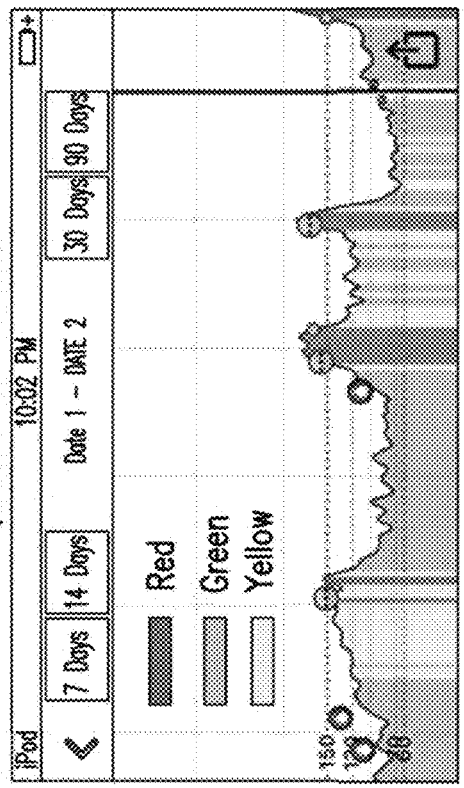
Figure 12A:
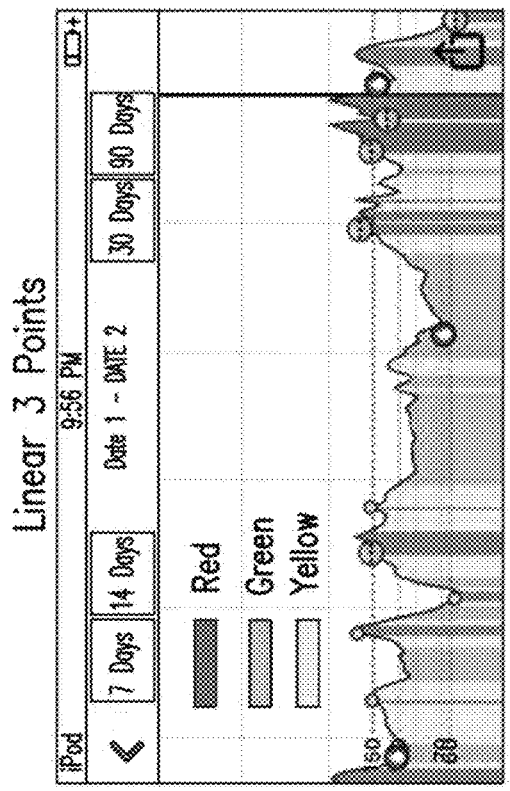
Figure 12B:
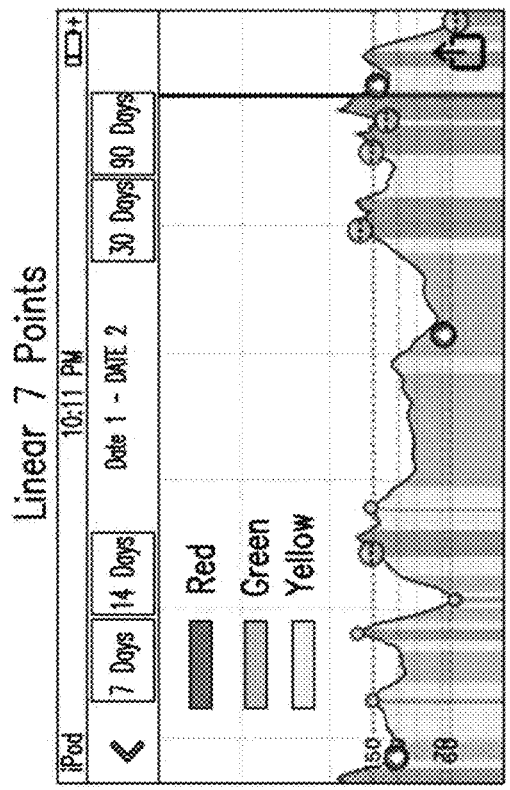
Figure 12C:
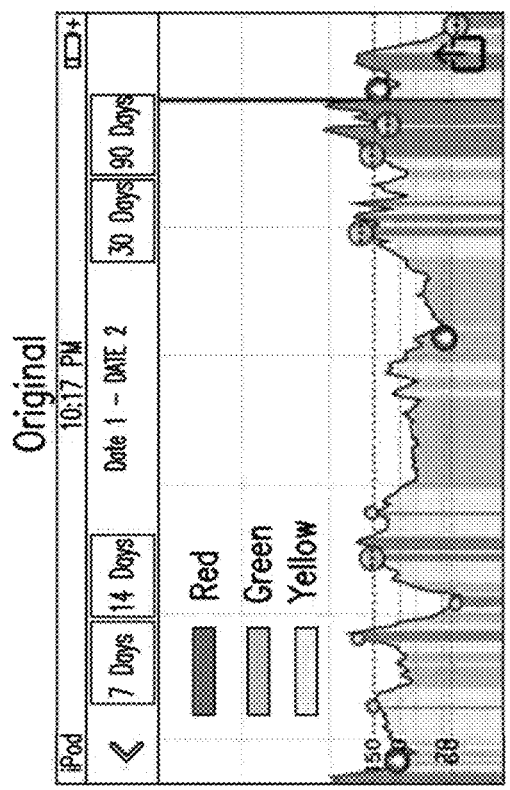
Figure 12D:
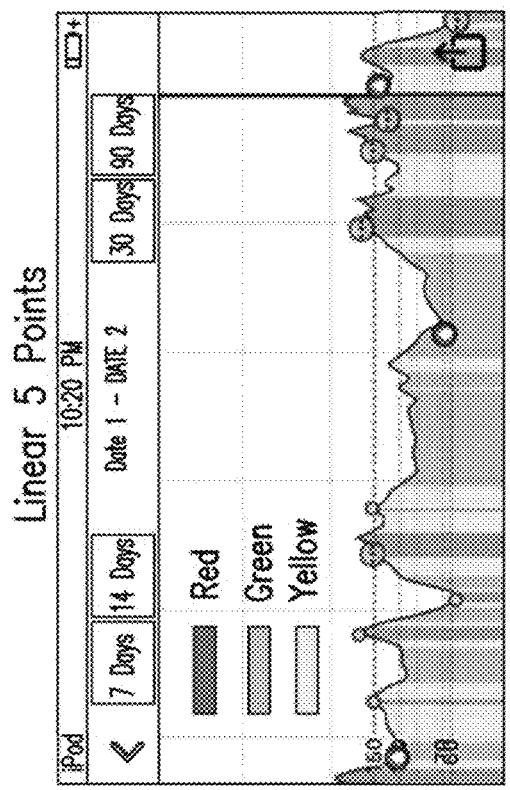
Figure 12E:
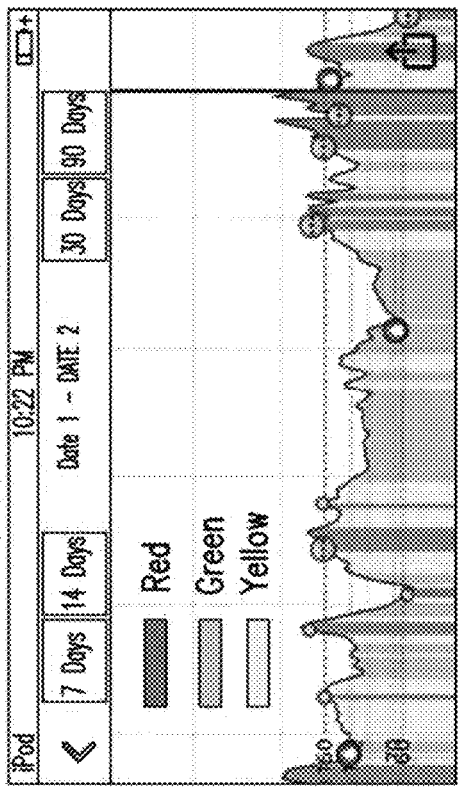
Figure 12F:
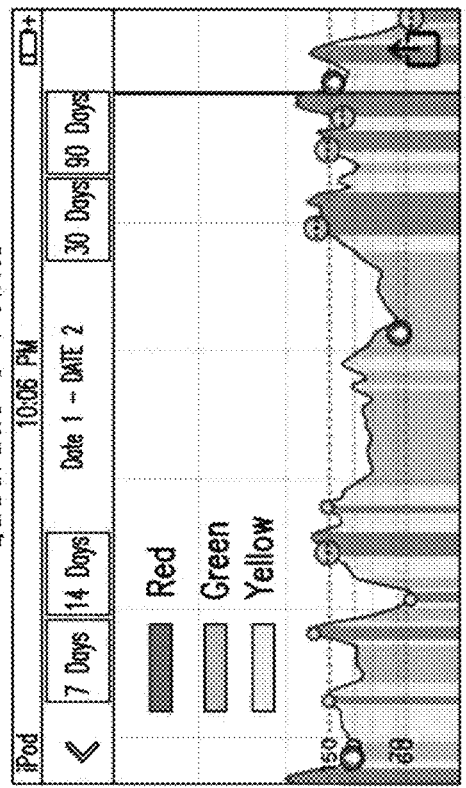
Figure 12G:
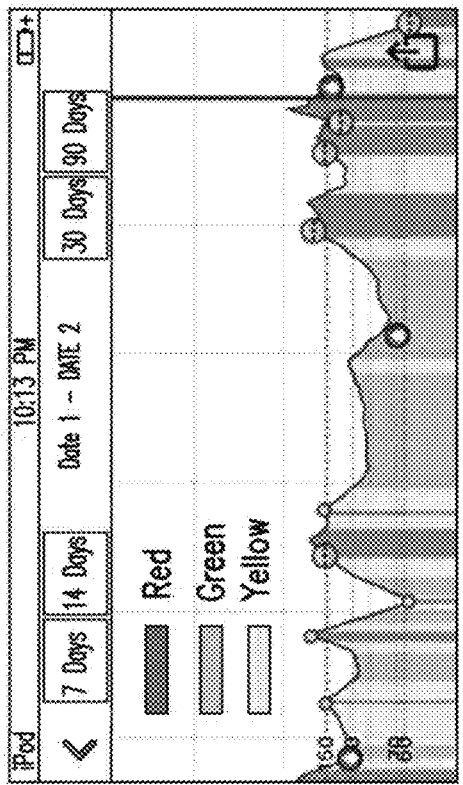
Figure 12H:
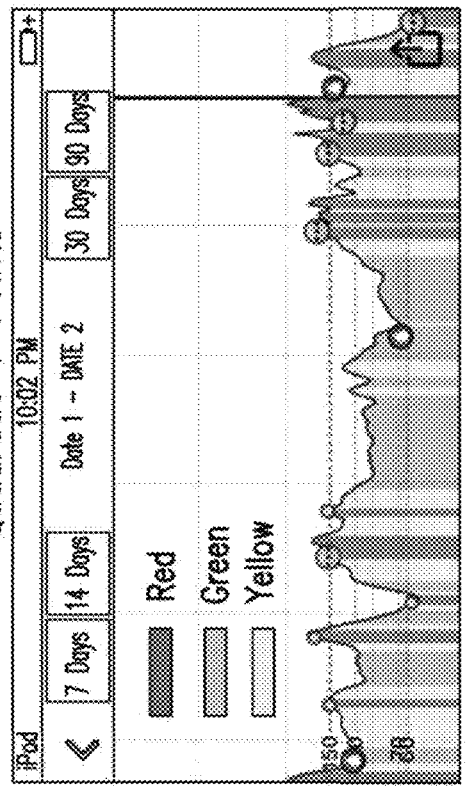
Figure 13A:
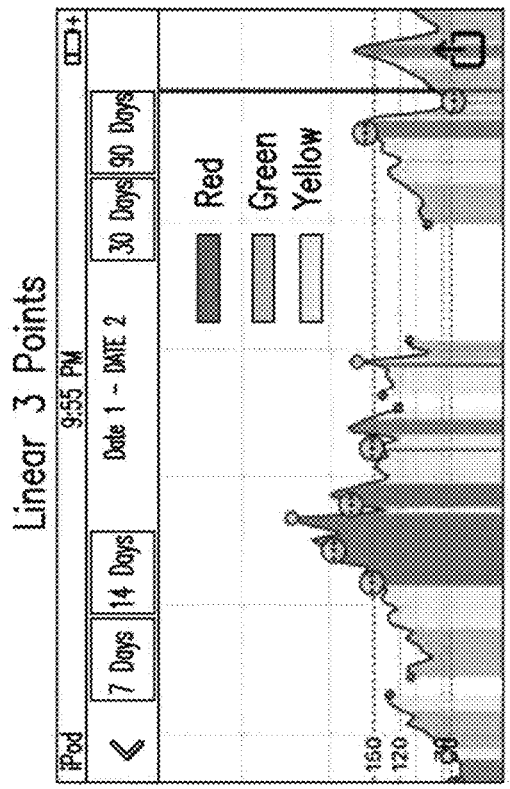
Figure 13B:
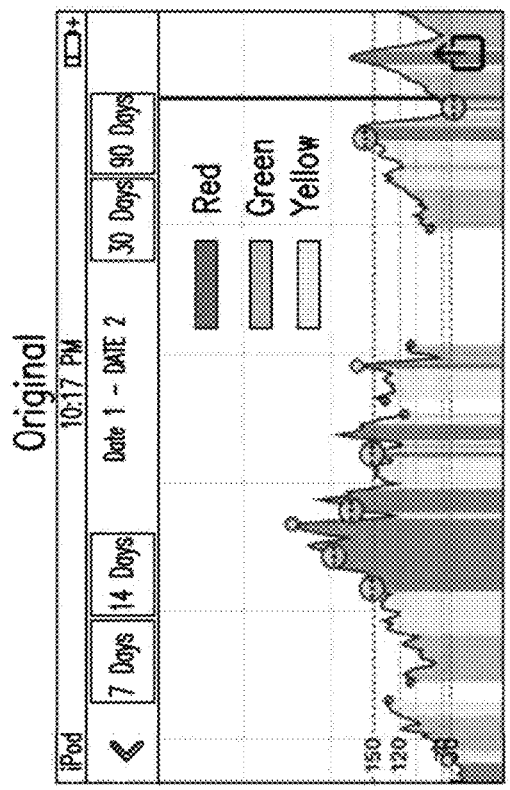
Figure 13C:
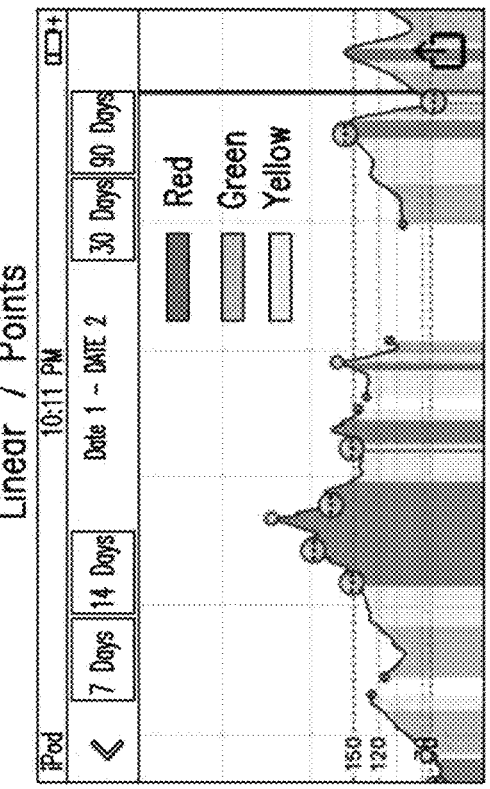
Figure 13D:
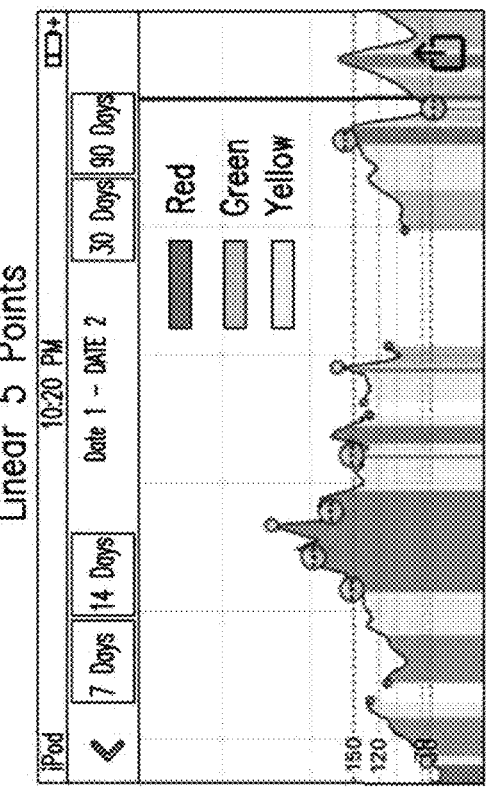
Figure 14A:
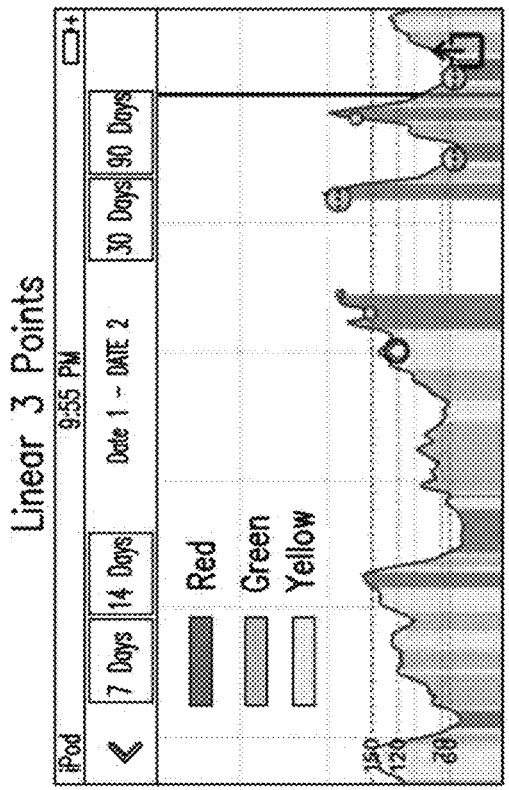
Figure 14B:
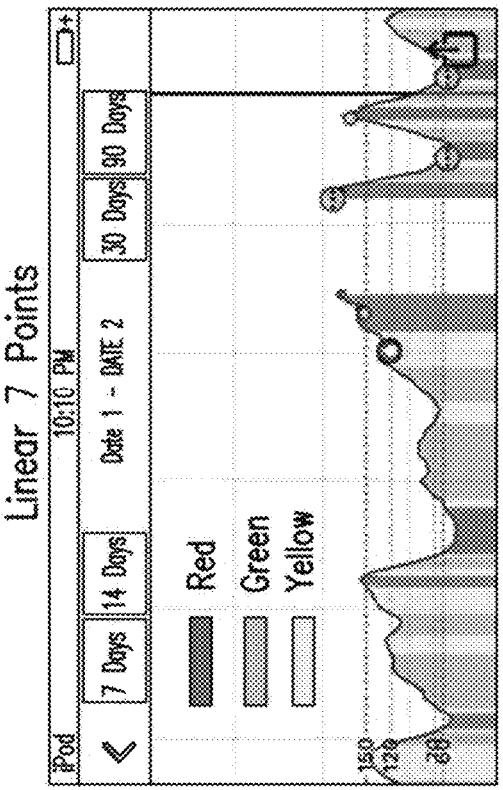
Figure 14C:
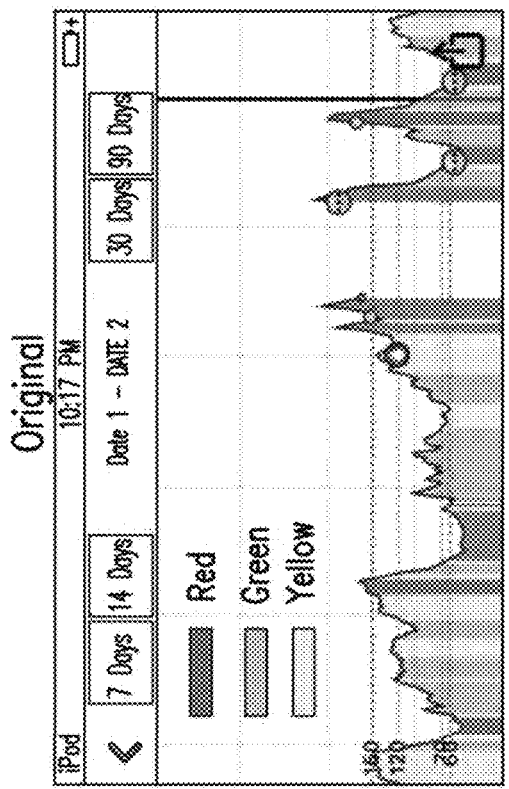
Figure 14D:
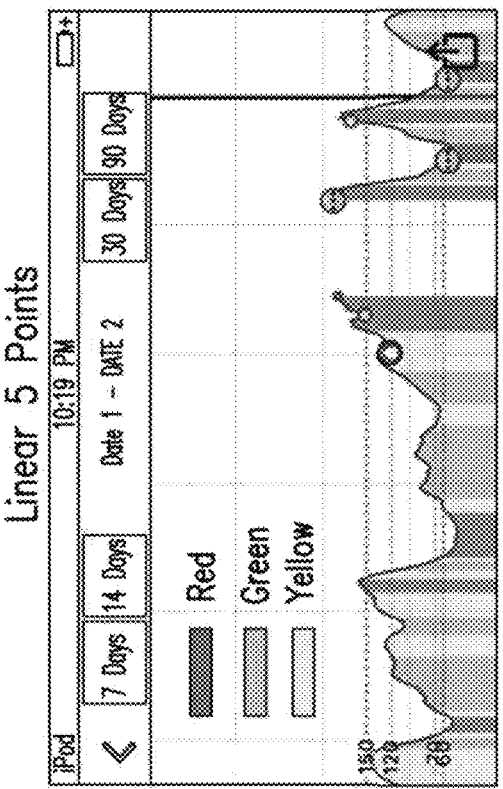
Figure 14E:
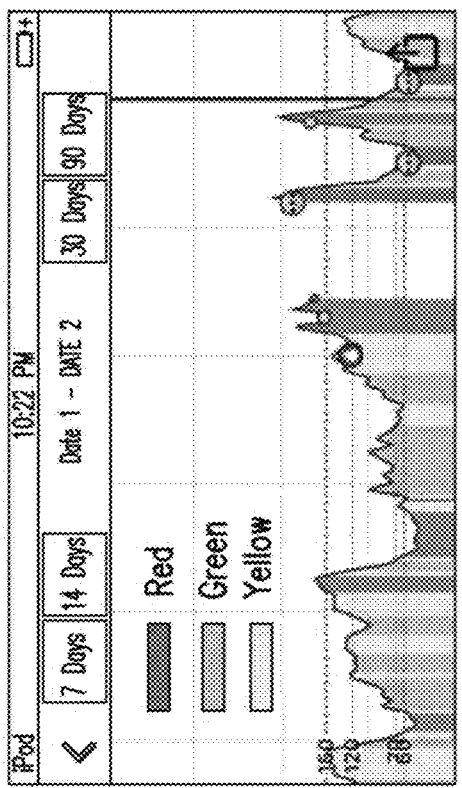
Figure 14F:
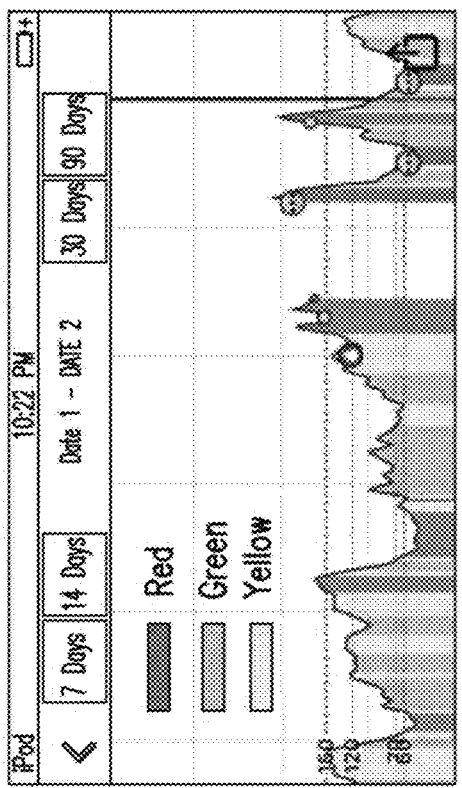
Figure 14G:
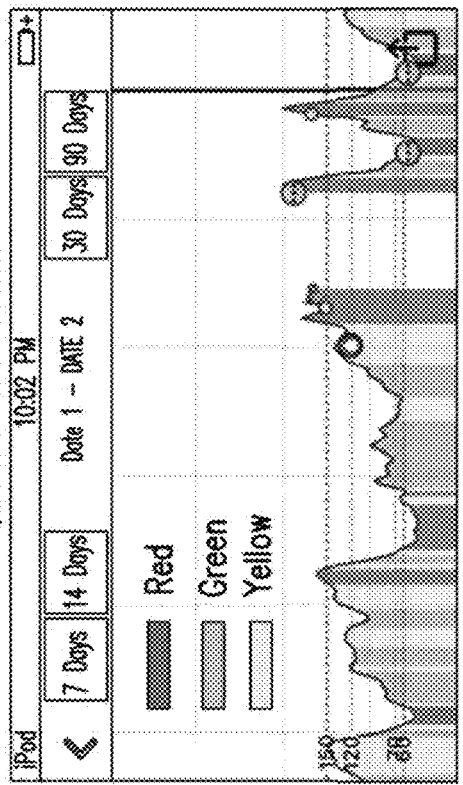
Figure 14H:
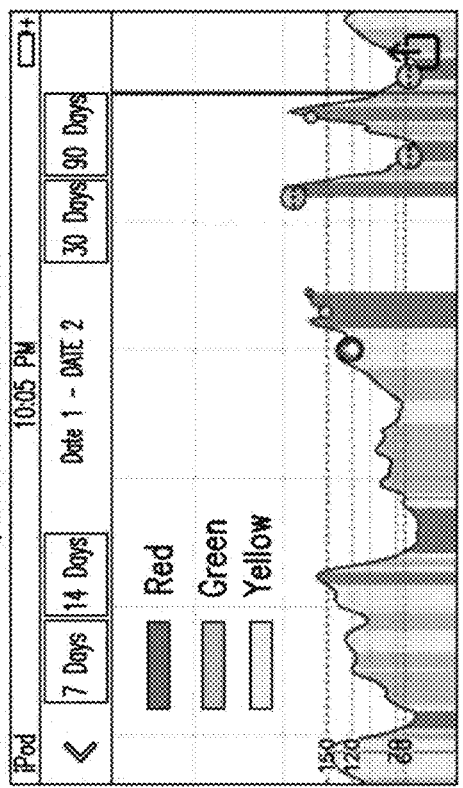
Figure 15A:
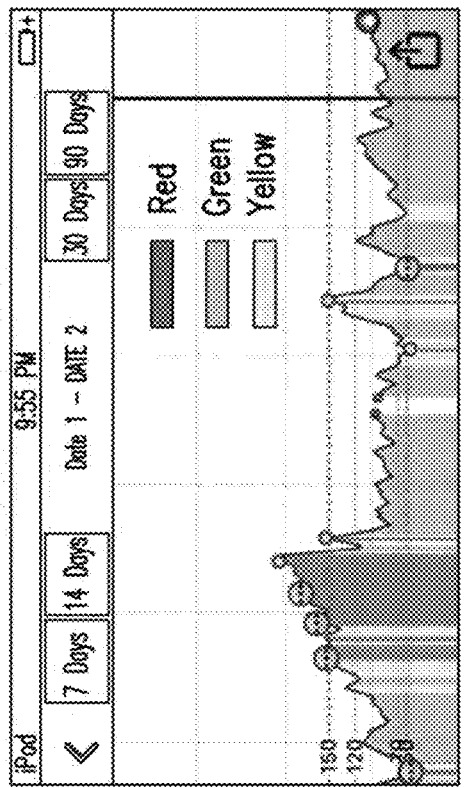
Figure 15B:
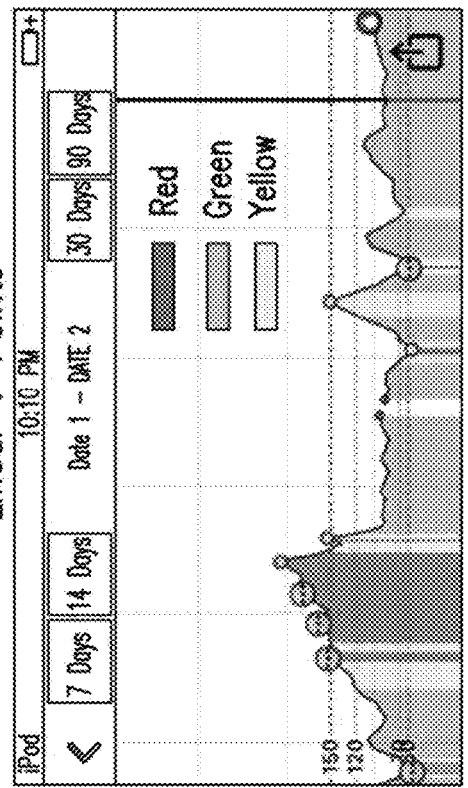
Figure 15C:
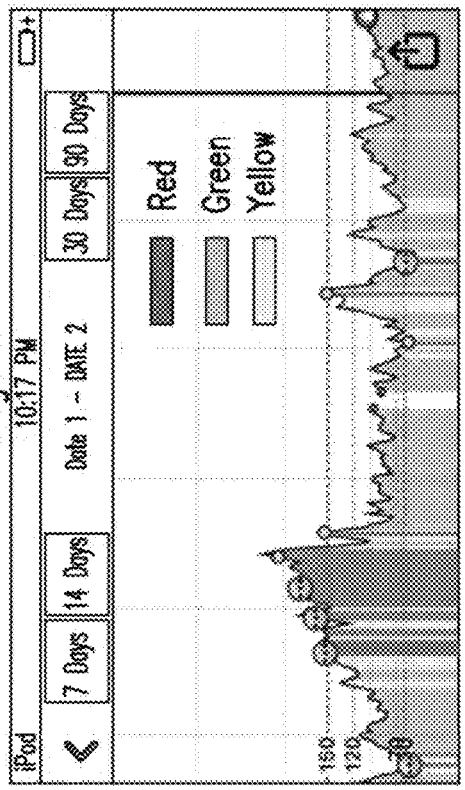
Figure 15D:
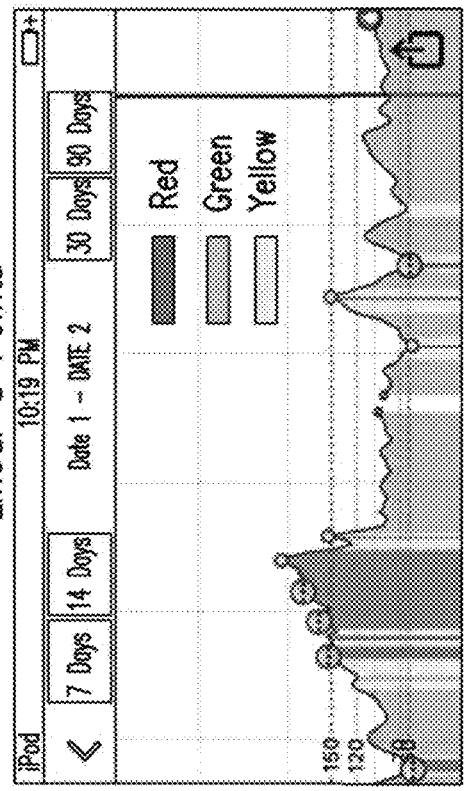
Figure 15F:
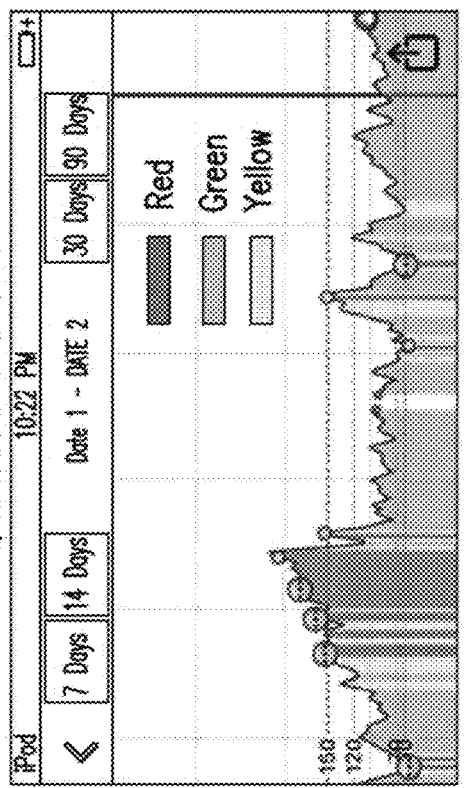
Figure 15H:
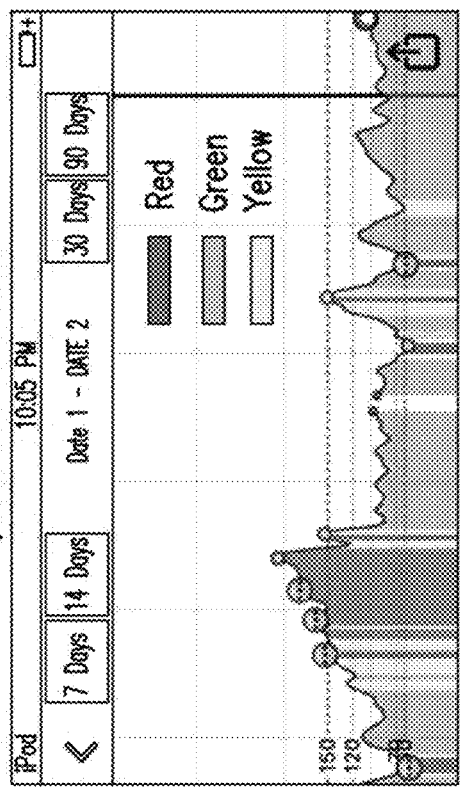
Figure 15E:
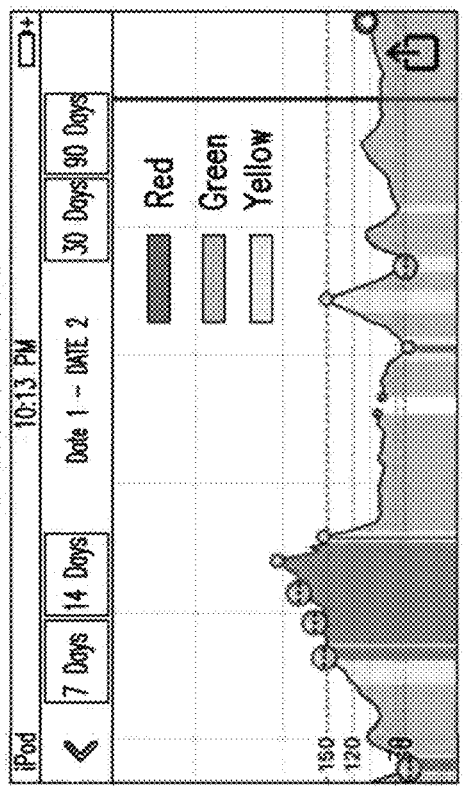
Figure 15G:
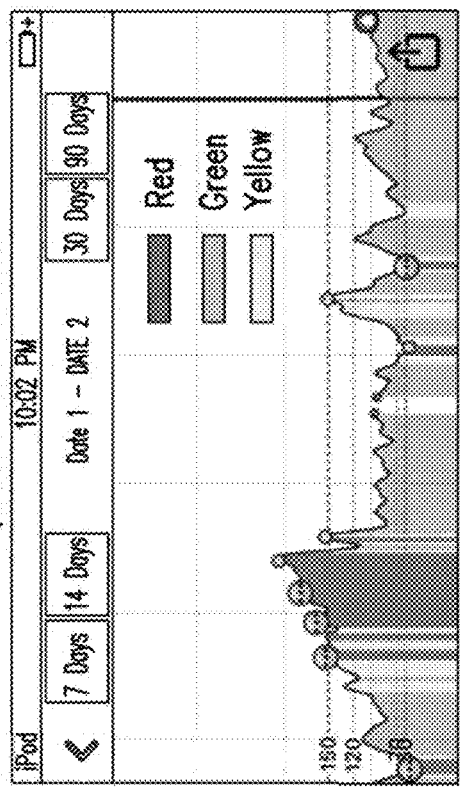
Figure 16A:
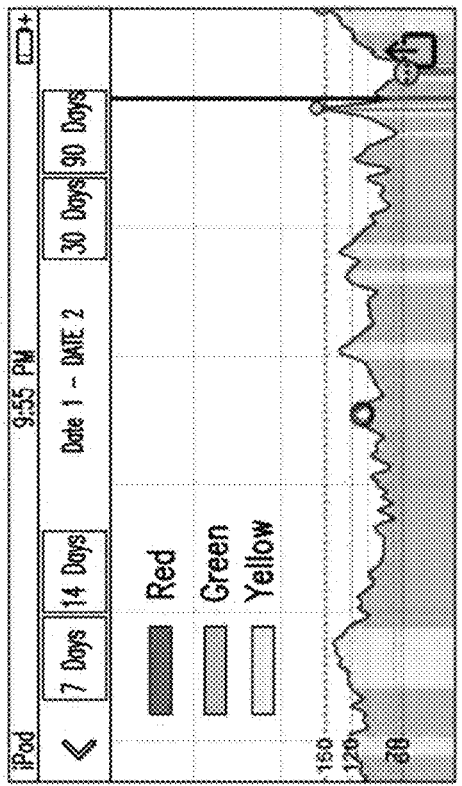
Figure 16B:
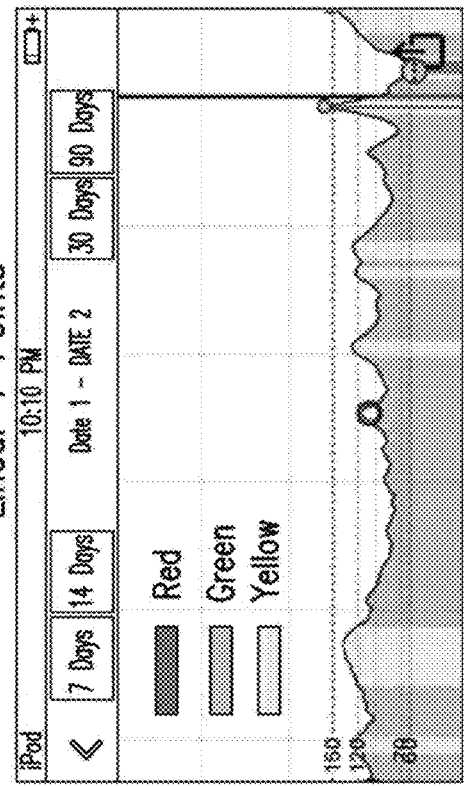
Figure 16C:
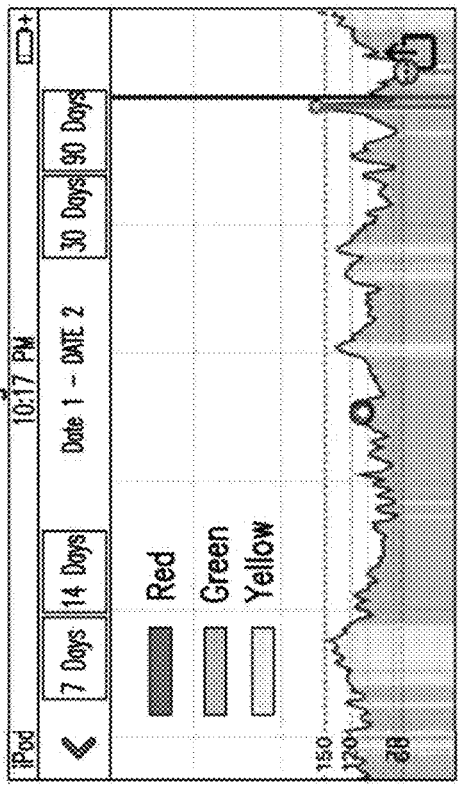
Figure 16D:
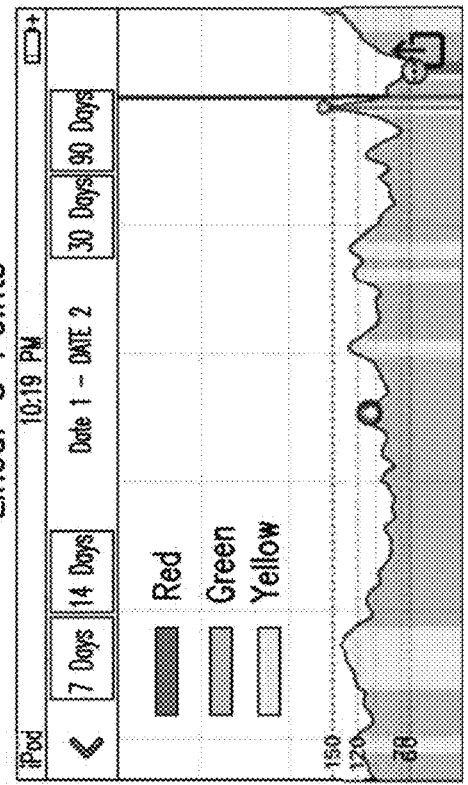
Figure 16E:
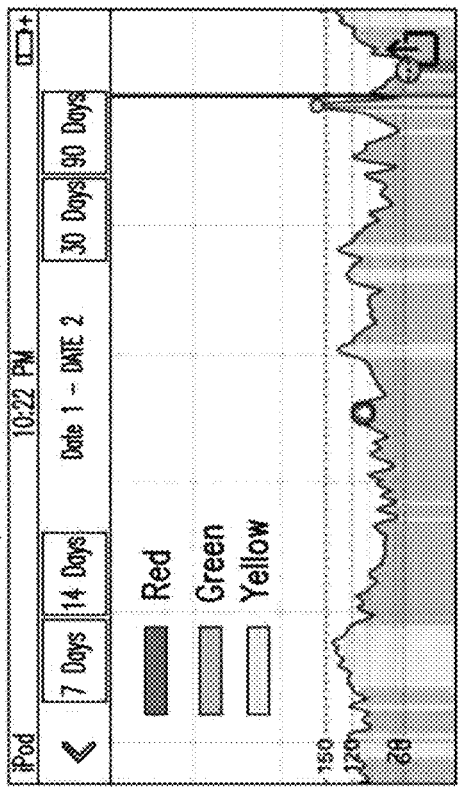
Figure 16F:
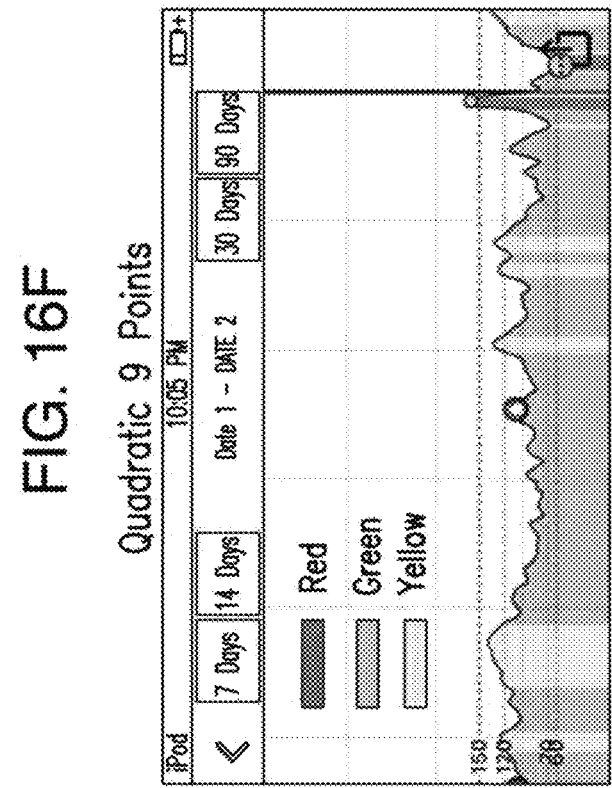
Figure 16G:
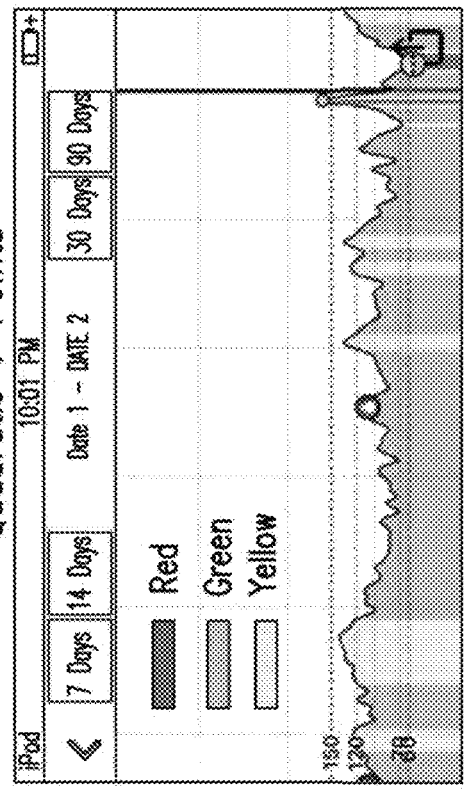
Figure 16H:
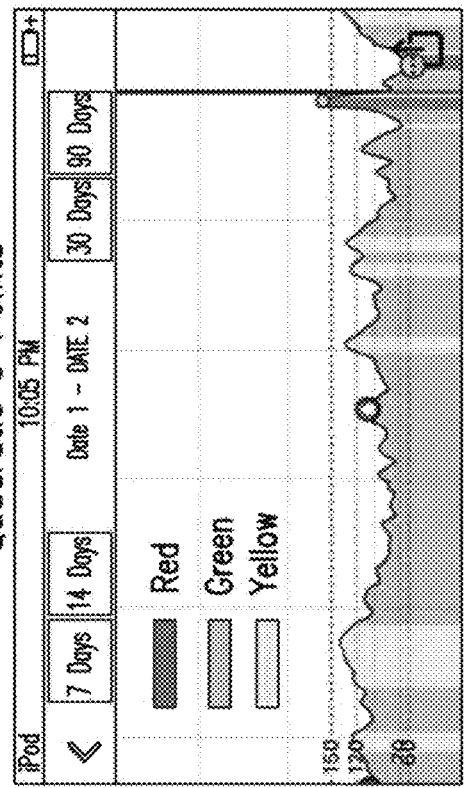
Figure 17B:
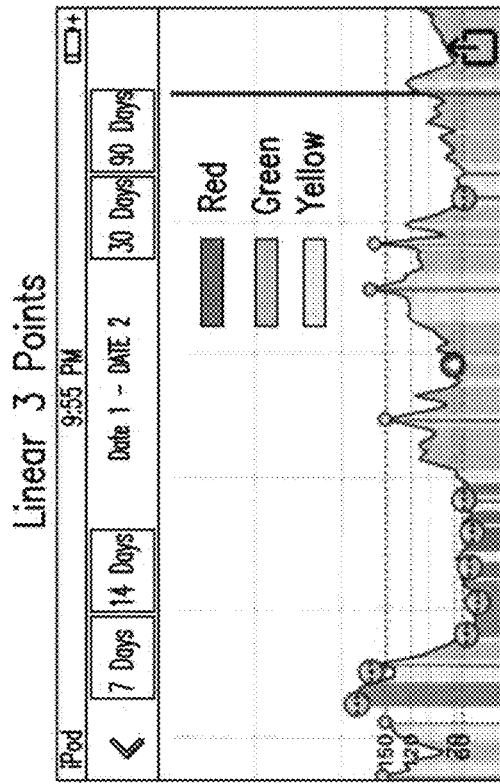
Figure 17D:
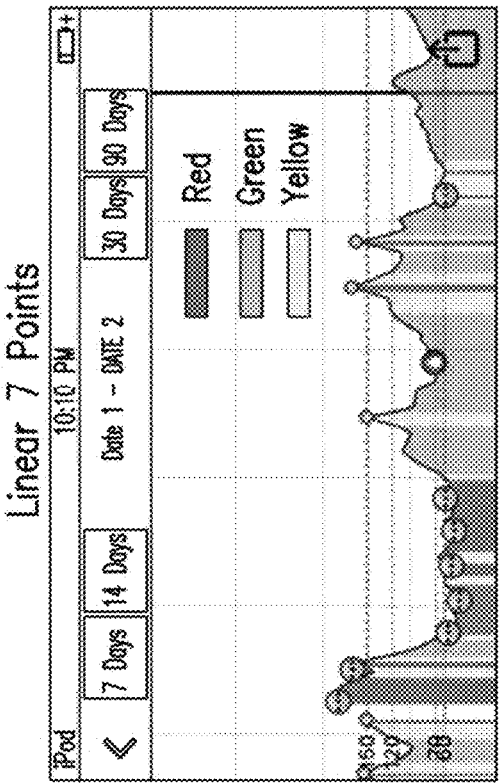
Figure 17A:
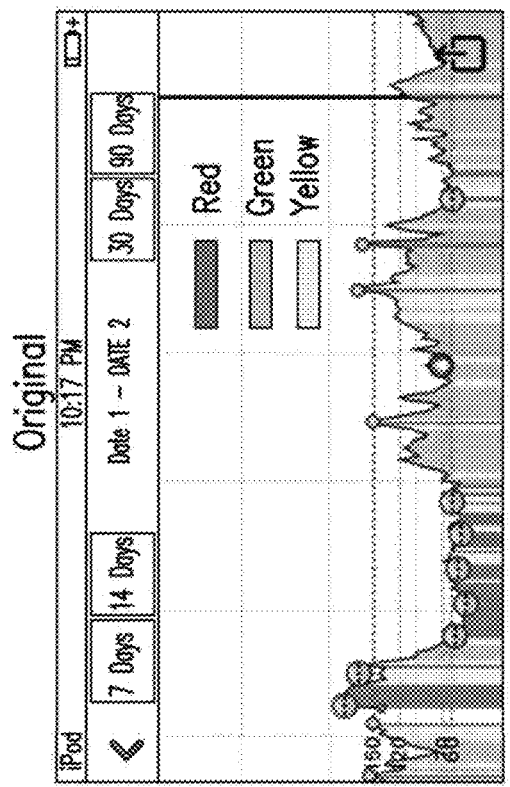
Figure 17C:
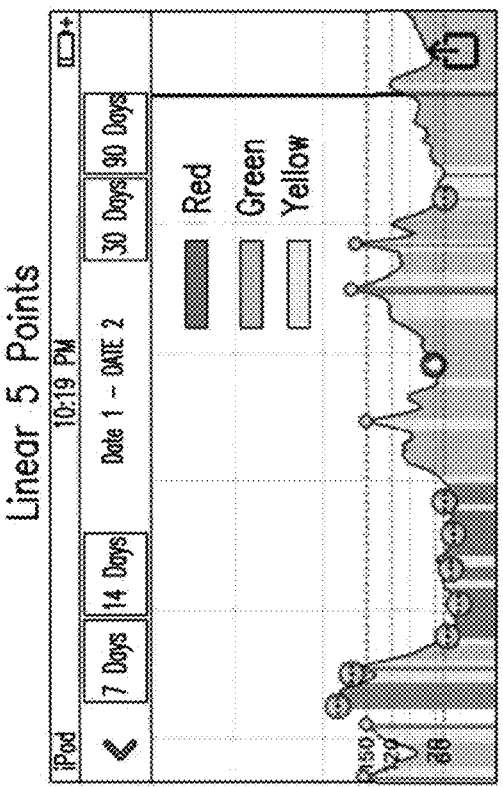
Figure 17E:
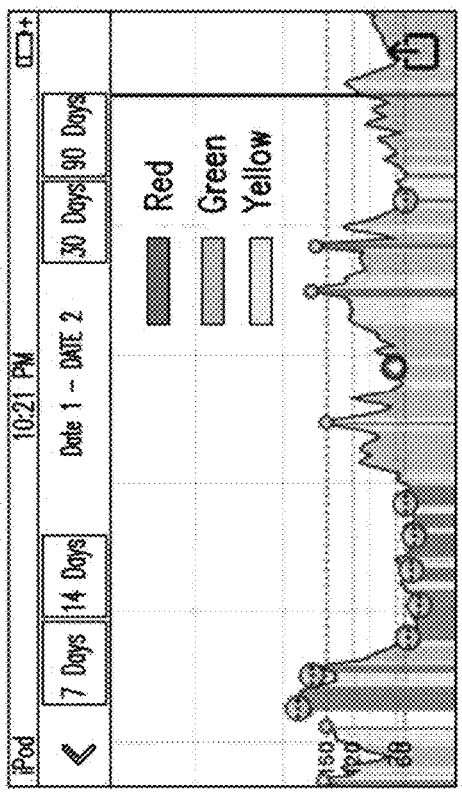
Figure 17G:
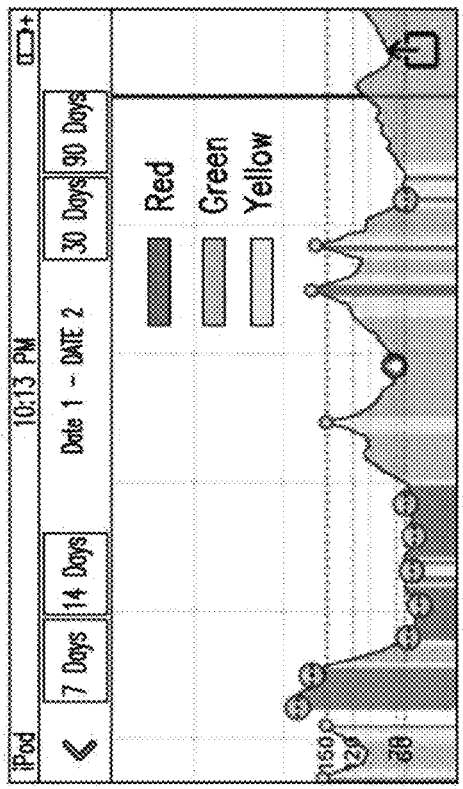
Figure 17F:
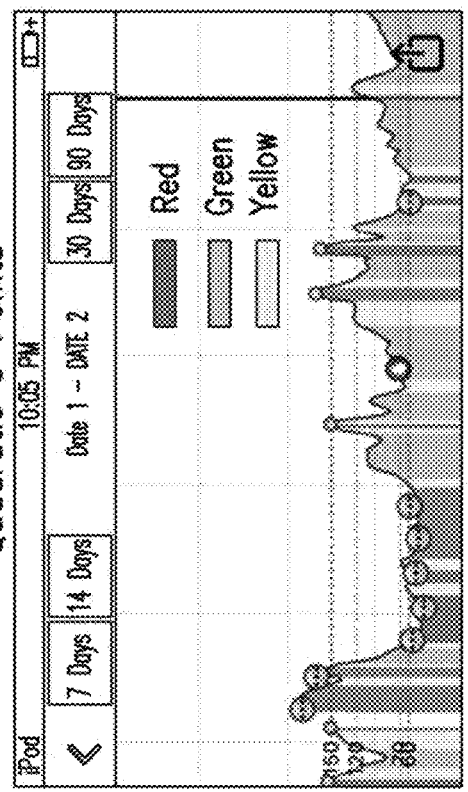
Figure 17H:
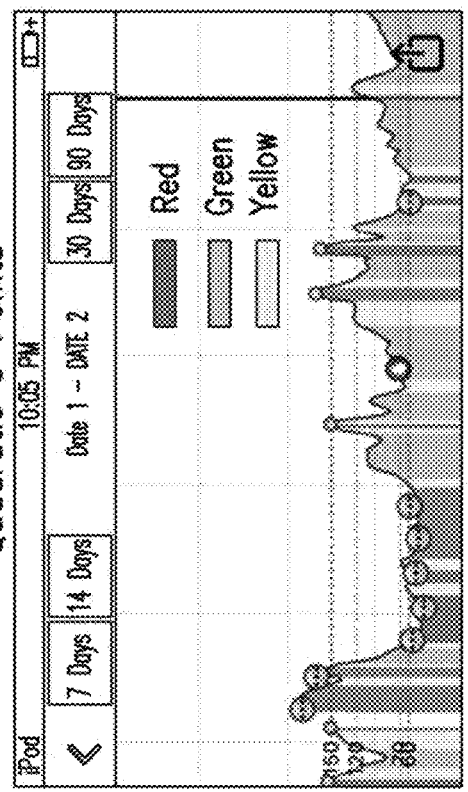
Figure 18A:
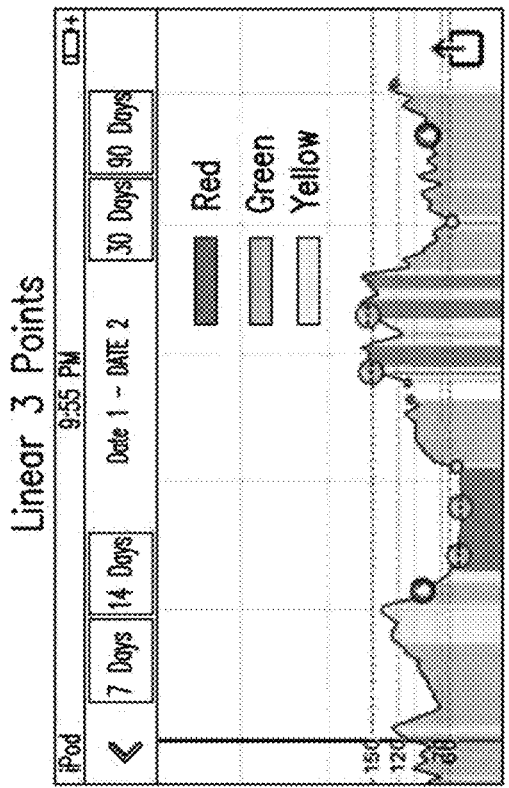
Figure 18B:
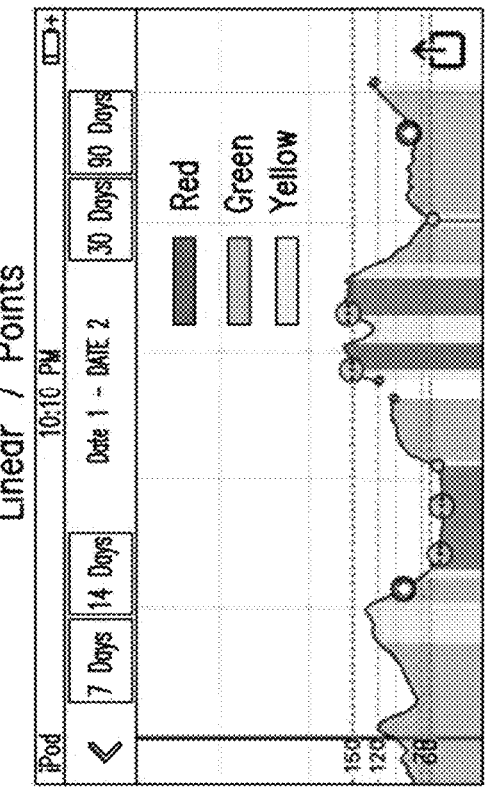
Figure 18C:
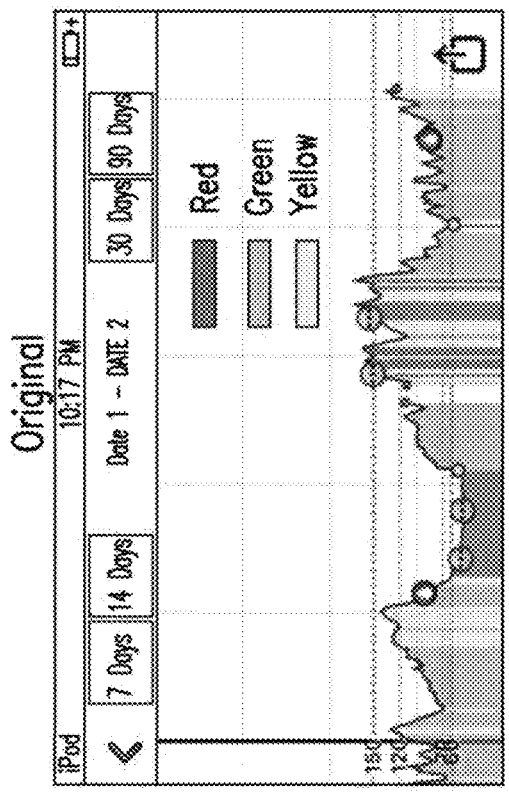
Figure 18D:
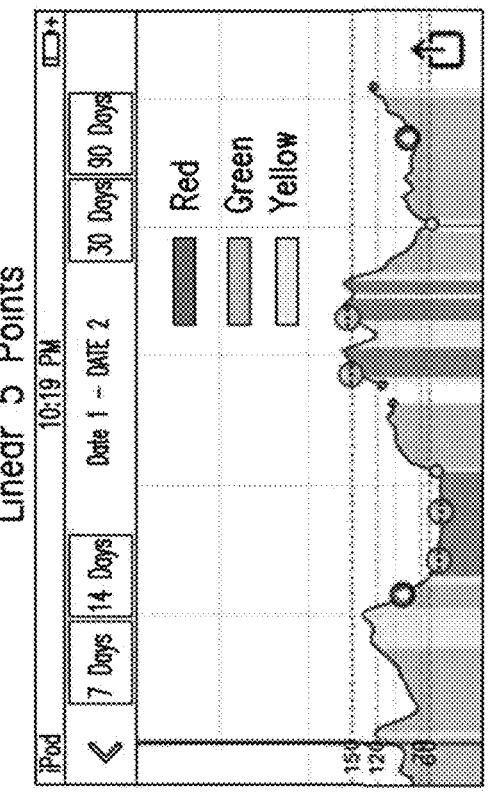
Figure 18E:
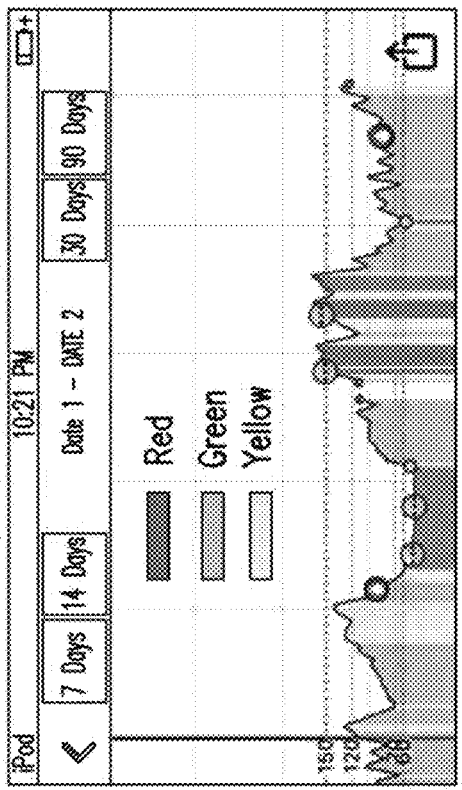
Figure 18F:
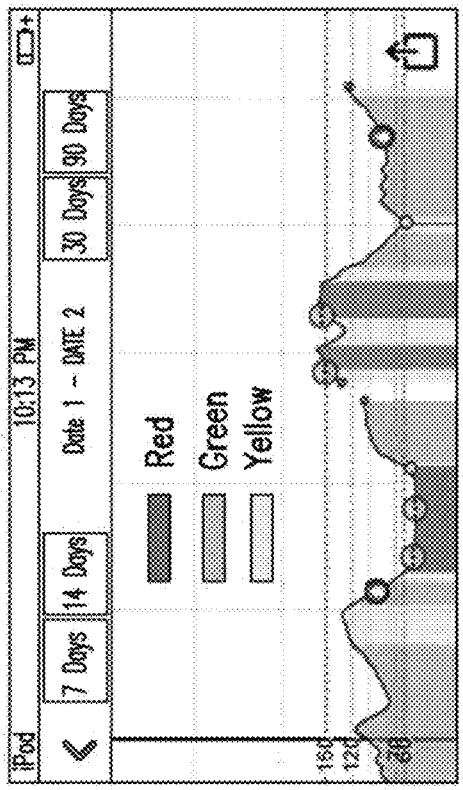
Figure 18G:
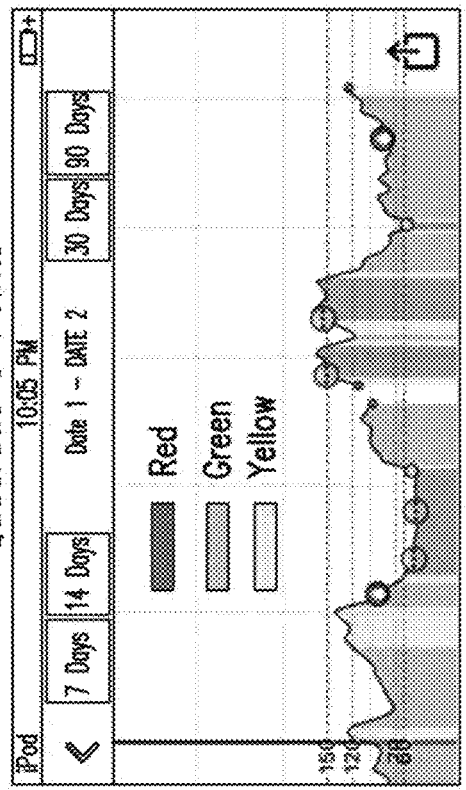
Figure 18H:
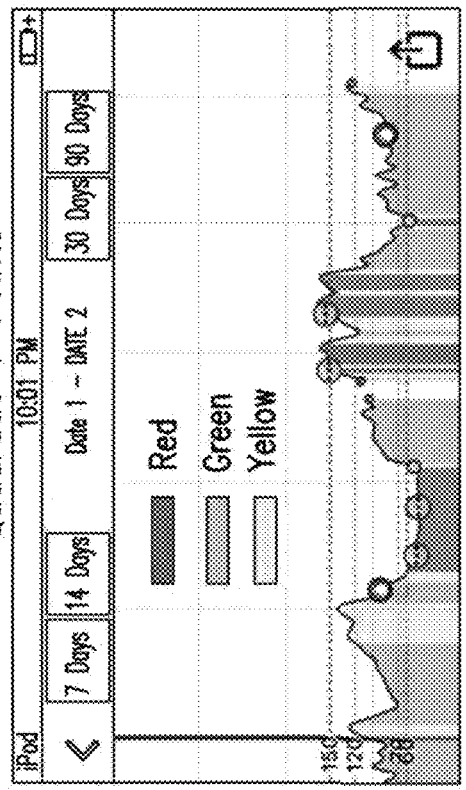

FIG. 4 is an example of a home screen display of a medical mobile application (MMA) in accordance with aspects of various embodiments of the present invention. According to some embodiments, the workspace display of the MMA may be depicted in a GUI on the display 220 of the display device 105. In some embodiments, the home screen may display one or more of real-time analyte concentrations received from transceiver 101, rate and direction of analyte level change, graphical trends of analyte levels, alarms or alerts for hypoglycemia or hyperglycemia, and logged events such as, for example and without limitation, meals, exercise, and medications. Table 1 below depicts several informational non-limiting examples of items and features that may be depicted on the home screen.

TABLE 1

| Home Screen | |
|---|---|
| Status bar | Shows the status of user's glucose level |
| Transceiver/Transmitter ID | This is the transceiver being used; the transceiver name can be changed by going to Settings > System |
| Current glucose value | A real-time glucose reading; this may be updated every 5 minutes |
| Date and time | The current date and time with navigational options, such as scroll left or right to see different dates and times |
| Alarm and Events | Shows an icon when an alert, alarm, or event occurs |
| Bluetooth Connection | Shows the strength of the Bluetooth connection |
| Handheld Device Battery Level | Indicates the battery strength of the handheld device |
| Transmitter/Transceiver Battery Level | Indicates the battery strength of the transceiver |
| Transmitter/Transceiver Connection Status Icon | Shows the strength of the transceiver connection |
| Trend Arrow | Shows the direction a patient's glucose level is trending |
| Unit of Measurement | This is the units for the glucose value |
| High Glucose Alarm Level | This is the high glucose alarm or alert level, which may be user settable |
| Glucose High Target Level | This is the high glucose target level, which may be user settable |
| Low Glucose Alarm Level | This is the low glucose alarm or alert level, which may be user settable |
| Glucose Low Target Level | This is the low glucose target level, which may be user settable |
| Stacked Alerts | Shows when there are several alerts at the same time |
| Glucose Trend Graph | A user can navigate or scroll through the graph to see the trend over time |
| Menu | Navigation to various sections of the MMA, such as:<br>Home    Reports    Settings<br>Calibrate    Share My Data    About<br>Notifications    Placement Guide<br>Event Log    Connect |
| Calibration Point Icon | This icon appears when a calibration is entered |
| Profile Indicator | This indicator may indicate what profile is being applied, such as a normal profile, temporary profile, vacation profile, and the like. | the MMA may store glucose level history and statistics for a patient on the display device 105 (e.g., in memory 214 and/or DSS 533) and/or in a remote data storage system.

In some embodiments, a user of the display device 105, which may be the same or different individual as patient, may initiate the download of the MMA from a central repository over a wireless cellular network or packet-switched network, such as the Internet. Different versions of the MMA may be provided to work with different commercial operating systems, such as the Android OS or Apple OS running on commercial smart phones, tablets, and the like. For example, where display device 105 is an Apple iPhone, the user may cause the display device 105 to access the Apple iTunes store to download a MMA compatible with the Apple OS, whereas where the display device 105 is an Android mobile device, the user may cause the display In some embodiments, as shown in FIG. 4, the home screen may include one or more of a status notification bar 1301, a real-time current glucose level 1303 of a patient, one or more icons 1305, a trend arrow 1307, a historical trend graph 1309, a profile indicator 1333, and navigation tools 1311. The status notification bar 1301 may depict, for example and without limitation, alarms, alerts, and notifications related to, for example, glucose levels and system statistics and/or status. The one or more icons 1305 may represent the signal strength of the transceiver 101 and/or the battery level of the transceiver 101. The trend arrow 1307 may indicate a rate and/or direction of change in glucose measurements of a patient. The historical trend graph 1309 may be, for example and without limitation, a line graph and may indicate trends of glucose levels of a patient. The navigation tools 1311 may allow a user to navigate through different areas or screens of the MMA. The screens may include, for example and without limitation, one or more of Home, Calibrate, Event Log, Notifications, and Menu screens.

In some embodiments, the historical trend graph 1309 may depict logged events and/or user inputted activities such as meals (nutrition, amount of carbohydrates), exercise (amount of exercise), medication (amount of insulin units), and blood glucose values as icons on positions of the graph corresponding to when such events occurred. In some embodiments, the historical trend graph 1309 may show one or more of a boundary or indication of a high glucose alarm level 1313, a low glucose alarm level 1315, a high glucose target level 1317, and a low glucose target level 1319. In some embodiments, a user may interact with a time or date range 1321 option via the GUI to adjust the time period of the glucose level displayed on the historical trend graph 1309. In some embodiments, the date range 1321 may be specified by a user and may bet set to different time periods such as 1, 3, 24 hours, 1, 7, 14, 30, and 60 days, weeks, months, etc. In some embodiments, the historical trend graph 1309 may show high, low, and average glucose levels of a patient for the selected date range 1321. In other embodiments, the historical trend graph 1309 may be a pie chart, log book, modal day, or other depiction of glucose levels of a patient over a selectable date range 1321, any of which may further depict high, low, and average glucose levels of the patient over that date range 1321.

In some embodiments, the trend arrow 1307 may be depicted in five different configurations that signify direction (up, down, neutral) and rate (rapidly, very rapidly slow, slow, very slow, and stable) of glucose change. In some embodiments, the MMA and/or the transceiver 101 may use the last twenty minutes of continuous glucose measurement data received from the sensor 101 and/or processed by the transceiver 730 in the calculation used to determine the orientation of the trend arrow 1307. In some embodiments, there may be times when the trend arrow 1307 may not be displayed due to, for example, there being insufficient sensor values available for the trend calculation. In some embodiments, a trend arrow 1307 displayed in a horizontal orientation (approximately 0° along the horizontal direction of the GUI display) may indicate that the glucose level is changing gradually, such as, for example, at a rate between −1.0 mg/dL and 1.0 mg/dL per minute. In some embodiments, a trend arrow 1307 displayed slightly in the upwards direction (approximately 45° up from the horizontal direction of the GUI display) may indicate that the glucose level is rising moderately, such as, for example, at a rate between 1.0 mg/dL and 2.0 mg/dL per minute. In some embodiments, a trend arrow 1307 displayed slightly in the downwards direction (approximately 45° down from the horizontal direction of the GUI display) may indicate that the glucose level is falling moderately, such as, for example, at a rate between 1.0 mg/dL and 2.0 mg/dL per minute. In some embodiments, a trend arrow 1307 displayed in a vertical direction (approximately 90° up from the horizontal direction of the GUI display) may indicate that the glucose level is rising very rapidly, such as, for example, at a rate more than 2.0 mg/dL per minute. In some embodiments, a trend arrow 1307 displayed in a downwards direction (approximately 90° down from the horizontal direction of the GUI display) may indicate that the glucose level is falling very rapidly, such as, for example, at a rate more than 2.0 mg/dL per minute. In some embodiments, the trend arrow 1307 is different from a predicted glucose alarm or alert. For example, the trend arrow 1307 may indicate rate and direction of change regardless of glucose value, whereas predicted glucose alarms or alerts may indicate reaching a certain glucose level based on current trends. For example, the MMA may cause a predicted low glucose alarm or alert to be displayed in the notification bar 1301 while still displaying a relatively stable trend arrow 1307 (e.g., at 0° or 45° from the horizontal direction of the GUI display).

In some embodiments, the historical trend graph 1309 may allow a user to quickly review and analyze historical data and/or trend information of a patient's glucose levels over time. In some embodiments, the historical trend graph 1309 may include icons or markers along the trend line to reflect alarms, alerts, notifications, and/or any events that were automatically or manually logged by the user into the display device 105 via a GUI display generated by the MMA. Where one or more of such icons or markers are displayed on the historical trend graph 1309, a user may select any one of the icons or markers to obtain more information about the item. For example, in response to a selection of a mark on the historical trend graph 1309, the MMA may generate a popup window on the display 220 that provides more information about the mark.

In some embodiments, the historical trend graph 1309 may enable a user to quickly review how well a patient is doing against glucose targets and/or alarms or alerts. For example, a user may establish a high glucose alarm level 1313 and/or a low glucose alarm level 1315, as well as a high glucose target level 1317 and/or a low glucose target level 1319. The high glucose alarm level 1313 and/or low glucose alarm level 1315 may be visually depicted over the historical trend graph 1309, for example, using a colored dashed line (such as red). Additionally, the high glucose target level 1317 and low glucose target level 1319 may be visually depicted over the historical trend graph 1309, for example, using a color dashed line (such as green).

In some embodiments, the colors of the historical trend graph 1309 may change depending on a glucose level 1303 status. For example, during the times where the glucose level 1303 was outside of the high glucose alarm level 1313 or low glucose alarm level 1315, then the portion of the historical trend graph 1309 corresponding to those times may be filled in red. As another example, during the times where the glucose level 1303 is between the high glucose target level 1317 and the low glucose target level 1319, then the portion of the historical trend graph 1309 corresponding to those times may be filled in green. As yet another example, during the times where the glucose level 1303 is between a glucose target level 1317, 1319 and a corresponding alarm level 1313, 1315, then the portion of the historical trend graph 1309 may be filled in yellow.

In some embodiments, the historical trend graph 1309 may be displayed with one or more selectable date range icons 1321 that allow a user to change the day/time period corresponding to the historical trend graph 1309 in real-time. For example, a user may select a forwards or backwards selectable option (such as an arrow) or use a swipe or fling gesture that may be recognized by GUI to navigate to a later or earlier time period, respectively, such as a day, month, etc. In some embodiments a user may choose an older graph 1309 to display by tapping the date on the date range 1321 portion of the screen and submitting or entering a desired date and/or time to review. In some embodiments, a user may use one or more gestures that are recognized by the GUI, such as a pinch, zoom, tap, press and hold, or swipe, on graph 1309. For example, a user may pinch the historical trend graph 1309 with a thumb and index finger in order to cause the MMA to display different time/dating settings or adjust a time/date setting on the historical trend graph 1309. In some embodiments, a user may tap or press and hold a time event on historical trend graph 1309, and in response the MMA may display further detail on the time event, such as a history, reading value, date/time, or association to other events or display a prompt for entry of a time event.

In some embodiments, the MMA may store glucose data 1303 on the display device 105 (e.g., in memory 214 and/or DSS 533) so long as there is available memory space. Additionally or alternatively, the MMA may cause the display device 105 to send a sync request message to store the glucose data 1303 on a remote storage device.

In some embodiments, the MMA may cause the GUI to display navigational tools 1311 that allow a user to navigate to different features and screens provided by the MMA. For example, the navigational tools 1311 may comprise a navigation bar with one or more of a plurality of selectable navigation options 1323, 1325, 1327, 1329, and 1331, such as buttons or icons. As shown in FIG. 4, in some embodiments, the selectable navigation options may allow a user to navigate to one or more of the "Home" screen 1323, a "Calibrate" screen 1325, an "Event Log" screen 1327, a "Notifications" screen 1329, and a "Menu" screen 1331. Upon a user selection of one of the selectable navigation options in the navigation tools area 1311, a new screen corresponding to the selected option may be displayed on a display device by the GUI.

In some embodiments, the transceiver 101 may receive one or more sensor measurements (e.g., light, pressure, current, and/or temperature measurements) indicative of an amount or concentration of the analyte in a first medium (e.g., interstitial fluid (ISF)) of the living animal. In some embodiments, the transceiver 101 may use the sensor measurements to calculate an analyte level in a second medium (e.g., blood). In some embodiments, calculating the analyte level in the second medium may comprise (i) calculating an analyte level in the first medium and (ii) performing a lag compensation, which compensates for the time lag between analyte levels in the second medium and analyte levels in the first medium (e.g., the time lag between a blood analyte level and an ISF analyte level). In some embodiments, the transceiver 101 may convey the calculated second medium analyte level, which may be received by the display device 105.

In some embodiments, the transceiver 101 may trigger a first alarm if the transceiver 101 determines that (1) the calculated second medium analyte level is above a first threshold value (e.g., a high glucose alarm level 1313) and (2) the previous calculated second medium analyte level was not above the first threshold value. In some embodiments, the transceiver 101 may trigger a second alarm if the transceiver 101 determines that (1) the calculated second medium analyte level is below a second threshold value (e.g., a low glucose alarm level 1315) and (2) the previous calculated second medium analyte level was not below the second threshold value. In some embodiments, the transceiver 101 may convey any triggered alarms (e.g., with the calculated second medium analyte level or separately therefrom), and the triggered alarms may be received by the display device 105.

In some embodiments, the transceiver 101 may convey the calculated second medium analyte level with a time stamp. In some embodiments, the time stamp may indicate that time at which (a) the transceiver 101 calculated the second medium analyte level, (b) the transceiver 101 received the one or more sensor measurements used to calculate the second medium analyte level, (c) the sensor 101 took the one or more sensor measurements used to calculate the second medium analyte level, or (d) the transceiver 101 conveyed the measurement command to the sensor 100 that caused the sensor 100 to take the one or more sensor measurements used to calculate the second medium analyte level.

In some embodiments, the historical trend graph 1309 on the display device 105 may simply show calculated second medium analyte levels over time with a line connecting the calculated second medium analyte levels. FIGS. 5A, 6A, 7A, 8A, 9A, 10A, 11A, 12A, 13A, 14A, 15A, 16A, 17A, and 18A show non-limiting examples of historical trend graphs showing raw values with a line connecting them. However, because of the time lag between analyte levels in the first and second media, the transceiver 101 may calculate a second medium analyte level using only the current calculated first medium analyte level and one or more previous first medium analyte levels even though changes in the second medium analyte level have not yet reflected in the first medium analyte level.

In some embodiments, as the display device 105 receives one or more subsequent calculated second medium analyte levels, the one or more subsequent calculated second medium analyte levels may provide additional information about a previous second medium analyte level that was not available to the transceiver 101 when the transceiver 101 calculated the second medium analyte level. Accordingly, in some embodiments, the display device 105 may use one or more subsequent calculated second medium analyte levels to update one or more previous calculated second medium analyte levels. In some embodiments, the one or more updated second medium analyte levels may be smoother and/or more accurate than the original values.

In some embodiments, the display device 105 may use one or more subsequently received raw values (e.g., second medium analyte levels) to perform retrospective smoothing on one or more previous raw values. In some embodiments, the retrospective smoothing may include calculating one or more smoothed values for the one or more previous raw values. In some embodiments, the display device 105 may display the one or more smoothed values in place of the one or more previous raw values (e.g., in the historical trend graph 1309).

In some embodiments, the display device 105 may use one or more polynomial smoothing algorithms to calculate the one or more smoothed values. In different embodiments, the display device 105 may use various smoothing algorithms (e.g., moving average, polynomial regression, local regression) with various window sizes (e.g., 3 raw values, 5 raw values, 7 raw values, or 9 raw values) may be used to calculate the one or more smoothed values.

FIGS. 5B, 6B, 7B, 8B, 9B, 10B, 11B, 12B, 13B, 14B, 15B, 16B, 17B, and 18B show non-limiting examples of historical trend graphs including smoothed values calculated using a smoothing algorithm that fits a moving window of 3 raw values from FIGS. 5A, 6A, 7A, 8A, 9A, 10A, 11A, 12A, 13A, 14A, 15A, 16A, 17A, and 18A, respectively, to a first degree (i.e., linear) polynomial. FIGS. 5C, 6C, 7C, 8C, 9C, 10C, 11C, 12C, 13C, 14C, 15C, 16C, 17C, and 18C show non-limiting examples of historical trend graphs including smoothed values calculated using a smoothing algorithm that fits a moving window of 5 raw values from FIGS. 5A, 6A, 7A, 8A, 9A, 10A, 11A, 12A, 13A, 14A, 15A, 16A, 17A, and 18A, respectively, to a first degree polynomial. FIGS. 5D, 6D, 7D, 8D, 9D, 10D, 11D, 12D, 13D, 14D, 15D, 16D, 17D, and 18D show non-limiting examples of historical trend graphs including smoothed values calculated using a smoothing algorithm that fits a moving window of 7 raw values from FIGS. 5A, 6A, 7A, 8A, 9A, 10A, 11A, 12A, 13A, 14A, 15A, 16A, 17A, and 18A, respectively, to a first degree polynomial. FIGS. 5E, 6E, 7E, 8E, 9E, 10E, 11E, 12E, 13E, 14E, 15E, 16E, 17E, and 18E show non-limiting examples of historical trend graphs including smoothed values calculated using a smoothing algorithm that fits a moving window of 9 raw values from FIGS. 5A, 6A, 7A, 8A, 9A, 10A, 11A, 12A, 13A, 14A, 15A, 16A, 17A, and 18A, respectively, to a first degree polynomial.

FIGS. 5F, 6F, 7F, 8F, 9F, 10F, 11F, 12F, 13F, 14F, 15F, 16F, 17F, and 18F show non-limiting examples of historical trend graphs including smoothed values calculated using a smoothing algorithm that fits a moving window of 5 raw values from FIGS. 5A, 6A, 7A, 8A, 9A, 10A, 11A, 12A, 13A, 14A, 15A, 16A, 17A, and 18A, respectively, to a second degree (i.e., quadratic) polynomial. FIGS. 5G, 6G, 7G, 8G, 9G, 10G, 11G, 12G, 13G, 14G, 15G, 16G, 17G, and 18G show non-limiting examples of historical trend graphs including smoothed values calculated using a smoothing algorithm that fits a moving window of 7 raw values from FIGS. 5A, 6A, 7A, 8A, 9A, 10A, 11A, 12A, 13A, 14A, 15A, 16A, 17A, and 18A, respectively, to a second degree polynomial. FIGS. 5H, 6H, 7H, 8H, 9H, 10H, 11H, 12H, 13H, 14H, 15H, 16H, 17H, and 18H show non-limiting examples of historical trend graphs including smoothed values calculated using a smoothing algorithm that fits a moving window of 9 raw values from FIGS. 5A, 6A, 7A, 8A, 9A, 10A, 11A, 12A, 13A, 14A, 15A, 16A, 17A, and 18A, respectively, to a second degree polynomial.

In some embodiments, the smoothing algorithm may use one or more historical raw values over a moving window and smooth the raw values retrospectively. In some embodiments, the smoothing algorithm may attempt to maximize smoothing while minimizing deviation from the original/raw values. In some embodiments, the smoothing algorithm may have two tuning parameters: (i) a historical moving window size (w) and (ii) polynomial degree (p). In some embodiments, increasing the window size may increase smoothing and/or increase deviation from the original values. In some embodiments, increasing the polynomial degree may decrease smoothing and/or decrease deviation from the original values.

In some embodiments, the smoothing algorithm may include a polynomial degree p (where p is a positive integer) and a window size w (where w>p, and w is an odd positive integer), and the smoothing algorithm may take the following steps whenever the display device 105 receives a raw value Raw(k) corresponding to a time t(k):

$$X(i,j) = \left(t(i) - t\left(k - \frac{w-1}{2}\right)\right)^{(j-1)}$$

$$W(i) = \begin{cases} 1e+6, & \text{Raw}(i) \in \text{First Alarm} \\ 1e+6, & \text{Raw}(i) \in \text{Second Alarm} \\ 1, & \text{else} \end{cases}$$

$$y(i - k + w) = \text{Raw}(i)$$

for $i = k - w + 1, k - w + 2, \ldots, k$ and $$j = 1, \ldots, p+1$$

$$\widetilde{\text{Smooth}} = (X^T \text{diag}(W) X)^{-1} X^T \text{diag}(W) y$$

$$\text{Display}(i) = \begin{cases} \widetilde{\text{Smooth}}\left(i - k + \frac{w+1}{2}\right), & \text{for } i = k - \frac{w-1}{2}, \\ & k - \frac{w-1}{2} + 1, \ldots, k-1 \\ \text{Raw}(i), & \text{for } i = k \end{cases}$$

Figure 19:
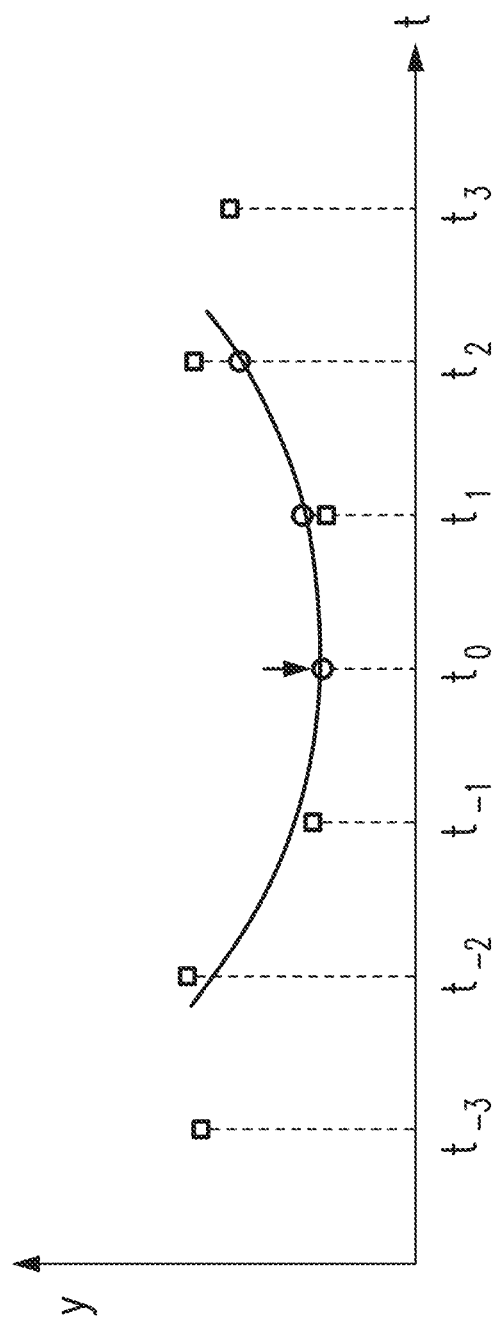
FIG. 19 illustrates a smoothing algorithms according to some embodiments.

If any of the following conditions are observed set p=p+1 and repeat the calculations:

for $i=k-w+1, k-w+2, \ldots, k$ $(\text{Raw}(i) \in \text{First Alarm}) \& (\text{Smooth}(i) \notin \text{First Alarm})$ $(\text{Raw}(i) \in \text{Second Alarm}) \& (\text{Smooth}(i) \notin \text{Second Alarm})$ FIG. 19 shows an example of a non-limiting smoothing algorithm. In FIG. 19, raw values Raw(−3), Raw(−2), Raw(−1), Raw(0), Raw(1), Raw(2), and Raw(3) corresponding to times $t_{-3}, t_{-2}, t_{-1}, t_0, t_1, t_2$, and $t_3$, respectively, are shown in blue. In FIG. 19, raw value Raw(3), which corresponds to time $t_3$, is the current raw value. In some embodiments, as shown in FIG. 19, the smoothing algorithm may use the raw values within the window to calculate one or more smoothed values corresponding to one or more of times $t_0, t_1$, and $t_2$, respectively. In some embodiments, the smoothing algorithm may calculate one or more smoothed values Smooth(i) for i=k−((w−1)/2), k−((w−1)/2)+1, k−((w−1)/2)+2, . . . , k−1, wherein w is the window size, and Raw(k) is the current raw value. In these embodiments, if w=7 and k=3 as shown in FIG. 19, the smoothing algorithm calculates smoothing values Smooth(0), Smooth(1), and Smooth(2) corresponding to times $t_0, t_1$, and $t_2$, respectively. In some embodiments, the display device 105 may display the smoothed values Smooth(0), Smooth(1), and Smooth(2) instead of corresponding raw values (i.e., Raw(0), Raw(1), and Raw(2)). In some embodiments, the display device 105 may display the current raw value Raw(3) in addition to the smoothed values Smooth(0), Smooth(1), and Smooth(2).

In some embodiments, because the transceiver 101 uses raw values (e.g., calculated analyte levels) to trigger the first alarms (e.g., high analyte level alarms) and the second alarms (e.g., low analyte level alarms), the raw values calculated by the transceiver 101 may trigger an alarm that the smoothed values calculated by the display device 105 would not also trigger. As a result, the transceiver 101 may convey a first or second alarm, and the display device 105 may receive the alarm and notify the user (e.g., via the user interface 240) of the alarm, but the smoothed values displayed in the historical trend graph 1309 may be inconsistent with the existence of a first or second alarm condition. User notification of a first or second alarm condition (based on raw values) that is not shown by the smoothed values in the historical trend graph 1309 may cause confusion for the user.

Accordingly, in some embodiments, to prevent this inconsistency from occurring, the display device 105 may perform a consistency check to makes sure that smoothed values corresponding to any raw values that triggered a first or second alarm would also trigger the first or second alarm. In some embodiments, if the display device 105 determines that one or more smoothed values (i) corresponds to a raw value that triggered a first or second alarm and (ii) would not trigger the same alarm, the display device 105 may re-calculate the smoothed values such that none of the smoothed values (i) corresponds to a raw value that triggered a first or second alarm and (ii) would not trigger the same alarm.

In some embodiments, each time the display device 105 receives a raw value calculated by the transceiver 101, the display device 105 may input the current raw value (Raw(n)) and one or more previous raw values (e.g., one or more of Raw(n−1), Raw(n−2), Raw(n−3), Raw(n−4), Raw(n−5), Raw(n−6), Raw(n−7), and Raw(n−8)) into a smoothing algorithm to calculate one or more smoothed previous values (e.g., one or more of Smooth(n−1), Smooth(n−2), Smooth(n−3), and Smooth(n−4)). In some embodiments, the display device 105 may perform a consistency check to make sure that any first alarms (e.g., high analyte level alarms) or second alarms (e.g., low analyte level alarms) triggered by one or more previous raw values (e.g., one or more of Raw(n−1), Raw(n−2), Raw(n−3), Raw(n−4)) would also be triggered by the corresponding smoothed previous values (e.g., one or more of Smooth(n−1), Smooth(n−2), Smooth(n−3), and Smooth(n−4), respectively). If not, the display device 105 may re-calculate the one or more smoothed previous values such that none of the re-calculated smoothed previous values (i) corresponds to a raw value that triggered a first or second alarm and (ii) would not trigger the same alarm. In some embodiments, in re-calculating the smoothed previous values, the display device 105 may increase the polynomial degree of the smoothing algorithm used to re-calculate the smoothed previous values until the re-calculated smoothed previous values satisfy the alarm triggering consistency condition. In some embodiments, the display device 105 may display the current raw value (Raw(n)) and the one or more smoothed previous values (e.g., one or more of Smooth(n−1), Smooth(n−2), Smooth(n−3), and Smooth(n−4)) to the user.

Figure 20:
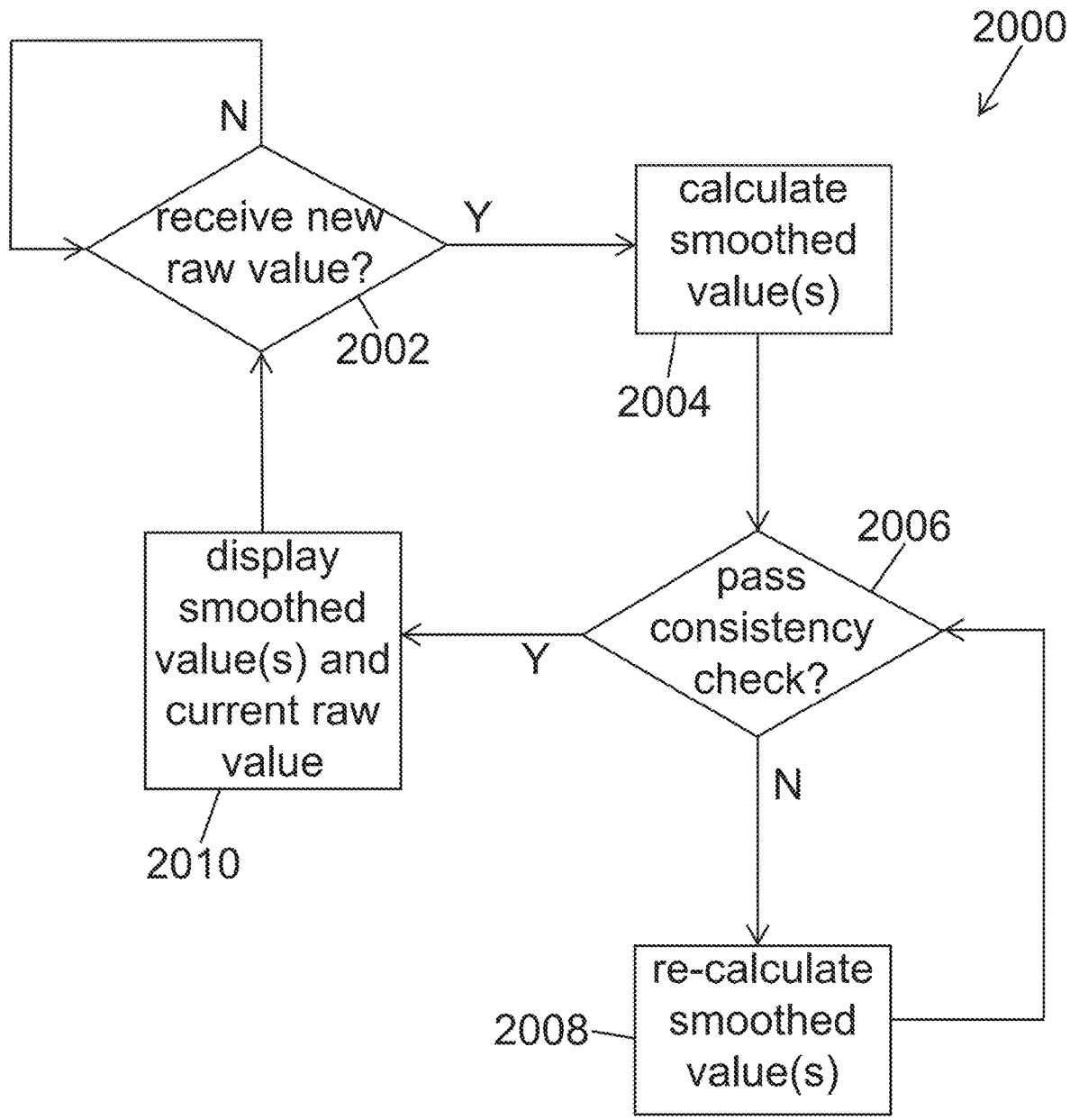
FIG. 20 is a flow chart illustrating a raw value smoothing and display process according to some embodiments.

FIG. 20 is a flow chart illustrating a raw value smoothing and display process 2000 according to some embodiments. In some embodiments, one or more steps of the process 2000 may be performed by an analyte monitoring system, such as, for example, the analyte monitoring system 50. In some embodiments, one or more steps of the process 2000 may be performed by a display device, such as, for example, the display device 105. In some non-limiting embodiments, one or more steps of the process 2000 may be performed by a computer, such as, for example, the computer 210 of the display device 105.

In some embodiments, the process 2000 may include a step 2002 in which the display device 105 determines whether the display device 105 has received a new raw value. In some embodiments, the raw value may be calculated and conveyed by the transceiver 101. In some embodiments, the raw value may be a calculated analyte (e.g., glucose) level. In some embodiments, the raw value may be a calculated second medium (e.g., blood) analyte level. In some embodiments, the received new raw value becomes the current or real time raw value.

In some embodiments, the process 2000 may include a step 2004 in which the display device 105 uses the current raw value and one or more previous raw values to calculate one or more smoothed values. In some embodiments, the display device 105 may use a smoothing algorithm to calculate the one or more smoothed values. In some embodiments, a window size w of the smoothing algorithm may define the number of raw values used to calculate the one or more smoothing values. In some embodiments, the window size w may be any odd positive integer that is greater than the polynomial degree of the smoothing algorithm. In some embodiments, the window size w may be any odd positive integer such as, for example and without limitation, 3, 5, 7, 9, 11, 13, 15, or 17. In some embodiments, the display device 105 may use the current raw value and w−1 previous raw values to calculate the one or more smoothed values. For example and without limitation, if w=9 and the current raw value is Raw(k), the display device 105 may use raw values Raw(k−8), Raw(k−7), Raw(k−6), Raw(k−5), Raw(k−4), Raw(k−3), Raw(k−2), Raw(k−1), and Raw(k) to calculate the one or more smoothed values.

In some embodiments, the display device 105 may calculate w smoothed values that correspond in time to each of the w raw values used to calculate the smoothed values. For example and without limitation, if the display device 105 uses raw values Raw(k−8), Raw(k−7), Raw(k−6), Raw(k−5), Raw(k−4), Raw(k−3), Raw(k−2), Raw(k−1), and Raw(k), the display device 105 may calculate raw values Smooth(k−8), Smooth(k−7), Smooth(k−6), Smooth(k−5), Smooth(k−4), Smooth(k−3), Smooth(k−2), Smooth(k−1), and Smooth(k). However, this is not required, and, in some alternative embodiments, the display device 105 may calculate fewer than w smoothed values.

For example, in some embodiments, the display device 105 may calculate one or more smoothed values Smooth(i) for i=k−((w−1)/2), k−((w−1)/2)+1, k−((w−1)/2)+2, . . . , k−1. In these embodiments, if w=9, the display device would calculate four smoothed values (i.e., Smooth(k−4), Smooth(k−3), Smooth(k−2), and Smooth(k−1)), and, if w=7, the display device would calculate three smoothed values (i.e., Smooth(k−3), Smooth(k−2), and Smooth(k−1)). For other examples, in some alternative embodiments, the display device 105 may calculate (a) one or more smoothed values Smooth(i) for i=k−((w−1)/2), k−((w−1)/2)+1, k−((w−1)/2)+2, . . . , k, (b) one or more smoothed values Smooth(i) for i=k−((w−3)/2), k−((w−3)/2)+1, k−((w−3)/2)+2, . . . , k−1, or (c) one or more smoothed values Smooth(i) for i=k−((w−3)/2), k−((w−3)/2)+1, k−((w−3)/2)+2, . . . , k.

In one embodiment, in step 2004, the polynomial degree of the smoothing algorithm may be p, and the display device 105 may perform the following steps to calculate one or more smoothed values:

$$X(i, j) = \left(t(i) - t\left(k - \frac{w-1}{2}\right)\right)^{(j-1)}$$

$$W(i) = \begin{cases} 1e+6, & \text{Raw}(i) \in \text{First Alarm} \\ 1e+6, & \text{Raw}(i) \in \text{Second Alarm} \\ 1, & \text{else} \end{cases}$$

$$y(i - k + w) = \text{Raw}(i)$$

for $i = k - w + 1, k - w + 2, \ldots, k$ and $$j = 1, \ldots, p+1$$

$$\widehat{\text{Smooth}} = (X^T \text{diag}(W) X)^{-1} X^T \text{diag}(W) y$$

$$\widehat{\text{Smooth}}\left(i - k + \frac{w+1}{2}\right),$$

for $i = k - \frac{w-1}{2}, k - \frac{w-1}{2} + 1, \ldots, k - 1$

In some embodiments, the process 2000 may include a step 2006 in which the display device 105 performs a consistency check. In some embodiments, the consistency check makes sure that smoothed values corresponding to any raw values that triggered a first or second alarm would also trigger the first or second alarm. In some embodiments, a raw value may trigger the first alarm if (1) the raw value is above a first threshold value (e.g., a high glucose alarm level 1313) and (2) the previous raw value was not above the first threshold value. In some embodiments, a raw value may trigger the second alarm if (1) the raw value is below a second threshold value (e.g., a low glucose alarm level 1315) and (2) the previous raw value was not below the second threshold value.

In one embodiment, the one or more smoothed values calculated in step 2004 (or re-calculated in step 2008) may pass the consistency check if both of the following conditions are met for I=k−w+1, k−w+2, . . . , k:

(Raw(i)∈First Alarm)&(Smooth(i)∉First Alarm)     Condition 1

(Raw(i)∈Second Alarm)&(Smooth(i)∉Second Alarm)     Condition 2

In some embodiments, if the one or more smoothed values pass the consistency check, the process 2000 may proceed to a step 2010 in which the one or more smoothed values are displayed. In some embodiments, if the one or more smoothed values does not pass the consistency check, the process 2000 may proceed to a step 2008 in which the one or more smoothed values are re-calculated.

In some embodiments, the process 2000 may include the step 2008 in which the display device 105 re-calculates the one or more smoothed values. In some embodiments, the smoothing algorithm used in step 2008 to re-calculate the one or more smoothing values may be different than the smoothing algorithm used in step 2004 to perform the initial calculation of the one or more smoothing values. In some embodiments, step 2008 may include increasing the polynomial degree of the smoothing algorithm (e.g., increasing by polynomial degree by 1). Accordingly, in some embodiments, the display device 105 may calculate the one or more smoothing values in step 2004 by fitting raw values to a first degree polynomial, (if necessary) re-calculate the one or more smoothing values in step 2008 a first time by fitting raw values to a second degree polynomial, and (if necessary) re-calculate the one or more smoothing values in step 2008 a second time by fitting raw values to a third degree polynomial, and so on until the smoothing values pass the consistency check in step 2006.

In some embodiments, the process 2000 may include a step 2010 in which the display device 105 displays the one or more smoothed values (e.g., in a historical trend graph 1309 on the display 220 of the user interface 240). In some embodiments, the display device 105 may display the one or more smoothed values with the current raw value (e.g., Raw(k)) as shown below:

$$Display(i) = \begin{cases} \widehat{Smooth}\left(i-k+\frac{w+1}{2}\right), & \text{for } i = k-\frac{w-1}{2}, \\ & k-\frac{w-1}{2}+1, \ldots, k-1 \\ Raw(i), & \text{for } i = k \end{cases}$$

In some embodiments, the smoothed value Smooth(k−1) may replace a previous raw value R(k−1) in the historical trend graph 1309. In some embodiments, the smoothed values S(k−2), S(k−3), . . . , S(k−(w−1)/2) may replace a previously calculated and displayed smoothed values in the historical trend graph 1309. In some embodiments, the display device 105 may display previously calculated and displayed smoothed values (e.g., S(k−((w−1)/2)−1), S(k−((w−1)/2)−2), etc.) that correspond to times before earliest time for which a new smoothed value was calculated.

Figure 21:
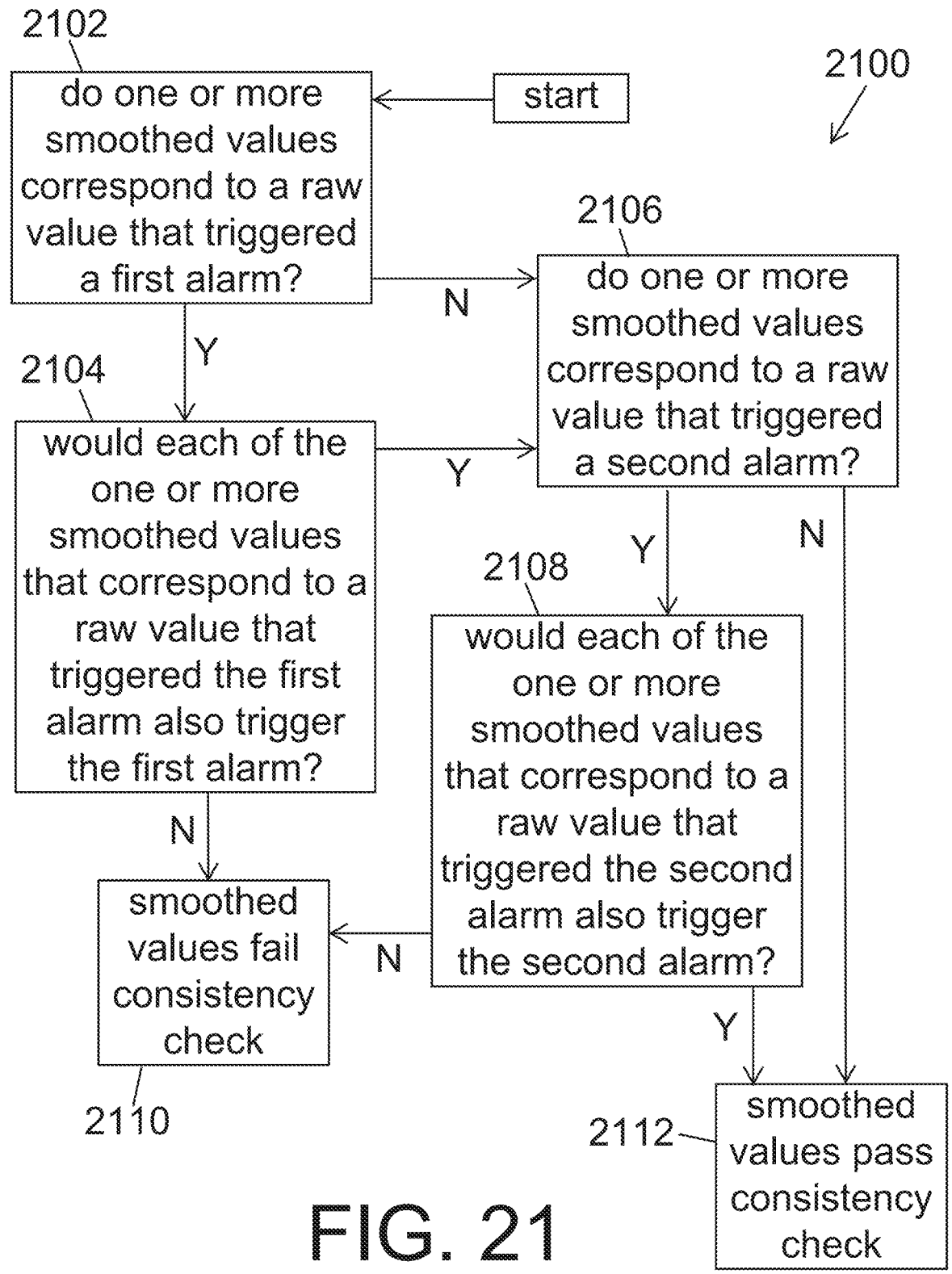
FIG. 21 is a flow chart illustrating a consistency check process according to some embodiments.

FIG. 21 is a flow chart illustrating a consistency check process 2100 that may be performed in step 2006 of the raw value smoothing and display process 2000 according to some embodiments. In some embodiments, one or more steps of the process 2100 may be performed by an analyte monitoring system, such as, for example, the analyte monitoring system 50. In some embodiments, one or more steps of the process 2100 may be performed by a display device, such as, for example, the display device 105. In some non-limiting embodiments, one or more steps of the process 2100 may be performed by a computer, such as, for example, the computer 210 of the display device 105.

In some embodiments, the process 2100 may include a step 2102 in which the display device 105 determines whether one or more of the one or more smoothed values (e.g., calculated in step 2004 or re-calculated in step 2008) corresponds in time to a raw value that triggered the first alarm. In some embodiments, the display device 105 may determine whether raw values triggered the first alarm by determining whether any first alarms corresponding to the raw values were conveyed by the transceiver 101 and received by the display device 105. In some alternative embodiments, the display device 105 may determine whether raw values triggered the first alarm by comparing raw values and previous raw values to the first threshold value (e.g., the high glucose alarm level 1313).

In some embodiments, the process 2100 may include a step 2104 in which the display device 105, if one or more smoothed values were determined in step 2102 to correspond in time to a raw value that triggered the first alarm, determining whether each of the one or more smoothed values that correspond to a raw value that triggered the first alarm also trigger the first alarm. In some embodiments, the display device 2102 may determine that a smoothed value would trigger the first alarm if the smoothed value is above the first threshold value (e.g., the high glucose alarm level 1313). If at least one of the smoothed values that correspond in time to a raw value that triggered the first alarm would not also trigger the first alarm, the process 2100 may proceed to step 2110, which may indicate that the smoothed values failed the consistency check.

In some embodiments, the process 2100 may include a step 2106 in which the display device 105 determines whether one or more of the one or more smoothed values (e.g., calculated in step 2004 or re-calculated in step 2008) corresponds in time to a raw value that triggered the second alarm. In some embodiments, the display device 105 may determine whether raw values triggered the second alarm by determining whether any second alarms corresponding to the raw values were conveyed by the transceiver 101 and received by the display device 105. In some alternative embodiments, the display device 105 may determine whether raw values triggered the second alarm by comparing raw values and previous raw values to the second threshold value (e.g., low glucose alarm level 1315).

In some embodiments, the process 2100 may include a step 2108 in which the display device 105, if one or more smoothed values were determined in step 2106 to correspond in time to a raw value that triggered the second alarm, determining whether each of the one or more smoothed values that correspond to a raw value that triggered the second alarm also trigger the second alarm. In some embodiments, the display device 2102 may determine that a smoothed value would trigger the second alarm if the smoothed value is below the second threshold value (e.g., the low glucose alarm level 1315). If at least one of the smoothed values that correspond in time to a raw value that triggered the second alarm would not also trigger the second alarm, the process 2100 may proceed to step 2110, which may indicate that the smoothed values failed the consistency check.

In some embodiments, if (1) none of the smoothed values (i) corresponds in time to a raw value determined to have triggered the first alarm and (ii) is not above the first threshold value and (2) none of the smoothed values (i) corresponds in time to a raw value determined to have triggered the second alarm and (ii) is not below the second threshold value, the process 2100 may proceed to step 2112, which may indicate that the smoothed values passed the consistency check.

FIGS. 22A-22G illustrate a non-limiting example of a smoothing algorithm having a window size w of 9 is used to display smoothed values in a historical trend graph. In the non-limiting example, the first threshold value, which triggers the first alarm, is shown as T1, and the second threshold value, which triggers the second alarm, is shown as T2. In the non-limiting example, the display device 105 calculated smoothed values Smooth(k−4), Smooth(k−3), Smooth(k−2), and Smooth(k−1) when a new raw value Raw(k) is received. In the non-limiting example, the current raw value and smoothed previous values are displayed in the historical trend graph. In FIGS. 22A-22G, raw values are shown with an "x," and smoothed values are shown by a "o." In FIGS. 22A-22G, when a smoothed value replaces a previously displayed value, the previously displayed value is shown with a "-."

Figure 22A:
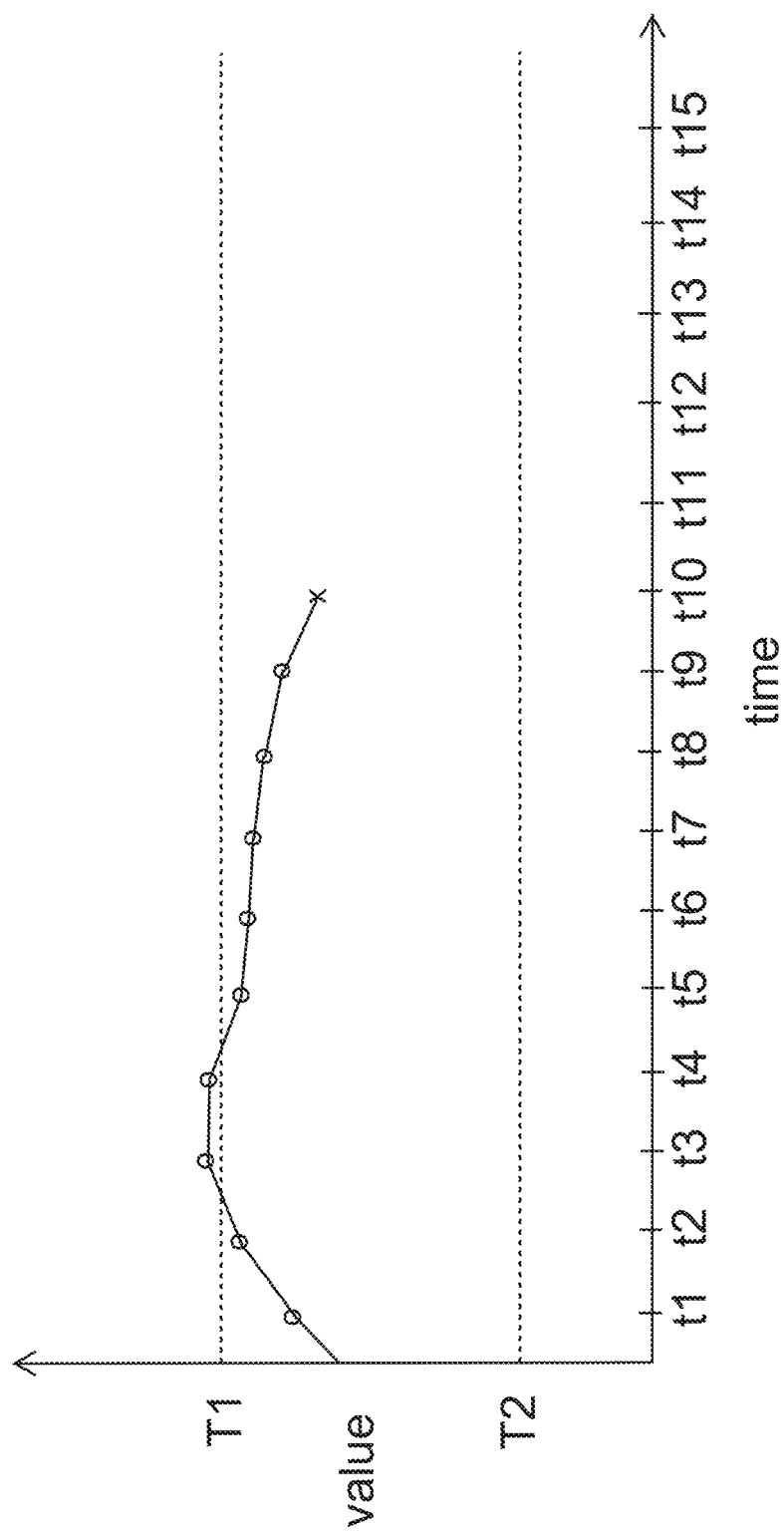
FIGS. 22A-22G non-limiting examples of a historical trend graph according to some embodiments.

FIG. 22A shows the historical trend graph after the display device 105 has received a raw value Raw(10) corresponding to a time t10. As shown in FIG. 22A, the historical trend graph displays the raw value Raw(10) and previous smoothed values Smooth(1) through Smooth(9).

Figure 22B:
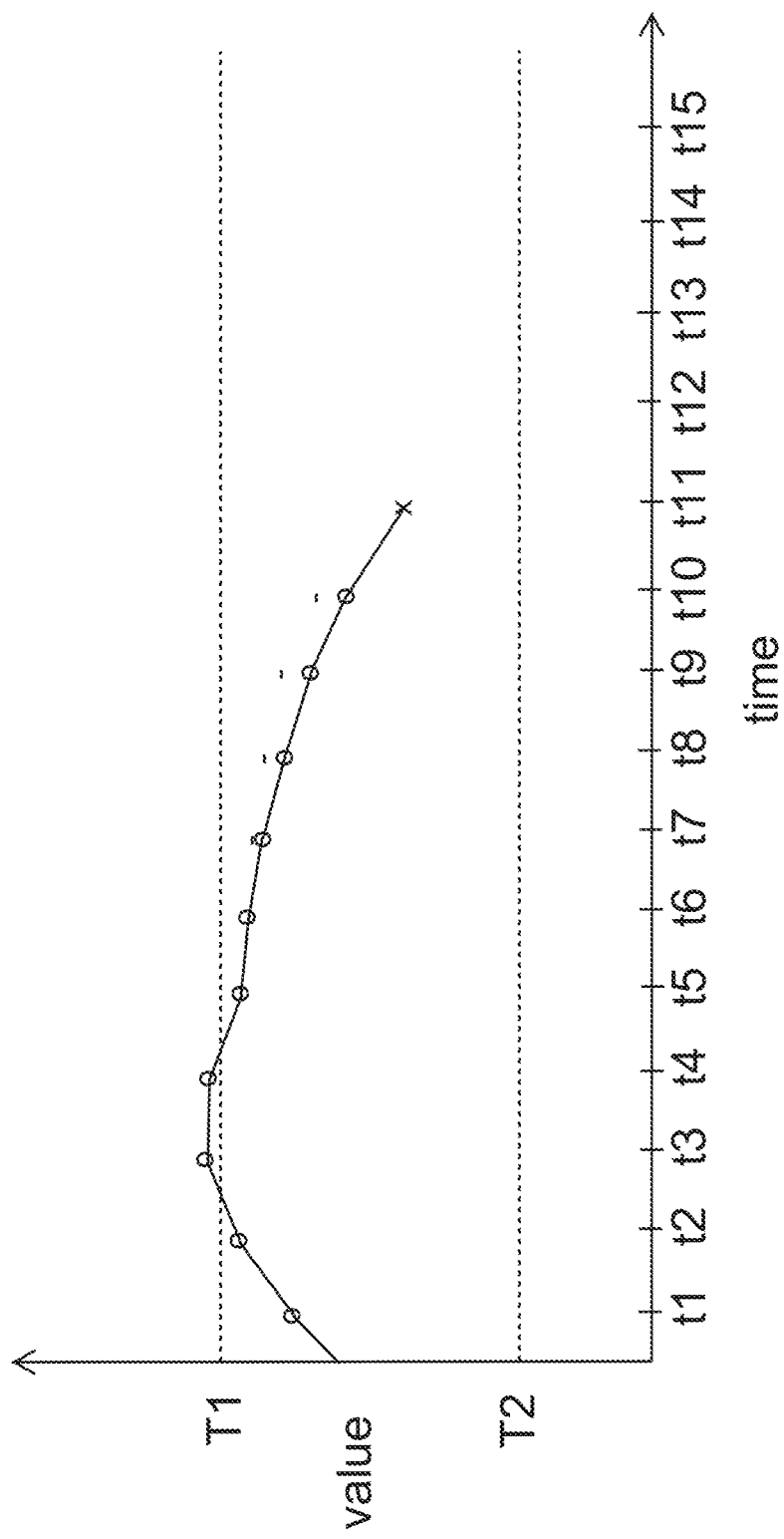

FIG. 22B shows the historical trend graph after the display device 105 has received a raw value Raw(11) corresponding to a time t11. The display device 105 has used raw values Raw(3) through Raw(11) to calculate smoothed values Smooth(7) through Smooth(10). The calculated smoothed values pass the consistency check. As shown in FIG. 22B, the display device 105 has updated the historical trend graph (i) by replacing the smoothed values previously displayed at times t7 through t9 with the newly calculated smoothed values Smooth(7) through Smooth(9), respectively, (ii) by replacing the raw value Raw(10) previously displayed at time t10 with the newly calculated smoothed value Smooth(10), and (iii) to include the current raw value Raw(11) at time t11. As shown in FIG. 22B, the previously calculated and displayed smoothed values at t1 through t6 have not changed.

Figure 22C:
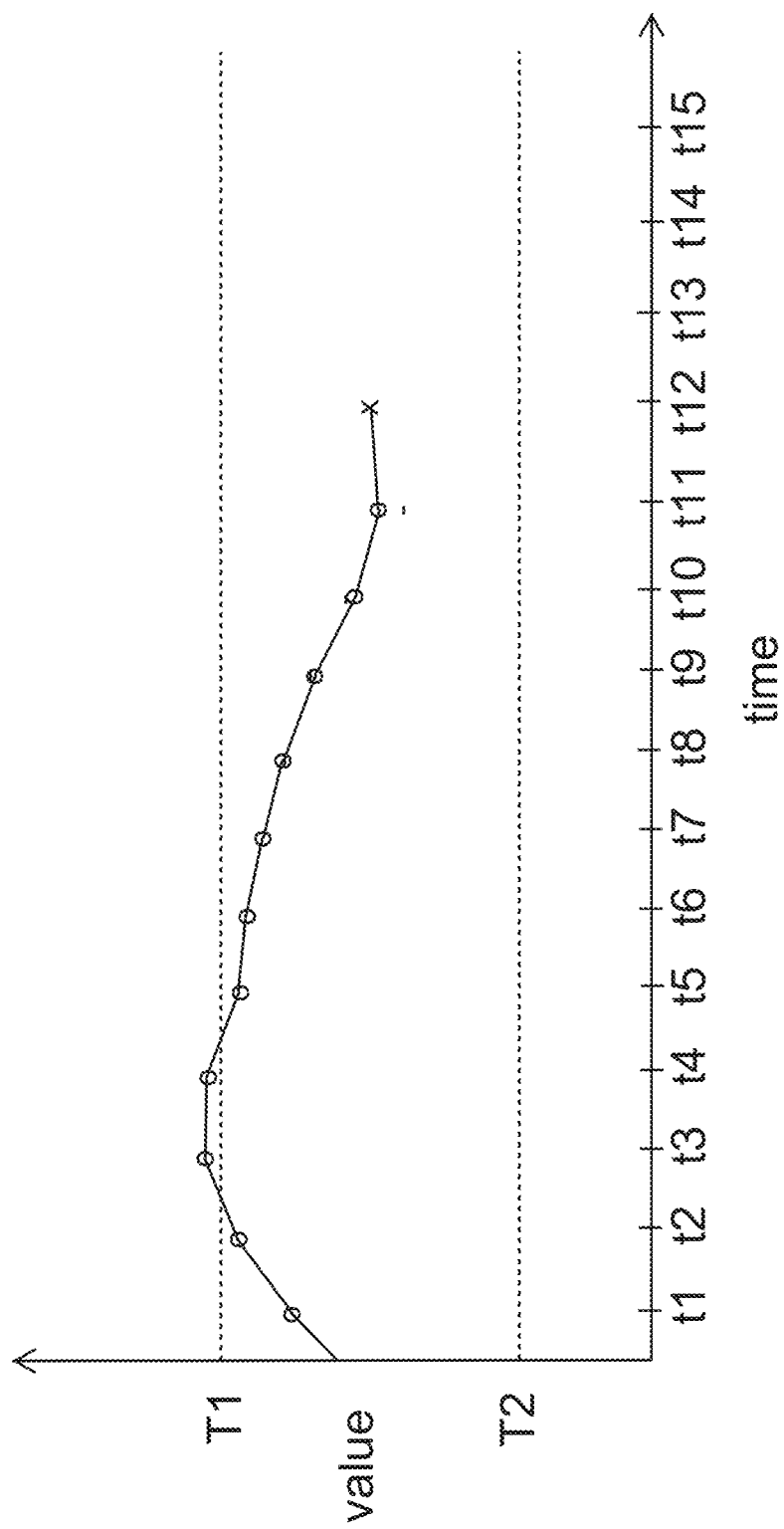

FIG. 22C shows the historical trend graph after the display device 105 has received a raw value Raw(12) corresponding to a time t12. The display device 105 has used raw values Raw(4) through Raw(12) to calculate smoothed values Smooth(8) through Smooth(11). The calculated smoothed values pass the consistency check. As shown in FIG. 22C, the display device 105 has updated the historical trend graph (i) by replacing the smoothed values previously displayed at times t8 through t10 with the newly calculated smoothed values Smooth(8) through Smooth(10), respectively, (ii) by replacing the raw value Raw(11) previously displayed at time t11 with the newly calculated smoothed value Smooth(11), and (iii) to include the current raw value Raw(12) at time t12. As shown in FIG. 22C, the previously calculated and displayed smoothed values at t1 through t7 have not changed.

Figure 22D:
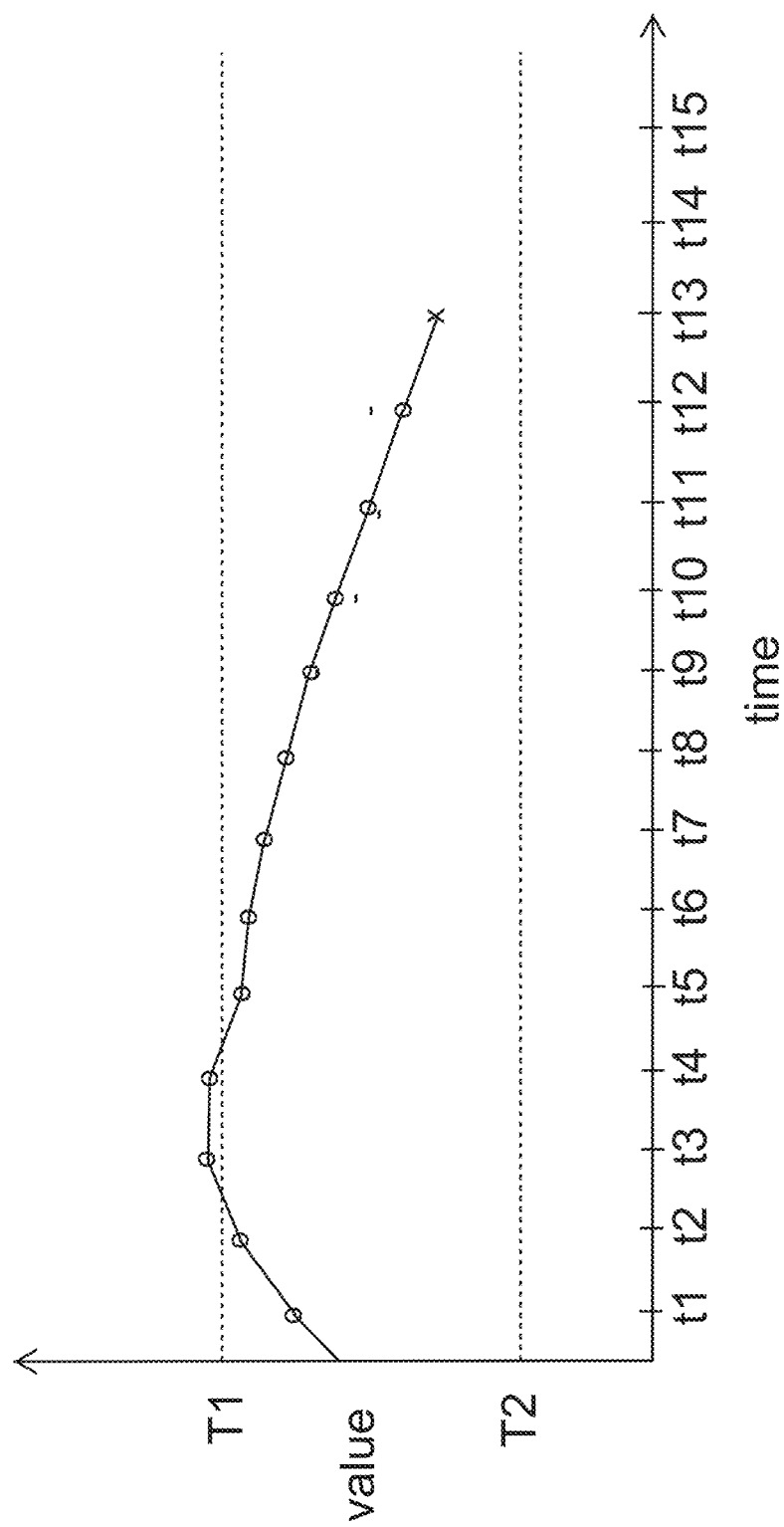

FIG. 22D shows the historical trend graph after the display device 105 has received a raw value Raw(13) corresponding to a time t13. The display device 105 has used raw values Raw(5) through Raw(13) to calculate smoothed values Smooth(9) through Smooth(12). The calculated smoothed values pass the consistency check. As shown in FIG. 22D, the display device 105 has updated the historical trend graph (i) by replacing the smoothed values previously displayed at times t9 through t11 with the newly calculated smoothed values Smooth(9) through Smooth(11), respectively, (ii) by replacing the raw value Raw(12) previously displayed at time t12 with the newly calculated smoothed value Smooth(12), and (iii) to include the current raw value Raw(13) at time t13. As shown in FIG. 22D, the previously calculated and displayed smoothed values at t1 through t8 have not changed.

Figure 22E:
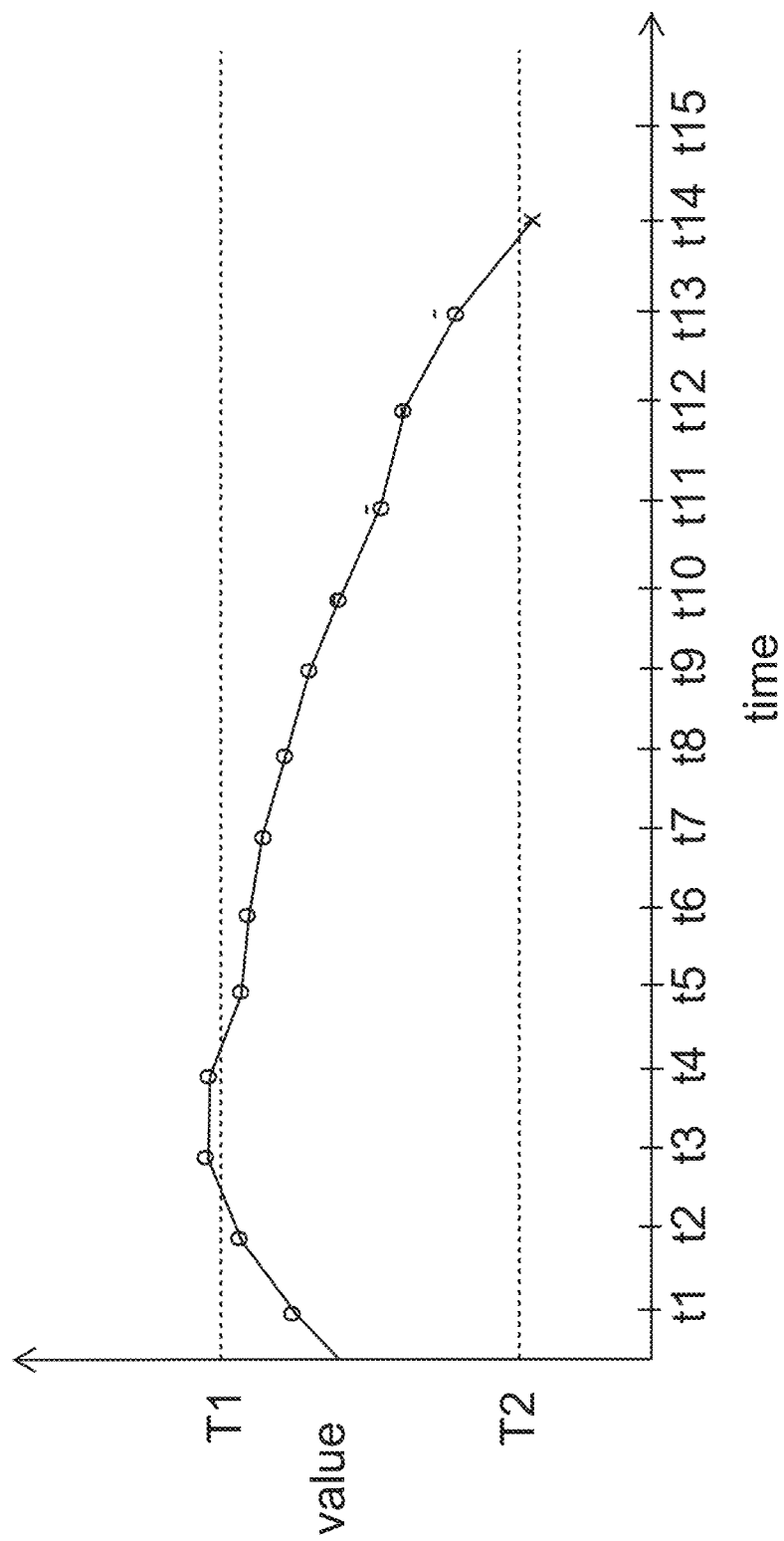

FIG. 22E shows the historical trend graph after the display device 105 has received a raw value Raw(14) corresponding to a time t14. The raw value Raw(14) has triggered the second alarm because (1) the raw value Raw(14) is below the second threshold value T2 and (2) the previous raw value Raw(13) was not below the second threshold value. See FIG. 22D. The display device 105 has used raw values Raw(6) through Raw(14) to calculate smoothed values Smooth(10) through Smooth(13). The calculated smoothed values pass the consistency check. As shown in FIG. 22E, the display device 105 has updated the historical trend graph (i) by replacing the smoothed values previously displayed at times t10 through t12 with the newly calculated smoothed values Smooth(10) through Smooth(12), respectively, (ii) by replacing the raw value Raw(13) previously displayed at time t13 with the newly calculated smoothed value Smooth(13), and (iii) to include the current raw value Raw(14) at time t14. As shown in FIG. 22E, the previously calculated and displayed smoothed values at t1 through t9 have not changed.

Figure 22F:
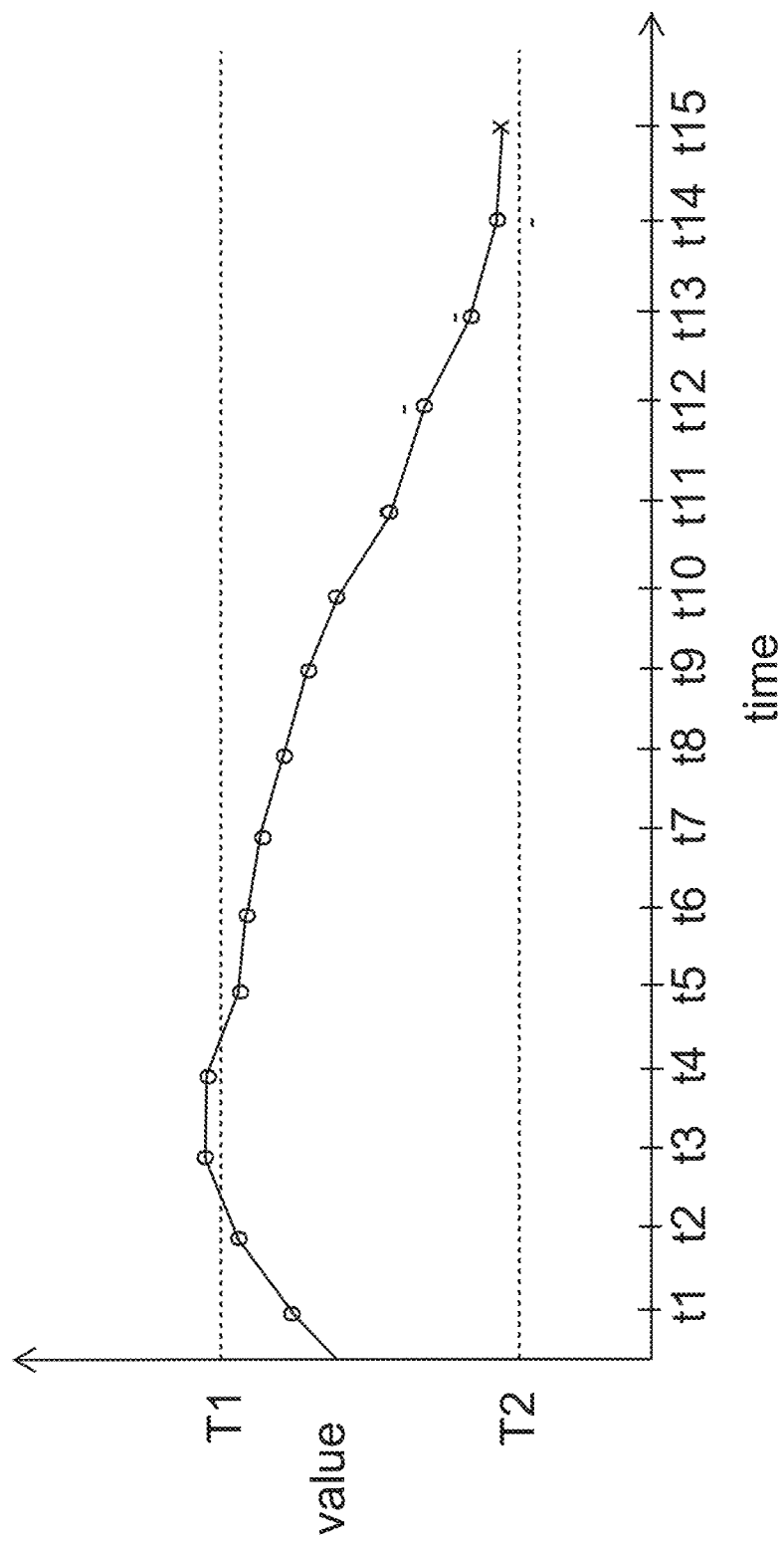
Figure 22G:
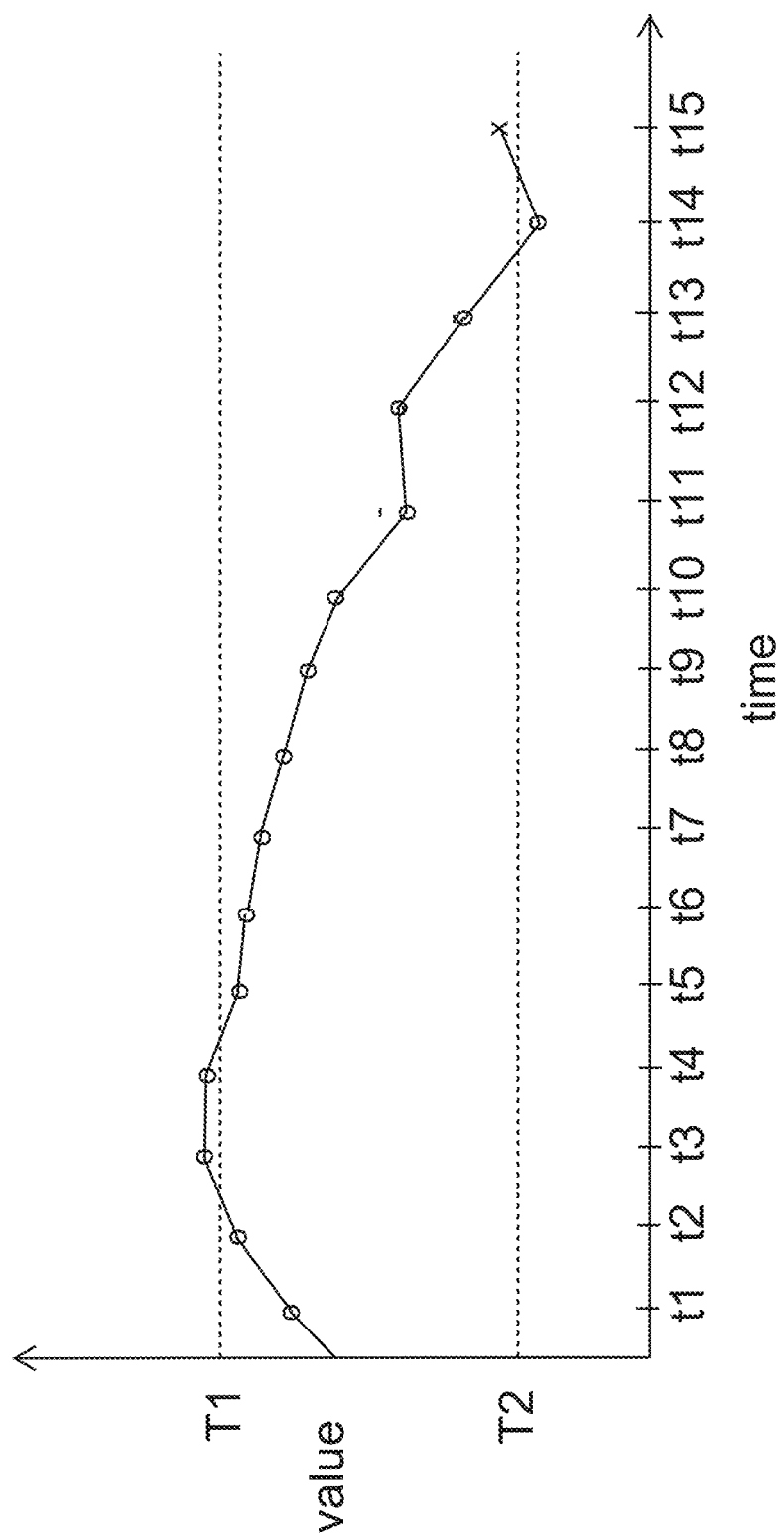

FIGS. 22F and 22G show historical trend graphs after the display device 105 has received a raw value Raw(15) corresponding to a time t15. FIG. 22F shows a historical trend graph that might occur if smoothed values were used in the absence of a consistency check. The display device 105 has used raw values Raw(7) through Raw(15) to calculate smoothed values Smooth(11) through Smooth(14). As shown in FIG. 22F, the calculated smoothed values Smooth(11) through Smooth(14) fail the consistency check because smoothed value Smooth(14) corresponds in time to a raw value Raw(14) that triggered the second alarm and is not below the second threshold value T2. The lack of a value at time t14 in the historical trend graph shown in FIG. 22F that would have triggered the second alarm may cause confusion for the user, who would have been alerted of the presence of the second alarm at time t14.

As the calculated smoothed values do not pass the consistency check, the display device 105 does not display them and instead re-calculates the smoothed values using the raw values Raw(7) through Raw(15) and a different smoothing algorithm (e.g., a smoothing algorithm having an increased polynomial degree). The re-calculated smoothed values Smooth(11) through Smooth(14) pass the consistency check because, as shown in FIG. 22G, Smooth(14) is below the second threshold value T2 (as was the corresponding raw value Raw(14), which triggered the second alarm). As shown in FIG. 22G, the display device 105 has updated the historical trend graph (i) by replacing the smoothed values previously displayed at times t11 through t13 with the newly calculated smoothed values Smooth(11) through Smooth(13), respectively, (ii) by replacing the raw value Raw(14) previously displayed at time t14 with the newly calculated smoothed value Smooth(14), and (iii) to include the current raw value Raw(15) at time t15. As shown in FIG. 22G, the previously calculated and displayed smoothed values at t1 through t10 have not changed.

Embodiments of the present invention have been fully described above with reference to the drawing figures. Although the invention has been described based upon these preferred embodiments, it would be apparent to those of skill in the art that certain modifications, variations, and alternative constructions could be made to the described embodiments within the spirit and scope of the invention. For instance, although many of the embodiments described above show the current raw value in the historical trend graph, this is not required, and, in some alternative embodiments, only smoothed values may be displayed in the historical trend graph including a smoothed value in place of the current raw value. Also, although the invention is described above in the context of an analyte monitoring system in which the display device 105 receives raw values that are second medium (e.g., blood) analyte levels calculated indirectly using measurements of analyte levels in a first medium (e.g., interstitial fluid), the invention is applicable to any system that indirectly measures a physical or chemical parameter in real time (or approximately real time) and then updates the measurement at a later time. For example, the invention is applicable to a system that measures a physical or chemical parameter from a remote location in real time and then has the opportunity to update that measurement at a later time when the thermodynamics have equilibrated.

What is claimed is:

1. An analyte monitoring system comprising:
an analyte sensor configured to generate sensor measurements, wherein the sensor measurements include one or more light measurements and one or more temperature measurements, and at least the one or more light measurements are indicative of an amount or concentration of an analyte in a medium;
a transceiver configured to receive the sensor measurements via a wireless or wired connection and use at least the sensor measurements to calculate a first raw value corresponding to a first time, wherein the first raw value is an analyte level; and
a display device comprising:
a transceiver interface device configured to receive wirelessly the first raw value corresponding to the first time;
a user interface; and
a computer including a non-transitory memory and a processor, wherein the computer is configured to:
use the user interface to display a graph including at least the first raw value at the first time;
use a first smoothing algorithm and raw values including the first raw value to calculate a first smoothed value corresponding to the first time, wherein the first smoothing algorithm fits the raw values to a first polynomial;
determine whether the first raw value triggered a first alarm for the first raw value being above a first threshold value;
determine whether the first raw value triggered a second alarm for the first raw value being below a second threshold value;
if the first raw value was determined to have triggered the first alarm, determine whether the first smoothed value is not above the first threshold value;
if the first raw value was determined to have triggered the second alarm, determine whether the first smoothed value is not below the second threshold value;
if the first raw value was determined to have triggered the first alarm and the first smoothed value was determined to be not above the first threshold value, recalculate the first smoothed value to be above the first threshold value, wherein a second smoothing algorithm is used to recalculate the first smoothed value, the second smoothing algorithm fits the raw values to a second polynomial, and the second smoothing algorithm is different than the first smoothing algorithm;
if the first raw value was determined to have triggered the second alarm and the first smoothed value was determined to be not below the second threshold value, recalculate the first smoothed value to be below the second threshold value, wherein the second smoothing algorithm is used to recalculate the first smoothed value; and
after displaying the graph including at least the first raw value at the first time, calculating the first smoothed value, and recalculating the first smoothed value if the first raw value was determined to have triggered the first alarm and the first smoothed value was determined to be not above the first threshold value or if the first raw value was determined to have triggered the second alarm and the first smoothed value was determined to be not below the second threshold value, update the graph by replacing the first raw value with the first smoothed value at the first time if the first smoothed value has not been recalculated or by replacing the first raw value with the recalculated first smoothed value if the first smoothed value has been recalculated.

2. The analyte monitoring system of claim 1, wherein a degree of the second polynomial used in the second smoothing algorithm is greater than a degree of the first polynomial used in the first smoothing algorithm.

3. The analyte monitoring system of claim 1, wherein the first polynomial is a first degree polynomial, and the second polynomial is a second degree polynomial.

4. The analyte monitoring system of claim 1, wherein the first polynomial is a second degree polynomial, and the second polynomial is a third degree polynomial.

5. The analyte monitoring system of claim 1, wherein recalculating the first smoothed value comprises recalculating the first smoothed value with smoothing algorithms of increasing polynomial degree until the first smoothed value is above the first threshold value or below the second threshold value.

6. The analyte monitoring system of claim 1, wherein:
the transceiver interface device is further configured to receive a second raw value corresponding to a second time, which is later than the first time;
at least the first and second raw values are used to calculate the first smoothed value corresponding to the first time; and
the updated graph includes the first smoothed value or the recalculated first smoothed value at the first time, includes the second raw value at the second time, and does not include the first raw value at the first time.

7. The analyte monitoring system of claim 6, wherein the transceiver interface device is further configured to receive a third raw value corresponding to a third time, which is later than the second time, and the computer is further configured to:
- use at least the first, second, and third raw values to calculate at least a second smoothed value corresponding to the first time and a third smoothed value corresponding to the second time;
- if the first raw value was determined to have triggered the first alarm, determine whether the second smoothed value is not above the first threshold value;
- if the first raw value was determined to have triggered the second alarm, determine whether the second smoothed value is not below the second threshold value;
- determine whether the second raw value triggered the first alarm;
- determine whether the second raw value triggered the second alarm;
- if the second raw value was determined to have triggered the first alarm, determine whether the third smoothed value is not above the first threshold value;
- if the second raw value was determined to have triggered the second alarm, determine whether the third smoothed value is not below the second threshold value;
- if at least one of the second and third smoothed values (a)(i) corresponds in time to a raw value determined to have triggered the first alarm and (ii) was determined to not be above the first threshold value or (b)(i) corresponds in time to a raw value determined to have triggered the second alarm and (ii) was determined to not be below the second threshold value, recalculate the second and third smoothed values such that (1) none of the second and third smoothed values (i) corresponds in time to the raw value determined to have triggered the first alarm and (ii) is not above the first threshold value and (2) none of the second and third smoothed values (i) corresponds in time to the raw value determined to have triggered the second alarm and (ii) is not below the second threshold value; and
- after updating the graph, calculating the second smoothed value, and recalculating the second and third smoothed values if at least one of the second and third smoothed values (a)(i) corresponds in time to a raw value determined to have triggered the first alarm and (ii) was determined to not be above the first threshold value or (b)(i) corresponds in time to a raw value determined to have triggered the second alarm and (ii) was determined to not be below the second threshold value, update the updated graph by replacing the first smoothed value or the recalculated first smoothed value at the first time with the second smoothed value if the second smoothed value has not been recalculated or with the recalculated second smoothed value if the second smoothed value has been recalculated, by replacing the second raw value at the second time with the third smoothed value at the second time if the third smoothed value has not been recalculated or with the recalculated third smoothed value if the third smoothed value has been recalculated, and to include additionally the third raw value at the third time.

8. The analyte monitoring system of claim 1, wherein at least the first raw value and one or more previous raw values corresponding to one or more times prior to the first time are used to calculate the first smoothed value corresponding to the first time and one or more smoothed previous values corresponding to the one or more times prior to the first time, and the computer is further configured to:
- determine whether at least one of the smoothed previous values corresponds in time to a previous raw value that triggered the first alarm;
- determine whether at least one of the smoothed previous values corresponds in time to a previous raw value that triggered the second alarm;
- if at least one of the smoothed previous values was determined to correspond in time to the previous raw value that triggered the first alarm, determine whether the at least one of the smoothed previous values that corresponds in time to the previous raw value that triggered the first alarm is not above the first threshold value;
- if at least one of the smoothed previous values was determined to correspond in time to the previous raw value that triggered the second alarm, determine whether the at least one of the smoothed previous values that corresponds in time to the previous raw value that triggered the second alarm is not below the second threshold value;
- if at least one of the one or more smoothed previous values (a)(i) corresponds in time to the previous raw value determined to have triggered the first alarm and (ii) was determined to not be above the first threshold value or (b)(i) corresponds in time to the raw value determined to have triggered the second alarm and (ii) was determined to not be below the second threshold value, recalculate the first smoothed value and the one or more smoothed previous values such that (1) none of the first smoothed value and the one or more smoothed previous values (i) corresponds in time to the raw value determined to have triggered the first alarm and (ii) is not above the first threshold value and (2) none of the first smoothed value and the one or more smoothed previous values (i) corresponds in time to the raw value determined to have triggered the second alarm and (ii) is not below the second threshold value; and
- use the user interface to display in the graph at least the first smoothed value at the first time if the first smoothed value has not be recalculated, the recalculated first smoothed value at the first time if the first smoothed value has been recalculated, the one or more smoothed previous values at the one or more times prior to the first time if the one or more smoothed previous values have not been recalculated, and the one or more recalculated smoothed previous values at the one or more times prior to the first time if the one or more smoothed previous values have been recalculated, wherein the updated graph does not include the first raw value at the first time.

9. The analyte monitoring system of claim 1, wherein the first raw value triggers the first alarm if (1) the first raw value is above the first threshold value and (2) a previous raw value corresponding to a time that most immediately precedes the first time was not above the first threshold value, and the first raw value triggers the second alarm if (1) the first raw value is below the second threshold value and (2) the previous raw value corresponding to the time that most immediately precedes the first time was not below the second threshold value.

10. The analyte monitoring system of claim 1, wherein the first raw value is a blood glucose level.

11. The analyte monitoring system of claim 1, wherein the computer is configured to not recalculate the first smoothed value if the first raw value was not determined to have triggered the first alarm and the first raw value was not determined to have triggered the second alarm, if the first raw value was determined to have triggered the first alarm and the first smoothed value was determined to be above the first threshold value, or if the first raw value was determined to have triggered the second alarm and the first smoothed value was determined to be below the second threshold value.

12. A method performed by an analyte monitoring system, the method comprising:
   using an analyte sensor of the analyte monitoring system to generate sensor measurements, wherein the sensor measurements include one or more light measurements and one or more temperature measurements, and at least the one or more light measurements are indicative of an amount or concentration of an analyte in a medium;
   using a transceiver of the analyte monitoring system to receive the sensor measurements via a wireless or wired connection and use at least the sensor measurements to calculate a first raw value corresponding to a first time, wherein the first raw value is an analyte level;
   using a display device of the analyte monitoring system to receive wirelessly the first raw value corresponding to the first time;
   using a user interface of the display device to display a graph including at least the first raw value at the first time;
   using the display device to use a first smoothing algorithm and raw values including the first raw value to calculate a first smoothed value corresponding to the first time, wherein the first smoothing algorithm fits the raw values to a first polynomial;
   using the display device to determine that (a) the first raw value triggered a first alarm for the first raw value being above a first threshold value and the first smoothed value is not above the first threshold value or (b) the first raw value triggered a second alarm for the first raw value being below a second threshold value and the first smoothed value is not below the second threshold value;
   using the display device to, in response to determining that (a) the first raw value triggered the first alarm and the first smoothed value is not above the first threshold value or (b) the first raw value triggered the second alarm and the first smoothed value is not below the second threshold value, recalculate the first smoothed value to be (a) above the first threshold value if the first raw value triggered the first alarm or (b) below the second threshold value if the first raw value triggered the second alarm, wherein a second smoothing algorithm is used to recalculate the first smoothed value, the second smoothing algorithm fits the raw values to a second polynomial, and the second smoothing algorithm is different than the first smoothing algorithm; and
   after displaying the graph including at least the first raw value at the first time, calculating the first smoothed value, and recalculating the first smoothed value, using the display device to update the graph by replacing the first raw value with the recalculated first smoothed value at the first time.

13. The method of claim 12, wherein a degree of the second polynomial used in the second smoothing algorithm is greater than a degree of the first polynomial used in the first smoothing algorithm.

14. The method of claim 12, wherein the first polynomial is a first degree polynomial, and the second polynomial is a second degree polynomial.

15. The method of claim 12, wherein the first polynomial is a second degree polynomial, and the second polynomial is a third degree polynomial.

16. The method of claim 12, wherein recalculating the first smoothed value comprises recalculating at least the first smoothed value with smoothing algorithms of increasing polynomial degree until the first smoothed value is above the first threshold value.

17. The method of claim 12, further comprising using the display device to receive a second raw value corresponding to a second time, which is later than the first time;
   wherein at least the first and second raw values are used to calculate and re-calculate the first smoothed value corresponding to the first time; and
   the updated graph includes the recalculated first smoothed value at the first time and the second raw value at the second time but does not include the first raw value at the first time.

18. The method of claim 17, further comprising:
   using the display device to receive a third raw value corresponding to a third time, which is later than the second time;
   using the display device to use at least the first, second, and third raw values to calculate at least a second smoothed value corresponding to the first time and a third smoothed value corresponding to the second time;
   using the display device to determine that at least one of the second and third smoothed values (a)(i) corresponds in time to a raw value that triggered the first alarm and (ii) is not above the first threshold value or (b)(i) corresponds in time to a raw value that triggered the second alarm and (ii) is not below the second threshold value;
   using the display device to, in response to determining that at least one of the second and third smoothed values (a)(i) corresponds in time to the raw value that triggered the first alarm and (ii) is not above the first threshold value or (b)(i) corresponds in time to the raw value that triggered the second alarm and (ii) is not below the second threshold value, recalculate the second and third smoothed values such that (1) none of the second and third smoothed values (i) corresponds in time to the raw value that triggered the first alarm and (ii) is not above the first threshold value and (2) none of the second and third smoothed values (i) corresponds in time to the raw value that triggered the second alarm and (ii) is not below the second threshold value; and
   after using the display device to update the graph, calculate the second smoothed value, and recalculate the second smoothed value, using the display device to update the updated graph by replacing the recalculated first smoothed value with the recalculated second smoothed value at the first time, by replacing the recalculated second raw value with the recalculated third smoothed value at the second time, and to include additionally the third raw value at the third time.

19. The method of claim 12, wherein at least the first raw value and one or more previous raw values corresponding to one or more times prior to the first time are used to calculate the first smoothed value corresponding to the first time and one or more smoothed previous values corresponding to the one or more times prior to the first time, and the method further comprises:
   using the display device to determine that at least one of the one or more smoothed previous values (a)(i) corresponds in time to a previous raw value that triggered the first alarm and (ii) is not above the first threshold value or (b)(i) corresponds in time to a raw value that triggered the second alarm and (ii) is not below the second threshold value;

using the display device to, in response to determining that at least one of the one or more smoothed previous values (a)(i) corresponds in time to the previous raw value that triggered the first alarm and (ii) is not above the first threshold value or (b)(i) corresponds in time to the raw value that triggered the second alarm and (ii) is not below the second threshold value, recalculate the first smoothed value and the one or more smoothed previous values such that (1) none of the first smoothed value and the one or more smoothed previous values (i) corresponds in time to the raw value that triggered the first alarm and (ii) is not above the first threshold value and (2) none of the first smoothed value and the one or more smoothed previous values (i) corresponds in time to the raw value that triggered the second alarm and (ii) is not below the second threshold value; and using the user interface to display in the graph at least the recalculated first smoothed value at the first time and the one or more recalculated smoothed previous values at the one or more times prior to the first time, wherein the updated graph does not include the first raw value at the first time.

20. The method of claim 12, wherein the first raw value triggers the first alarm if (1) the first raw value is above the first threshold value and (2) a previous raw value corresponding to a time that most immediately precedes the first time was not above the first threshold value, and the first raw value triggers the second alarm if (1) the first raw value is below the second threshold value and (2) the previous raw value corresponding to the time that most immediately precedes the first time was not below the second threshold value.

21. The method of claim 12, wherein the first raw value is a blood glucose level.

* * * * *